(12) United States Patent
Chang

(10) Patent No.: US 9,463,242 B2
(45) Date of Patent: Oct. 11, 2016

(54) METHODS FOR TREATING PROSTATE CANCER

(75) Inventor: Chawnshang Chang, Pittsford, NY (US)

(73) Assignee: UNIVERSITY OF ROCHESTER, Rochester, NY (US)

(*) Notice: Subject to any disclaimer, the term of this patent is extended or adjusted under 35 U.S.C. 154(b) by 242 days.

(21) Appl. No.: 14/115,217

(22) PCT Filed: May 3, 2012

(86) PCT No.: PCT/US2012/036347
§ 371 (c)(1),
(2), (4) Date: Nov. 1, 2013

(87) PCT Pub. No.: WO2012/151413
PCT Pub. Date: Nov. 8, 2012

(65) Prior Publication Data
US 2014/0105908 A1    Apr. 17, 2014

Related U.S. Application Data

(60) Provisional application No. 61/482,066, filed on May 3, 2011.

(51) Int. Cl.

| A61K 31/353 | (2006.01) |
|---|---|
| A61K 31/355 | (2006.01) |
| A61K 31/706 | (2006.01) |
| A61K 39/395 | (2006.01) |
| A61K 45/06 | (2006.01) |
| A61K 31/121 | (2006.01) |
| A61K 31/167 | (2006.01) |
| A61K 31/277 | (2006.01) |
| A61K 31/4166 | (2006.01) |
| A61K 31/44 | (2006.01) |
| A61K 31/09 | (2006.01) |

(52) U.S. Cl.
CPC ........... *A61K 39/3955* (2013.01); *A61K 31/09* (2013.01); *A61K 31/121* (2013.01); *A61K 31/167* (2013.01); *A61K 31/277* (2013.01); *A61K 31/353* (2013.01); *A61K 31/355* (2013.01); *A61K 31/4166* (2013.01); *A61K 31/44* (2013.01); *A61K 31/706* (2013.01); *A61K 45/06* (2013.01)

(58) Field of Classification Search
CPC ............ A61K 31/355; A61K 31/353; A61K 31/706; A61K 45/06
See application file for complete search history.

(56) References Cited

U.S. PATENT DOCUMENTS 7,355,081 B2    4/2008 Lee et al.

OTHER PUBLICATIONS

Heinonen et al. JNCI, 1998, vol. 90, Issue6, pp. 440-446.*
Torring et al. Prostate, 2003, vol. 56, No. 2, pp. 142-149.*
Loberg et al. Neoplasia, 2007, vol. 9, No. 7, pp. 556-562.*
Taylor et al. Endocr. Relat. Cancer, 2010, vol. 17, pp. R273-R285.*

Akaza, H., Current status and prospects of androgen depletion therapy for prostate cancer, *Best Practice & Research Clinical Endocrinology & Metabolism* 22:293-302 (2008).
Blanpain, et al., Epithelial stem cells: turning over new leaves, *Cell* 128:445-458 (2007).
Bonaccorsi, et al., Gefitinib ('IRESSA', ZD1839) inhibits EGF-induced invasion in prostate cancer cells by suppressing PI3 K/AKT activation, *Journal of Cancer Research & Clinical Oncology* 130:10:604-614 (Oct. 2004).
Bonkhoff, et al., Relation between Bcl-2, cell proliferation, and the androgen receptor status in prostate tissue and precursors of prostate cancer, *Prostate* 34:4:251-258 (Mar. 1, 1998).
Bonkhoff, et al., The proliferative function of basal cells in the normal and hyperplastic human prostate, *Prostate* 24:3:114-118 (1994).
Cristofaro, et al., WAY-202196, a selective estrogen receptor-beta agonist, protects against death in experimental septic shock, *Journal of Critical Care Medicine* 34:8:2188-2193 (Aug. 2006).
Crocoll, et al., Expression of androgen receptor mRNA during mouse embryogenesis, *Mechanisms of Development* 72:1-2:175-178 (1998).
Cunha, G., Epithelial-stromal interactions in development of the urogenital tract, *International Review of Cytology* 47:137-194 (1976).
Cunha, et al., Hormonal, cellular, and molecular regulation of normal and neoplastic prostatic development, *The Journal of Steroid Biochemistry and Molecular Biology* 92:4:221-236 (Nov. 2004).
Cunha, et al., Hormone-induced morphogenesis and growth: role of mesenchymal-epithelial interactions, *Recent Progress in Hormone Research* 39:559-598 (1983).
Cunha, et al., Stromal-epithelial interactions—I. Induction of prostatic phenotype in urothelium of testicular feminized (Tfm/y) mice, *Journal of Steroid Biochemistry* 14:12:1317-1324 (Dec. 1981).
Cunha, et al., The possible influence of temporal factors in androgenic responsiveness of urogenital tissue recombinants from wild-type and androgen-insensitive (Tfm) mice, *Journal of Experimental Zoology* 205:2:181-193 (1978).
Day, et al., Rescue of embryonic epithelium reveals that the homozygous deletion of the retinoblastoma gene confers growth factor independence and immortality but does not influence epithelial differentiation or tissue morphogenesis, *The Journal of Biological Chemistry* 277:46:44475-44484 (Nov. 15, 2002).
Enguita-German, et al., CD133+ cells from medulloblastoma and PNET cell lines are more resistant to cyclopamine inhibition of the sonic hedgehog signaling pathway than CD133- cells, *Tumor Biology* 31:5:381-390 (Oct. 2010).
Garraway, et al., Human prostate sphere-forming cells represent a subset of basal epithelial cells capable of glandular regeneration in vivo, *Prostate* 70:5:491-501 (Apr. 2010).

(Continued)

*Primary Examiner* — Samira Jean-Louis
(74) *Attorney, Agent, or Firm* — Kilpatrick Townsend & Stockton, LLP

(57) ABSTRACT

Disclosed herein are methods and compositions for reducing the recurrence of prostate cancer and for treating prostate cancer.

20 Claims, 47 Drawing Sheets

(56) References Cited

OTHER PUBLICATIONS

Garraway, et al., Intermediate basal cells of the prostate: in vitro and in vivo characterization, *Prostate* 55:3:206-218 (2003).
Goldstein, et al., Identification of a Cell of Origin for Human Prostate Cancer, *Science* 329:5991:568-571 (Jul. 30, 2010).
Haringman, et al., A randomized controlled trial with an anti-CCL2 (anti-monocyte chemotactic protein 1) monoclonal antibody in patients with rheumatoid arthritis, *Arthritis & Rheumatism* 54:8:2387-2392 (Aug. 2006).
Hartsock, et al., Adherens and tight junctions: structure, function and connections to the actin cytoskeleton, *Biochimica et Biophysica Acta* 1778:3:660-669 (Mar. 2008).
Hayward, et al., Epithelial development in the rat ventral prostate, anterior prostate and seminal vesicle, *Acta Anat (Basel)* 155:2:81-93 (1996).
Heer, et al., The role of androgen in determining differentiation and regulation of androgen receptor expression in the human prostatic epithelium transient amplifying population, *Journal of Cellular Physiology* 212:3:572-578 (2007).
Huang, et al., Regulation of stromal proliferation, growth arrest, differentiation and apoptosis in benign prostatic hyperplasia by TGF-beta, *Frontiers in Bioscience* 8:s740-s749 (2003).
Huggins, et al., Studies on prostatic cancer. I. The effect of castration, of estrogen and androgen injection on serum phosphatases in metastatic carcinoma of the prostate, *CA: A Cancer Journal for Clinicians* 22:232-240 (1972).
Jackson, et al., Single-dose and steady-state pharmacokinetic studies of S-equol, a potent nonhormonal, estrogen receptor beta-agonist being developed for the treatment of menopausal symptoms, *Ausio Pharmaceuticals* 18:2:185-193 (2011).
Jarrard, et al., Methylation of the androgen receptor promoter CpG island is associated with loss of androgen receptor expression in prostate cancer cells, *Cancer Research* 58:23:5310-5314 (Dec. 1998).
Jiang, et al., Disruption of PPARgamma signaling results in mouse prostatic intraepithelial neoplasia involving active autophagy, *Cell Death & Differentiation* 17:3:469-481 (2010).
Johnson, et al., Isolation and characterization of mouse probasin: An androgen-regulated protein specifically expressed in the differentiated prostate, *Prostate* 43:4:255-262 (2000).
Kageyama, et al., the androgen receptor as putative therapeutic target in hormone-refractory prostate cancer, *Recent Patents on Anti-Cancer Drug Discovery* 2:3:203-211 (2007).
Kassen, et al., Stromal cells of the human prostate: initial isolation and characterization, *Prostate* 8:89-97 (1996).
Kim, et al., Expression and localization of transforming growth factor-beta receptors type I and type II in the rat ventral prostate during regression, *Molecular Endocrinology* 10:107-115 (1996).
Kim, et al., Loss of expression of transforming growth factor beta type I and type II receptors correlates with tumor grade in human prostate cancer tissues, *Clinical Cancer Research* 2:8:1255-1261 (1996).
Klingler, et al., Regulation of prostatic stromal cell growth and function by transforming growth factor beta (TGFbeta), *Prostate* 41:2:110-120 (1999).
Klisovic, et al., A phase I biological study of MG98, an oligodeoxynucleotide antisense to DNA methyltransferase 1, in patients with high-risk myelodysplasia and acute myeloid leukemia, *Clinical Cancer Research* 14: 8:2444-2449 (2008).
Koster, et al., p63 is the molecular switch for initiation of an epithelial stratification program, *Genes & Development* 18:2:126-131 (2004).
Lai, et al., Monocyte/macrophage androgen receptor suppresses cutaneous wound healing in mice by enhancing local TNF-alpha expression, *The Journal of Clinical Investigation* 119:12:3739-3751 (Dec. 1, 2009).
Lawson, et al., Basal epithelial stem cells are efficient targets for prostate cancer initiation, *Proceedings of the National Academy of Sciences of the United States of America* 107:6:2610-2615 (2010).
Lee, et al., New therapy targeting differential androgen receptor signaling in prostate cancer stem/progenitor vs. non-stem/progenitor cells, *Journal of Molecular Cell Biology* 5:1:14-26 (Feb. 2013).
Lee, et al., Suppressor role of androgen receptor in proliferation of prostate basal epithelial and progenitor cells, *Journal of Endocrinology* 213:2:173-182 (May 2012).
Leong, et al., Generation of a prostate from a single adult stem cell, *Nature* 456:7223:804-808 (Dec. 11, 2008).
Litvinov, et al., Is the Achilles' Heel for Prostate Cancer Therapy a Gain of Function in Androgen Receptor Signaling?, *The Journal of Clinical Endocrinology & Metabolism* 88:7:2972-2982 (2003).
Liu, et al., Correlated alterations in prostate basal cell layer and basement membrane, *International Journal of Biological Sciences* 5:3:276-285 (2009).
Liu, et al., Androgen receptor CpG island methylation status in human leukemia cancer cells, *Cancer Investestigation* 27:156-162 (2009).
Luk, et al., Gamma-tocotrienol as an effective agent in targeting prostate cancer stem cell-like population, *International Journal of Cancer* 128:9:2182-2191 (2010).
Ma, et al., Androgen receptor is a new potential therapeutic target for the treatment of hepatocellular carcinoma, *Gastroenterology* 135:3:947-955 (Sep. 2008).
Malamas, et al., Design and synthesis of aryl diphenolic azoles as potent and selective estrogen receptor-beta ligands, *Journal of Medicinal Chemistry* 47:21:5021-5040 (2004).
Miyamoto, et al., Promotion of bladder cancer development and progression by androgen receptor signals, *Journal of the National Cancer Institute* 99:7:558-568 (Apr. 4, 2007).
Mori, et al., Increased expression of genes for basic fibroblast growth factor and transforming growth factor type beta2 in human benign prostatic hyperplasia, *Prostate* 16:1:71-80 (1990).
Nishiyama, et al., The change in the dihydrotestosterone level in the prostate before and after androgen deprivation therapy in connection with prostate cancer aggressiveness using the Gleason score, *The Journal of Urology* 178:4:1282-1288 (2007).
Niu, et al., Androgen receptor is a tumor suppressor and proliferator in prostate cancer, *Proceedings of the National Academy of Sciences of the United States of America* 105:34:12182-12187 (Aug. 26, 2008).
Niu, et al., Differential androgen receptor signals in different cells explain why androgen-deprivation therapy of prostate cancer fails, *Oncogene* 29:25:3593-3604 (Jun. 24, 2010).
Niu, et al., Increased CK5/CK8-positive intermediate cells with stromal smooth muscle cell atrophy in the mice lacking prostate epithelial androgen receptor, *PLoS One* 6:7:e20202 (2011).
Niu, et al., Proliferation and differentiation of prostate stromal cells, *BJU International* 87:4:386-393 (2001).
Niu, et al., Targeting the stromal androgen receptor in primary prostate tumors at earlier stages, *Proceedings of the National Academy of Sciences of the United States of America* 105:34:12188-12193 (Aug. 26, 2008).
Patrawala, et al., Hierarchical organization of prostate cancer cells in xenograft tumors: the CD44+alpha2beta1+ cell population is enriched in tumor-initiating cells, *Cancer Research* 67:14:6796-6805 (Jul. 15, 2007).
Patrawala, et al., Side population is enriched in tumorigenic, stem-like cancer cells, whereas ABCG2+ and ABCG2- cancer cells are similarly tumorigenic, *Cancer Research* 65:14:6207-6219 (Jul. 16, 2005).
Peehl, et al., Induction of smooth muscle cell phenotype in cultured human prostatic stromal cells, *Experimental Cell Research* 232:2:208-215 (May 1, 1997).
Prins, et al., Androgen receptor localization in different cell types of the adult rat prostate, *Endocrinology* 129:6:3187-3199 (1991).
Reya, et al., Stem cells, cancer, and cancer stem cells, *Nature* 414:6869:105-111 (2001).
Robinson, et al., Basal cells are progenitors of luminal cells in primary cultures of differentiating human prostatic epithelium, *Prostate* 37:3:149-160 (1998).

(56) References Cited

OTHER PUBLICATIONS

Schayek, et al., Progression to metastatic stage in a cellular model of prostate cancer is associated with methylation of the androgen receptor gene and transcriptional suppression of the insulin-like growth factor-I receptor gene, *Experimental Cell Research* 316:9:1479-1488 (May 15, 2010).
Shi, et al., Novel anti-prostate cnacer curcumin analogues that enhance androgen receptor degradation activity, *Anti-Cancer Agents in Medicinal Chemistry* 9:8:904-912 (2009).
Singh, et al., Combinatorial androgen receptor targeted therapy for prostate cancer, *Endocrine-Related Cancer* 13:3:653-666 (2006).
Soriano, P., Generalized IacZ expression with the ROSA26 Cre reporter strain, *Nature Genetics* 21:1:70-71 (1999).
Stein, et al., Mitomycin C may inhibit mitosis by reducing G2 RNA synthesis, *Currents in Modern Biology* 2:254-263 (1968).
Story, et al., Influence of transforming growth factor beta1 and other growth factors on basic fibroblast growth factor level and proliferation of cultured human prostate-derived fibroblasts, *Prostate* 22:3:183-197 (1993).
Stovall, et al., MF-101, an estrogen receptor beta agonist for the treatment of vasomotor symptoms in peri- and postmenopausal women, *Current Opinion in Investigational Drugs* 19:4:365-371 (Apr. 2009).
Tang, et al., Androgen deprivation and stem cell markers in prostate cancers, *International Journal of Clinical and Experimental Pathology* 3:2:128-138 (2009).
Tang, et al., Prostate cancer stem/progenitor cells: identification, characterization, and implications, *Molecular Carcinogenesis* 46:1:1-14 (Jan. 2007).
Taylor, et al., The path toward identifying prostatic stem cells, *Differentiation* 76:6:671-681 (2008).
Thibault, et al., A phase II study of 5-aza-neoxycytidine (decitabine) in hormone independent metastatic (D2) prostate cancer, *Tumori* 84:1:87-89 (1998).
Titus, et al., Steroid 5alpha-reductase isozymes I and II in recurrent prostate cancer, *Clinical Cancer Research* 11:4365-4371 (2005).
Titus, et al., Testosterone and dihydrotestosterone tissue levels in recurrent prostate cancer, *Clinical Cancer Research* 11:13:4653-4657 (2005).
Tran, et al., Prostate stem cell antigen is a marker of late intermediate prostate epithelial cells, *Molecular Cancer Research* 1:2:113-121 (2002).
Tsujimura, et al., Proximal location of mouse prostate epithelial stem cells: a model of prostatic homeostasis, *Journal of Cell Biology* 157:7:1257-1265 (2002).
Uzgare, et al., In vitro culturing and characteristics of transit amplifying epithelial cells from human prostate tissue, *Journal of Cellular Biochemistry* 91:1:196-205 (2004).
Valdespino, et al., Current perspectives in the treatment of advanced prostate cancer, *Medical Oncology* 24:3:273-286 (2007).
Van Der Kwast, et al., Androgen receptors in endocrine-therapy-resistant human prostate cancer, *International Journal of Cancer* 48:2:189-193 (1991).
Van Leenders, et al., Stem cell differentiation within the human prostate epithelium: implications for prostate carcinogenesis, *BJU International* vol. 88, Supp. 2:35-42 (Sep. 2001).
Vander Griend, et al., The role of CD133 in normal human prostate stem cells and malignant cancer-initiating cells, *Cancer Research* 68:23:9703-9711 (2008).
Verhagen, et al., Differential expression of keratins in the basal and luminal compartments of rat prostatic epithelium during degeneration and regeneration, *Prostate* 13:1:25-38 (1988).
Wang, et al., A luminal epithelial stem cell that is a cell of origin for prostate cancer, *Nature* 461:7263:495-500 (Sep. 24, 2009).
Wang, et al., Cell Differentiation Lineage in the Prostate, *Differentiation* 68:4-5:270-279 (2001).
Wang, et al., Pten deletion leads to the expansion of a prostatic stem/progenitor cell subpopulation and tumor initiation, *Proceedings of the National Academy of Sciences of the United States of America* 103:5:1480-1485 (Jan. 31, 2006).
Williams, et al., Reduced levels of transforming growth factor beta receptor type II in human prostate cancer: an immunohistochemical study, *Clinical Cancer Research* 2:4:635-640 (1996).
Wu, et al., Increased prostate cell proliferation and loss of cell differentiation in mice lacking prostate epithelial androgen receptor, *Proceedings of the National Academy of Sciences of the United States of America* 104:31:12679-12684 (2007).
Xin, et al., Self-renewal and multilineage differentiation in vitro from murine prostate stem cells, *Stem Cells* 25:11:2760-2769 (Nov. 2007).
Xin, et al., The Sca-1 cell surface marker enriches for a prostate-regenerating cell subpopulation that can initiate prostate tumorigenesis, *Proceedings of the National Academy of Sciences of the United States of America* 102:19:6942-6947 (2005).
Xue, et al., Cell kinetics of prostate exocrine and neuroendocrine epithelium and their differential interrelationship: new perspectives, *Prostate* Supp. 8:62-73 (1998).
Xue, et al., Identification of intermediate cell types by keratin expression in the developing human prostate, *Prostate* 34:4:292-301 (1998).
Yang, et al., ASC-J9 ameliorates spinal and bulbar muscular atrophy phenotype via degradation of androgen receptor, *Nature Medicine* 13:3:348-353 (2007).
Yeh, et al., Generation and characterization of androgen receptor knockout (ARKO) mice: an in vivo model for the study of androgen functions in selective tissues, *Proceedings of the National Academy of Sciences of the United States of America* 99:21:13498-13503 (2002).
Zhu, et al., TGF-beta signaling and androgen receptor status determine apoptotic cross-talk in human prostate cancer cells, *Prostate* 68:3:287-295 (2008).
International Application No. PCT/US2012/036347, International Preliminary Report on Patentability issued on Nov. 5, 2013, 5 pages.
International Application No. PCT/US2012/036347, International Search Report & Written Opinion issued on Sep. 13, 2012, 7 pages.

\* cited by examiner e.

f.

a.

b.

c.    d.

(D)

(E)

(D)

(E)

(F)

(G)

(C)

(D)

(E)

(F)

| Sample | CD133+ | CD133- |
|---|---|---|
| Vector, no DHT | 97.2% | 2.83% |
| AR, no DHT | 73.7% | 26.3% |
| Vector, with DHT (10 nM) | 96.2% | 3.73% | c.

h.

i.

METHODS FOR TREATING PROSTATE CANCER

This application claims the benefit of U.S. Provisional Application No. 61/482,066, filed May 3, 2011, which is hereby incorporated herein in its entirety.

BACKGROUND

There are several standard treatments for prostate cancer, including androgen deprivation therapy (ADT), but eventually many patients show signs of androgen-independent tumor progression for which few treatment options are currently available.

SUMMARY

Provided herein is a method of reducing the recurrence of prostate cancer in a subject, comprising administering to the subject an effective amount of an agent that inhibits proliferation of prostate basal epithelial cells, wherein the subject is at risk for recurrence of prostate cancer.

Further provided is a method of treating prostate cancer in a subject, comprising selecting a subject with prostate cancer, wherein the prostate cancer comprises $CK5^+$ basal epithelial cells and administering to the subject an effective amount of an agent that inhibits proliferation of prostate basal epithelial cells.

Also provided is a method of reducing prostate tumor progression in a subject, comprising administering to the subject an effective amount of an agent that inhibits proliferation of prostate basal epithelial cells, wherein the subject has a prostate tumor.

DESCRIPTION OF THE DRAWINGS

In FIG. 1a, IHC staining showed that the expression of AR was knocked out in the epithelium of the pes-ARKO prostate of 24 week old mice (upper panel, white arrows), without affecting the AR expression in the stroma (upper panel, black arrows). AR positive rate in the luminal and basal cells was counted (lower panel). In FIG. 1b, expression of probasin, whose secretion from the murine luminal epithelial cells is dependent on androgen action, was detected by IHC staining. The decrease of probasin expression (upper panel) and less positive expression (lower panel) indicated the loss of functional epithelium in the pes-ARKO epithelium. In FIG. 1c, double staining of TUNEL and CK8 demonstrated more apoptosis signals from the CK8+ luminal epithelial cells of the pes-ARKO mice than that of the wild type mice, apoptotic cell counts were shown in FIG. 1d. In FIG. 1e, decreased proliferation of cells from the CK8+ luminal epithelial cells of the pes-ARKO mice as compared to proliferation from that of the wild type mice was shown. In FIG. 1f, the loss of luminal epithelial cells of pes-ARKO mice was further confirmed by NKX3.1 staining, which is expressed only in luminal epithelial cells.

In FIG. 2a, BrdU IHC staining showed the increased proliferation in AR knockout epithelium of pes-ARKO mice compared with that in the Wt mice. In FIG. 2b) double staining BrdU with basal marker CK5 indicated that the increased proliferation of pes-ARKO epithelium was attributed to basal epithelial cells. In FIG. 2c), the proliferation, which was demonstrated by Ki67 expression in the panel p63+ epithelial cells, was also increased in pes-ARKO mice. In FIG. 2d) the difference in the proliferation rate between Wt and pes-ARKO mice was demonstrated. In the bar graph shown in FIG. 2e, apoptosis (shown by TUNEL) did not involve CK5+ basal cells in either Wt or pes-ARKO mice.

In FIG. 3a, the decreased expression of E-cadherin, which is the key molecule of cell-cell tight junction (dark color), in pes-ARKO mice indicated that the loss of luminal epithelium (demonstrated in FIG. 1) in pes-ARKO mice made the epithelium loose. In FIG. 3b, H&E staining showed that the lumen of the pes-ARKO mice became round and dilated. In FIG. 3c, using the branching micro-dissection technique, it was shown that the lumen of both ventral and dorsal prostate were enlarged, but had less branching, especially distal branching loss in the ventral prostate of the 24 week old pes-ARKO mice. In FIG. 3d there is a slight enlargement of the ventral prostate in the 24 week old pes-ARKO mice.

In FIG. 4a, the observation of thinner muscle layer surrounding the lumen of the pes-ARKO mice was indicated in H&E staining, and measured under the microscope in FIG. 4b. The average thickness of the smooth muscle layer in pes-ARKO mice was decreased from 7 nm to 3 nm (P<0.01) (shown in the lower panel of FIG. 4b). In FIG. 4c, using trichrome staining, the muscle layer of the pes-ARKO mice was thinner than that of the wild type mice. In FIG. 4d, using immunostaining of smooth muscle α-actin, it was shown that the circles around the lumen in the wild type samples, were lost or weak in the pes-ARKO samples. In FIG. 4e, by staining with smooth muscle marker, calponin, the thinner smooth layer around the pes-ARKO epithelium was also demonstrated.

In FIG. 5a, the expression of TGF-β1 was investigated by IHC staining. The decreased expression of TGF-β1 was found in pes-ARKO epithelium. In FIG. 5b, by double staining TGF-β1 and calponin, it was demonstrated that the loss of TGF-β1 expression in the epithelium of pes-ARKO mice was coincident with the thinner surrounding smooth muscle layer. In FIG. 5c, to evaluate the TGF-β1 effect on the differentiation of smooth muscle cells, the primary cultured human prostate stromal cells were treated with different doses of TGF-β1. The expression of smooth muscle α-actin, as shown in FIG. 5c and FIG. 5d, and calponin, as shown in FIG. 5e and FIG. 5f, were detected following treatment for 1 to 5 days. FIG. 5g shows a graph of the expression of MyoD, Myogenin, α-SMA and Calponin genes, which are involved in the maturation of smooth muscle cells, were investigated after 10 ng/ml TGF-β1 treatment.

FIG. 7a shows that proliferation of progenitor cells in the pes-ARKO-TRAMP mice was increased. The double staining of the progenitor marker p63 with the proliferation marker Ki67 indicated that the proliferation of progenitor cells in the pes-ARKO-TRAMP mice was increased, compared to Wt-TRAMP mice and castrated TRAMP mice. In FIG. 7b, CK5 and p63 double staining was utilized to show that the CK5+/p63+ progenitor population was increased in 12 weeks old pes-ARKO TRAMP prostate compared to same aged wild type TRAMP mice. In FIGS. 7c and 7d, increased progenitor/stem cell population in pes-ARKO TRAMP mice was shown, as indicated with Sca-1 (FIG. 7c) and CD133 expression (FIG. 7d) observed compared to wild type-TRAMP mice and castrated TRAMP mice using a flow cytometry method.

FIG. 8A shows a photomicrograph of AR expression in PDE cells. FIG. 8B shows flow cytometric analysis results using Sca-1 and CD49f antibodies. FIG. 8C shows immunofluorescence staining for CK5, CK8, p63, and AR expression. After incubation with appropriate antibody, cells were incubated with Alexa594 or 488 tagged secondary antibodies, and visualized by fluorescence microscopy. Insets are DAPI staining results. FIG. 8D shows qRT-PCR analysis results of AR mRNA expression. The mRNAs of human prostate cell lines LNCaP and PC3 were used as positive and negative controls, respectively. FIG. 8E shows Western blot analyses. Total cell extracts were obtained from mPrE cells and AR expression was analyzed. The cell extracts of LNCaP cells were used as positive control. FIG. 8F shows the results of MTT assays performed at two different DHT concentrations, 1 nM and 10 nM. FIG. 8G shows the results of a sphere formation assay. The mPrE cells were infected with vector/AR carrying lentivirus. Cells in medium were then mixed with Matrigel (1:1) and coated on the rim of the well of 24-well culture plate. After cell mixtures solidified, medium (1 ml) were added to the well for 2 wks of incubation. Spheres formed were counted and the pictures were taken. GFP signal in insets indicates successful infection of V/AR. FIG. 8H shows Ki67 IF staining results after manipulation of expression of V/AR into the cells. Cells were stained with Ki67 and a similar protocol was applied as in FIG. 8C. Insets represent DAPI staining.

FIG. 9A shows flow cytometric separation of stem population cells using antibodies of sca-1 and CD44. FIG. 9B shows double IF staining using antibodies of sca-1/CK5 indicated that sca-1 positive stem cells are CK5 positive and of basal epithelial origin. FIG. 9C shows double IF staining using antibodies of sca-1/AR indicating that sca-1 positive stem cells are not AR expressed. FIG. 9D shows the morphology of the cells and IHC staining of CK5. FIG. 9E shows IF staining of sca-1 and CD44 indicating that colonies grown on NIH3T3 feeder cell layer were sca-1 and CD44 positive stem cells. FIG. 9F shows the results of AR mRNA expressions by real time PCR. The cDNAs obtained from mRNAs of LNCaP cells were used as positive control. FIG. 9G shows Western blot analysis of AR expression. Total cell extracts of LNCaP cells were used as positive control. FIG. 9H shows colony growth of PSCs after infection with vector/AR carrying lentivirus. Right panel shows quantitation. FIG. 9I shows the results of a sphere formation assay of PSCs after infection with vector/AR carrying lentivirus. Right panel shows quantitation.

FIG. 10A shows the strategy for development of basal-ARKO mouse. Mice of mixed background (FVB/B6) were used. FIG. 10B shows the results of genotyping after development of basal-ARKO mice. In FIG. 10C β-gal activity was shown in CK5-cre mice crossed with ROSA26 mice. FIG. 10D shows the results of immunofluorescent staining of AR/p63 in VP tissues obtained from 4 wks old wild type and basal-ARKO mice. Arrows indicate double positively stained cells (AR/p63) and arrows in gray represent p63 positive cells. FIG. 10E shows a size comparison of AP, VP, and DLP prostate lobes. FIG. 10F shows serum testosterone levels of wild type and basal-ARKO mice (at 4, 6, 8, and 12 wks old). FIG. 10G is a histologic examination showing phenotypic differences in wild type and basal-ARKO mice at 4 and 6 weeks.

FIG. 11A shows CK5 immunofluorescent staining result of VPs of 4 wk old wild type and basal-ARKO mice. AR and p63 (basal cell marker) staining is shown. FIG. 11B shows the results of Ki67 staining of VPs of wildtype and basal-ARKO mice at 4 and 6 weeks. Quantitation is shown in the lower panel.

FIG. 12A shows the morphology of LifeLine-basal cells. FIG. 12C shows the results of flow cytometric analysis using Sca-1 and CD49f antibodies. FIG. 12B shows immunofluorescent staining for CK5, CK8, p63, and AR expression. After incubation with appropriate antibody, cells were incubated with Alexa594 or 488 tagged secondary antibodies, and visualized by fluorescent microscopy. Insets are DAPI staining results. FIG. 12D shows Western blot analyses. Total cell extracts were obtained from LifeLine-basal cells and AR expression was analyzed. The cell extracts of LNCaP cells were used as a positive control. FIG. 12E show the results of MTT assays performed at two different androgenic concentrations, 1 nM and 10 nM. FIG. 12F shows Ki67 IF staining results after manipulation of expression of V/AR into the cells. Cells were stained with Ki67 and similar protocol was applied as in FIG. 12B. Insets represent DAPI staining.

In FIG. 13A, CK5-cre/WTAR and CK5-cre/fAR mice were crossed with ROSA26R mice. β-gal activity was shown. FIG. 13B shows expression of differentiation markers, CK8, and Nkx3.1, examined by qRT-PCR, after infecting normal LifeLine-basal cells with AR/vector carrying lentivirus.

FIGS. 15a, 15b, and 15c are the results with cells isolated from the TRAMP mice tumor tissues and FIG. 15d is from the C4-2 xenografted tumor tissues. AR played a suppressive role in self-renewal of S/P cells.

FIG. 17a shows that CD133+ cells increase with extended Casodex treatment in LNCaP cells. FIG. 17b shows that S/P cells increase after castration in LNCaP and C4-2 xenograft mice. Tumor tissues were obtained before and 10, 20, and 30 days after castration. FIG. 17c shows that CD133+S/P cells increase in human patient tissues after ADT. The same individual tumor tissues, before and after ADT were examined FIG. 17D shows staining of CD133. The increase in $CD133^+$ cells after ADT was detected in all 7 patients examined.

FIG. 18a shows that the CD133+ cells of LNCaP cell line were converted to CD133− cells upon AR expression. FIG. 18b shows that AR expression drives cells to more differentiated cell status. FIGS. 18c-e show that the expression of the stem cell markers was also decreased upon forced expression of AR, but the expression of the differentiation markers was increased. FIGS. 18f and g shows that several signaling pathways including Akt, Erk, Wnt, and Stat3 were activated and higher expressions of bcl-2, c-myc, and p21 molecules were detected in LNCaP-S/P cells. FIG. 18e shows that this activation/higher expression was reversed when AR expression was forced back in the cells. FIG. 18h shows that proliferation was significantly inhibited upon transfection of siRNAs against bcl-2 and c-myc and treatment with an inhibitor of the Akt pathway. FIG. 18i shows that when constitutively active forms of Akt and bcl-2 are introduced back to the AR expressed cells, the inhibitory effect of cell growth was reversed, showing that the activation of Akt and high expression of bcl-2 are critical in their self-renewal/proliferation. The similar profiles of activation of signaling pathways in S/P cells were also observed in C4-2 and Celprogen PCSC cell line.

In FIG. 19a, activation of signaling molecules and higher expression of anti-apoptotic proteins were shown in S/P cells of LNCaP cell line. FIG. 19b shows that activation/higher expression of molecules shown in FIG. 19a were AR knockout mediated. The results show in FIGS. 19c and 19d confirmed the effect of these molecules on proliferation of S/P cells.

DETAILED DESCRIPTION

Figure 1:
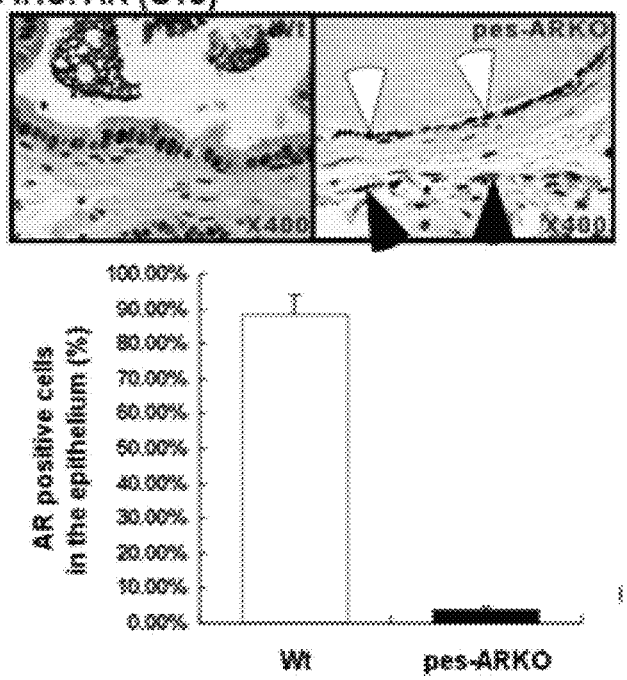
FIG. 1 shows that knockout of AR in the epithelium of mouse prostate led to the loss of functional luminal cells.
Figure 1:
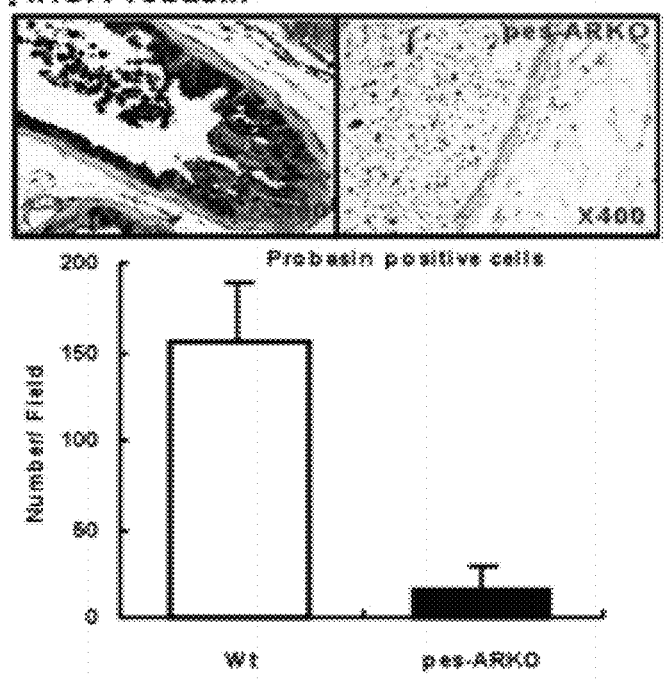
Figure 1:
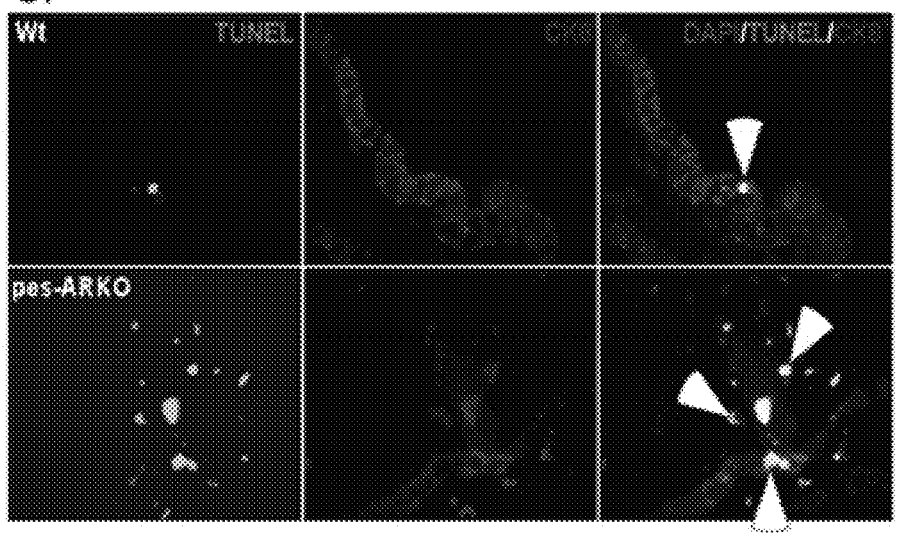
Figure 1:
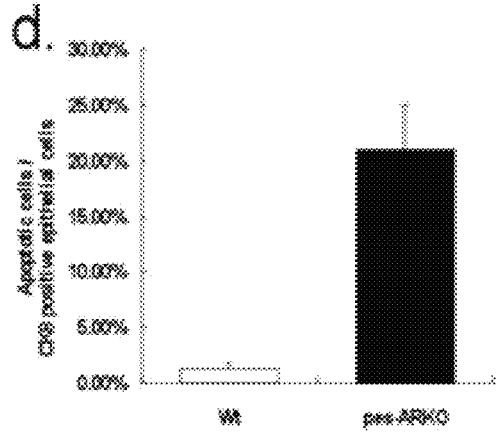
Figure 1:
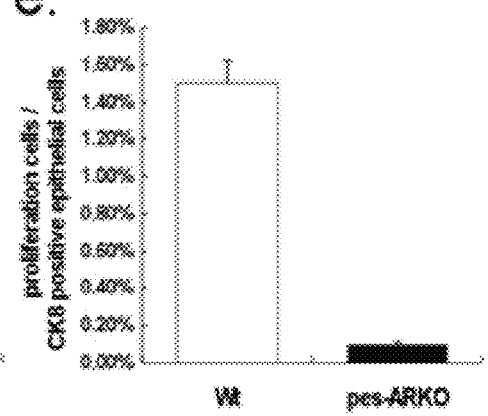
Figure 1:
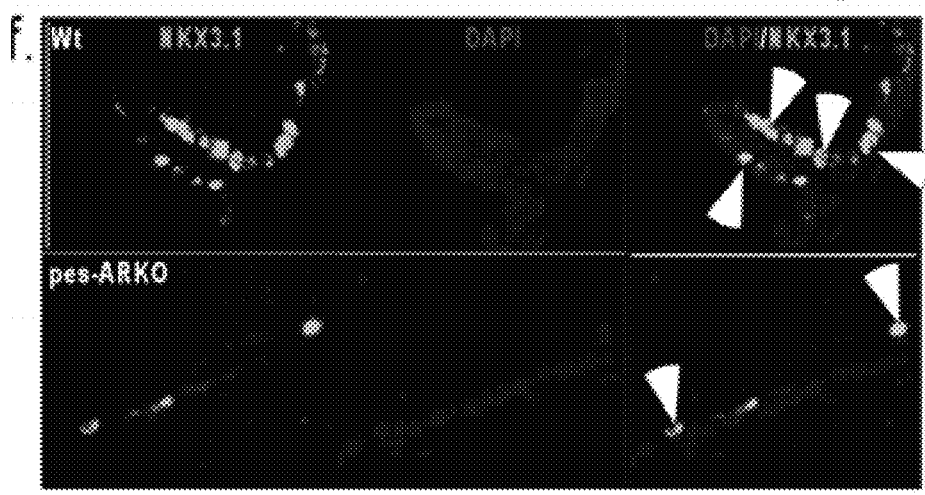

Described herein are methods and compositions related to treating or reducing the recurrence of prostate cancer. Provided herein is a method of reducing the recurrence of prostate cancer in a subject, comprising administering to the subject an effective amount of an agent that inhibits proliferation of prostate basal epithelial cells, wherein the subject is at risk for recurrence of prostate cancer.

Prostate cancer is a proliferative disorder characterized by abnormal cell growth that originates in the prostate gland. A proliferative disorder refers to any cellular disorder in which the cells proliferate more rapidly than normal tissue growth. A proliferative disorder includes, but is not limited to, neoplasms, which are also referred to as tumors. Prostate cancer tumors can be adenocarcinomas of epithelial origin. Prostate cancer tumors can comprise prostate luminal epithelial cells, prostate basal epithelial cells, stromal cells or a combination of prostate luminal epithelial, prostate basal epithelial cells or stromal cells. Prostate cancer tumors can comprise CK8+ prostate luminal epithelial cells. Prostate cancer tumors can also comprise CK5+ prostate basal epithelial cells which are also known as stem/progenital/basal epithelial cells As utilized herein, by reducing the recurrence of prostate cancer is meant a method of preventing, precluding, delaying, averting, obviating, forestalling, stopping, or hindering the onset, incidence or severity of the reappearance of prostate cancer in a subject. As utilized herein, by reappearance of prostate cancer is meant the reappearance of one or more clinical symptoms of prostate cancer after a period devoid of one or more clinical symptoms of prostate cancer. The recurrence of prostate cancer can be after treatment for prostate cancer or after a remission. A recurrence can occur days, weeks, months or years after treatment or after a remission. For example, the disclosed method is considered to reduce the occurrence of prostate cancer if there is a reduction or delay in onset, incidence or severity of the reappearance of prostate cancer, or one or more symptoms of prostate cancer (e.g., problems urinating, pain during urination, pelvic discomfort, swelling in the legs as a result of edema, blood in urine, swelling of the lymph glands, bone pain) in a subject at risk for a recurrence of prostate cancer compared to control subjects at risk for a recurrence of prostate cancer that did not receive an agent that inhibits proliferation of prostate basal epithelial cells. The disclosed method is also considered to reduce the recurrence of prostate cancer if there is a reduction or delay in onset, incidence or severity of the reappearance of prostate cancer, or one or more symptoms of prostate cancer (e.g., problems urinating, pain during urination, pelvic discomfort, swelling in the legs as a result of edema, blood in urine, swelling of the lymph glands, bone pain) in a subject at risk for recurrence of prostate cancer after receiving an agent that that inhibits proliferation of prostate basal epithelial cells as compared to the subject's progression prior to receiving treatment. Thus, the reduction or delay in onset, incidence or severity of recurrence of prostate cancer can be about a 10, 20, 30, 40, 50, 60, 70, 80, 90, 100%, or any amount of reduction in between.

As used throughout, by subject is meant an individual. Preferably, the subject is a mammal such as a primate, and, more preferably, a human. Non-human primates include marmosets, monkeys, chimpanzees, gorillas, orangutans, and gibbons, to name a few. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Veterinary uses and formulations for same are also contemplated herein.

A utilized herein, a subject at risk for recurrence of prostate cancer is a subject that is at risk for the reappearance of prostate cancer after treatment for prostate cancer or after remission from prostate cancer. Treatment methods for prostate cancer include, but are not limited to, orchiectomy (surgical castration), prostatectomy, anti-androgen therapy (for example, Eulexin®, Casodex®, Nilandron® and Nizoral®) radiation therapy, chemotherapy, luteinizing hormone releasing hormone analogs (for example, Lupron®, Viadur®, Eligard®, Zoladex®, Trelstar® and Vantas®), lutenizing hormone releasing hormone antagonists (for example, Plenaxis® and) Firmagon® or combinations of these treatment methods. One of skill in the art can determine if a subject is at risk for recurrence of prostate cancer. For example, after treatment, the subject can be monitored for recurrence of prostate cancer. Routine follow up visits after treatment allow one of skill in the art to determine if the subject is devoid of clinical symptoms or if clinical symptoms of prostate cancer have reappeared. In order to determine the status of the subject, a blood test to measure PSA levels can be performed. The results of the PSA test can indicate that prostate cancer can or has recurred. Imaging techniques, such as X-rays, MRIs, CT scans and bone scans can also be used. Lymph node examinations, biopsies, and digital rectal examinations can also be utilized to identify a subject at risk for recurrence of prostate cancer. These techniques can also be used to stage any recurrence of prostate cancer.

Also provided is a method of treating prostate cancer in a subject, comprising selecting a subject with prostate cancer, wherein the prostate cancer comprises CK5+ prostate basal epithelial cells and administering to the subject an effective amount of an agent that inhibits proliferation of prostate basal epithelial cells. As set forth in the Examples, androgen deprivation can lead to increased proliferation of a subset of epithelial cells, i.e. CK5+ prostate basal epithelial cells. Therefore, selecting subjects with prostate cancer, wherein the prostate cancer comprises CK5+ prostate basal epithelial cells allows one of skill in the art to specifically identify a cell type that does not respond well to anti-androgen therapy and administer an agent that decreases proliferation of CK5+ prostate basal epithelial cells. This can be done in combination with anti-androgen therapy that decreases proliferation of prostate luminal epithelial cells and/or stromal cells or independent of anti-androgen therapy. As set forth above, one of skill in the art would know how to identify a subject with prostate cancer. For example, a PSA test, imaging techniques (for example X-rays, MRIs, CT scans and bone scans), lymph node examinations, biopsies, and digital rectal examinations can be performed to identify or diagnose a subject with prostate cancer. One of skill in the art would also know how to characterize the prostate cancer as a prostate cancer comprising CK5+ prostate basal epithelial cells. For example, one of skill in the art could obtain a tissue sample from a prostate biopsy and perform immunohistochemical analysis to determine that the tissue sample comprises CK5+ prostate basal epithelial cells. The prostate cancer comprising CK5+ prostate basal epithelial cells can be the first incidence of prostate cancer in the subject or a recurrence of cancer in the subject.

Further provided is a method of reducing prostate tumor progression in a subject, comprising administering to the subject an effective amount of an agent that inhibits proliferation of prostate basal epithelial cells, wherein the subject has a prostate tumor. This method can be performed in combination with anti-androgen therapy that decreases proliferation of prostate luminal epithelial cells and/or stromal cells or independent of anti-androgen therapy.

As utilized herein, by reducing prostate tumor progression is meant a method of preventing, precluding, delaying, averting, obviating, forestalling, stopping, or hindering prostate tumor progression in a subject. The disclosed method is considered to reduce prostate tumor progression if there is a reduction or delay in prostate tumor growth, metastasis or one or more symptoms of prostate cancer (e.g., problems urinating, pain during urination, pelvic discomfort, swelling in the legs as a result of edema, blood in urine, swelling of the lymph glands, bone pain) in a subject with a prostate tumor as compared to control subjects with a prostate tumor that did not receive an agent that inhibits proliferation of prostate basal epithelial cells. The disclosed method is also considered to reduce prostate tumor progression if there is a reduction or delay in prostate tumor growth, metastasis or one or more symptoms of prostate cancer (e.g., problems urinating, pain during urination, pelvic discomfort, swelling in the legs as a result of edema, blood in urine, swelling of the lymph glands, bone pain) in a subject with a prostate tumor after receiving an agent that inhibits proliferation of prostate basal epithelial cells as compared to the subject's progression prior to receiving treatment. Thus, the reduction or delay prostate tumor can be about a 10, 20, 30, 40, 50, 60, 70, 80, 90, 100%, or any amount of reduction in between.

The methods set forth herein can be utilized to treat prostate cancer or reduce the recurrence of prostate cancer in a subject that has been treated with an anti-androgen or anti-androgen receptor agent that inhibits proliferation of prostate luminal epithelial cells, stromal cells or a combination of prostate luminal epithelial and stromal cells. Such agents include, but are not limited to Eulexin®, Casodex®, Nilandron® and Nizoral®. the anti-androgen agent can also be a curcumin analog, such ASC-J9 (see U.S. Pat. No. 7,355,081 herein incorporated in its entirety by this reference). Any of the curcumin analogs set forth in U.S. Pat. No. 7,355,081 that act as an anti-androgen can be utilized. For example, the anti-androgen can be a compound of formula I:

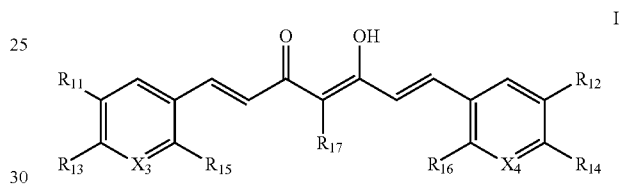

wherein $R_{11}$ and $R_{12}$ are each independently selected from the group consisting of alkoxy, nitro, amino, and dialkylamino;

$R_{13}$ and $R_{14}$ are each independently selected from the group consisting of hydroxy, alkoxy, $-OR_{18}C(O)R_{19}$, wherein $R_{18}$ is lower alkylene or alkenylene and $R_{19}$ is alkoxy, and tetrahydropyranyl[THP];

or $R_{11}$ and $R_{13}$ together are alkylenedioxy;

or $R_{12}$ and $R_{14}$ together are alkylenedioxy;

$R_{15}$ and $R_{16}$ are each independently selected from the group consisting of H, halogen, and nitro;

$R_{17}$ is $-R_{20}C(O)OR_{21}$ wherein $R_{20}$ is alkylene or alkenylene and $R_{21}$ is H or alkyl;

$X_3$ is N, or $X_3$ is C bonded to a H, alkoxy or nitro; and $X_4$ is N, or $X_4$ is C bonded to a H, alkoxy or nitro; or a pharmaceutically acceptable salt thereof. The compound of formula I can also be as described above, but subject to the proviso that $R_{20}$ is not alkylene when $R_{11}$, $R_{12}$, $R_{13}$ and $R_{14}$ are methoxy, and $X_3$ and $X_4$ are C bonded to a methoxy.

The term alkyl or lower alkyl as used herein refers to C1 to C4, C6 or C8 alkyl, which may be linear or branched and saturated or unsaturated. Cycloalkyl is specified as such herein, and is typically $C_3$, $C_4$ or C5 to C6 or C8 cycloalkyl. Alkenyl" or lower alkenyl as used herein likewise refers to C1 to C4 alkenyl, and alkoxy or lower alkoxy as used herein likewise refers to C1 to C4 alkoxy. Alkoxy as used herein refers to linear or branched, saturated or unsaturated oxo-hydrocarbon chains, including for example methoxy, ethoxy, propoxy, isopropoxy, butoxy, and t-butoxy. The term aryl as used herein refers to C3 to C10 cyclic aromatic groups such as phenyl, naphthyl, and the like, and includes substituted aryl groups such as tolyl. Halo as used herein refers to any halogen group, such as chloro, fluoro, bromo, or iodo. In some embodiments halo is preferably fluoro. The term hydroxyalkyl as used herein refers to C1 to C4 linear or branched hydroxy-substituted alkyl, i.e., —CH₂OH, —(CH₂)₂OH, etc. The term aminoalkyl as used herein refers to C1 to C4 linear or branched amino-substituted alkyl, wherein the term amino refers to the group NR'R", wherein R' and R" are independently selected from H or lower alkyl as defined above, i.e., —NH₂, —NHCH₃, —N(CH₃)₂, etc. The term "tetrahydropyranyl" refers to a group of the formula:

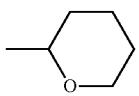

The term "oxyalkyl" as used herein refers to C1 to C4 oxygen-substituted alkyl, i.e., —OCH₃, and the term "oxyaryl" as used herein refers to C3 to C10 oxygen-substituted cyclic aromatic groups. The term "alkylenedioxy" refers to a group of the general formula —ORNO—, —ORNORN—, or —RNORNORN— where each RN is independently alkyl.

The anti-androgen can also be a compound according to formula I having the structure:

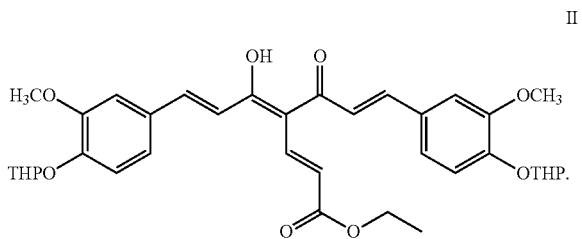

II

The anti-androgen can also be a compound according to formula I having the structure:

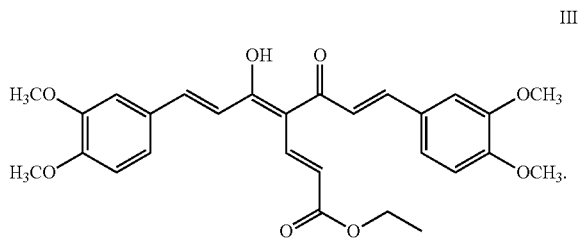 [SMILES: CCOC(=O)/C=C/C(C(=O)/C=C/c1ccc(OC)c(OC)c1)=C(O)\C=C\c1ccc(OC)c(OC)c1]

III

In the methods set forth herein, two or more anti-androgens can be administered to the subject. The subject can be treated with the anti-androgen agent prior to, concurrently with, or after administration of an agent that inhibits proliferation of prostate basal epithelial cells. In the methods set forth herein, two or more anti-androgens can be administered to the subject.

In the methods set forth herein, the agent that inhibits proliferation of prostate basal epithelial cells can be a chemical, a small or large molecule (organic or inorganic), a drug, a protein, a peptide, a cDNA, an antibody, an aptamer, a morpholino, a triple helix molecule, an siRNA, a shRNA, an miRNA, an antisense RNA, a ribozyme or any other compound now known or identified in the future that inhibits proliferation of basal epithelial cells.

The agent that inhibits proliferation of prostate basal epithelial cells can also be selected from a group consisting of an estrogen receptor β agonist, a methylation agent and an AKT inhibitor. For example, the agent that inhibits proliferation of prostate basal epithelial cells can be an estrogen receptor β agonist. Examples of estrogen receptor β agonists include, but are not limited to, ERB-041 (see Malamas et al., "Design and synthesis of aryl diphenolic azoles as potent and selective estrogen receptor-beta ligands," *J. Med Chem.* 47(21): 5021-40.), Vitamin E (for example, tocopherol or tocotrienol derivatives, such as alpha tocotrienol, beta tocotrienol and gamma-tocotrienol), MF-101 (see Stoval and Pinkerton, "MF-101, an estrogen receptor beta agonist for the treatment of vasomotor symptoms in peri- and post-menopausal women," *Curr. Opin. Investig. Drugs* 19(4): 365-71(2009)), benzopyrans (for example, SERBA-1), a phytoestrogen, diarylpropiolnitrile (DPN), 17β-estradiol, 7α-hydroxy-DHEA, WAY-202196 (see Cristofaro et al. "WAY-202196, a selective estrogen receptor beta agonist, protects against death in experimental septic shock," *Critical Care Medicine* 34(8): 2188-2193 (2006)) and AUS-131 from Ausio Pharmaceuticals (see Jackson et al. "Single-dose and steady-state pharmacokinetic studies of S-equol, a potent nonhormonal, estrogen receptor β-agonist being developed for the treatment of menopausal symptoms," 18(2): 185-193 (2011)).

An agent that inhibits proliferation of prostate basal epithelial cells can also be a methylation agent, for example, a DNA methylation inhibitor. Examples of DNA methylation inhibitors include DNA methyltransferase inhibitors. Examples of DNA methyltransferase inhibitors include, but are not limited to 5-Aza-cytidine (azacitidine), 5-aza-2'deoxycytidine (decitabine), 2'-deoxycytidine, arabinosylcytosine, arabinosyl-5-azacytosine (fazarabine), dihydro-5-azacytidine (DHAX) and MG98. MG98 is an antisense oligodeoxynucleotide directed against the 3' untranslated region of the DNA methyltransferase-1 enzyme mRNA (see Klisovic et al. "A Phase I Biological Study of MG98, an Oligonucleotide Antisense to DNA Methyltransferase 1, in Patients with High-Risk Myelodysplasia and Acute Myeloid Leukemia," *Clin. Cancer Res.* 14: 2444 (2008).

An agent that inhibits proliferation of prostate basal epithelial cells can also be an AKT pathway inhibitor, for example, and not to be limiting, LY294002, wortmannin, or PCK412. AKT pathway inhibitors include, but are not limited to, inhibitors of PI3K, AKT and/or MTOR.

In the present methods, two or more agents that inhibit proliferation of prostate basal epithelial cells can be administered to the subject. As set forth above, these agents can be selected from the group consisting of an estrogen receptor β agonist, an AKT inhibitor and a methylation agent. For example, and not to be limiting, an estrogen receptor β agonist and an AKT inhibitor can be administered; an estrogen receptor β agonist and a methylation agent can be administered; an estrogen receptor β agonist, a methylation agent and an AKT inhibitor can be administered or an AKT inhibitor and a methylation agent can be administered; two or more estrogen receptor β agonist can be administered; two or more AKT inhibitors can be administered; or two or more methylation agents can be administered. For example, gamma-tocotrienol and LYS294002 can be administered to the subject; gamma-tocotrienol, LYS294002 and decitabine can be administered to the subject; LYS294002 and decitabine can be administered to the subject or any combination of two or more agents selected from the group consisting of an estrogen receptor β agonist, an AKT inhibitor and a methylation agent can be administered to the subject. When two or more agents that inhibit proliferation of prostate basal epithelial cells are administered, one or more agents that inhibit proliferation of prostate basal epithelial cells can be administered prior to, concurrently with or after administration of one or more different agents that inhibit proliferation of prostate basal epithelial cells. For example, and not to be limiting, if gamma-tocotrienol, LYS294002 and decitabine are administered, gamma-tocotrienol can be administered first, followed by administration of LYS294002 and decitabine; gamma-tocotrienol can be administered concurrently with LYS294002; and decitabine or gamma-tocotrienol can be administered after administration of LYS294002 and decitabine. As mentioned above, this is merely exemplary as one of skill in the art would know when to administer the agents set forth herein.

As mentioned above, an agent that inhibits proliferation of prostate basal epithelial cells can be administered to a subject that has been treated with an anti-androgen or anti-androgen receptor agent that inhibits proliferation of prostate luminal epithelial cells, stromal cells or a combination of prostate luminal epithelial and stromal cells. Such agents include, but are not limited to Eulexin®, Casodex®, Nilandron® Nizoral® and ASC-J9 (see U.S. Pat. No. 7,355,081 herein incorporated in its entirety by this reference). Therefore, in the methods set forth herein, one or more agents that inhibit proliferation of prostate basal epithelial cells can be administered to a subject prior to, concurrently with, or after administration of an anti-androgen agent. Therefore, one or more agents selected from the group consisting of an estrogen receptor 13 agonist, an AKT inhibitor and a methylation agent can be administered to a subject, prior to, concurrently with, or after administration of an anti-androgen agent. For example, one or more agents selected from the group consisting of an estrogen receptor β agonist, an AKT inhibitor and a methylation agent can be administered to a subject, prior to, concurrently with, or after administration of an anti-androgen agent selected from the group consisting of Eulexin®, Casodex®, Nilandron® Nizoral® and ASC-J9. For example, and not to be limiting, two or more agents selected from the group consisting of gamma-tocotrienol, LYS294002, azacitidine and decitabine can be administered to a subject, prior to, concurrently with, or after administration of ASC-J9. In another example, two or more agents selected from the group consisting of gamma-tocotrienol, LYS294002 and azacitidine can be administered to a subject, prior to, concurrently with, or after administration of ASC-J9. In yet another example, two or more agents selected from the group consisting of gamma-tocotrienol, LYS294002 and decitabine can be administered to a subject, prior to, concurrently with, or after administration of ASC-J9.

Any of the methods set forth herein, can further comprise administering an anti-inflammatory agent to the subject. Examples of anti-inflammatory agents include, but are not limited to anti-monocyte chemotactic protein 1 (anti-CCL2) monoclonal antibody, anti-CCL3 monoclonal antibody and anti-CCL4 monoclonal antibody, ImSAIDs, NSAIDS and steroids.

The agents described herein can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the agent described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected agent without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the agent(s) described herein suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Administration can be carried out using therapeutically effective amounts of the agents described herein for periods of time effective to treat or reduce recurrence of prostate cancer The effective amount may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day.

According to the methods taught herein, the subject is administered an effective amount of the agent. The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the activity of the specific compound employed, the metabolic stability and length of action of that compound, the species, age, body weight, general health, sex and diet of the subject, the mode and time of administration, rate of excretion, drug combination, and severity of the particular condition and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

Any appropriate route of administration may be employed, for example, parenteral, intravenous, subcutaneous, intramuscular, intraventricular, intracorporeal, intraperitoneal, rectal, or oral administration. Administration can be systemic or local. Pharmaceutical compositions can be delivered locally to the area in need of treatment, for example by topical application or local injection. Multiple administrations and/or dosages can also be used. Effective doses can be extrapolated from dose-response curves derived from in vitro or animal model test systems.

The disclosure also provides a pharmaceutical pack or kit comprising one or more containers filled with one or more of the ingredients of the pharmaceutical compositions. Instructions for use of the composition can also be included.

In an example in which a nucleic acid is employed, such as an antisense or an siRNA molecule, the nucleic acid can be delivered intracellularly (for example by expression from a nucleic acid vector or by receptor-mediated mechanisms), or by an appropriate nucleic acid expression vector which is administered so that it becomes intracellular, for example by use of a retroviral vector (see U.S. Pat. No. 4,980,286), or by direct injection, or by use of microparticle bombardment (such as a gene gun; Biolistic, Dupont), or coating with lipids or cell-surface receptors or transfecting agents, or by administering it in linkage to a homeobox-like peptide which is known to enter the nucleus (for example Joliot et al., *Proc. Natl. Acad. Sci. USA* 1991, 88:1864-8). siRNA carriers also include, polyethylene glycol (PEG), PEG-liposomes, branched carriers composed of histidine and lysine (HK polymers), chitosan-thiamine pyrophosphate carriers, surfactants (for example, Survanta and Infasurf), nanochitosan carriers, and D5W solution. The present disclosure includes all forms of nucleic acid delivery, including synthetic oligos, naked DNA, plasmid and viral delivery, whether integrated into the genome or not.

Physical transduction techniques can also be used, such as liposome delivery and receptor-mediated and other endocytosis mechanisms (see, for example, Schwartzenberger et al., *Blood* 87:472-478, 1996) to name a few examples. These methods can be used in conjunction with any of these or other commonly used gene transfer methods.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

A number of embodiments have been described. Nevertheless, it will be understood that various modifications may be made. Accordingly, other embodiments are within the scope of the following claims.

EXAMPLES

Example 1

Using a cell specific knockout AR strategy, pes-ARKO mice with a knockout of AR only in the prostate epithelial cells were generated. It was demonstrated that epithelial AR can also play important roles in the development of the prostate gland. Mice lacking the prostate epithelial AR have increased apoptosis in epithelial CK8-positive luminal cells and increased proliferation in epithelial CK5-positive basal cells. The consequences of these two contrasting results leads to the expansion of CK5/CK8-positive intermediate cells, accompanied by stromal atrophy and impaired ductal morphogenesis. Molecular mechanism dissection found that an AR target gene, TGF-$\beta_1$, can play an important role in epithelial AR-to-stromal morphogenesis modulation. Furthermore, loss of epithelial AR could lead to the loss of the functional luminal cells, expanded progenitor cell population, impaired ductal morphogenesis, impaired smooth muscle differentiation, and decreased epithelium-derived TGF-$\beta_1$ expression. Together, these data suggest that epithelial AR can play important roles for the differentiation of prostate epithelium and the maturation of prostate stroma. Collectively, these results provide relevant information on how epithelial AR functions in epithelium-to-stromal interactions during the development of normal prostate. These results also show that AR can function as suppressor in selective cells within the prostate.

Cell Culture

Human prostate cancer cell lines were maintained in RPMI 1640 media with 10% fetal calf serum, 25 units/ml penicillin, and 25 µg/ml streptomycin.

Light Microscopy Procedures

Tissue samples were fixed in 5% neutral buffered formalin, embedded in paraffin, and cut into 5-µm thick slide sections. After H&E or immunostaining, the desired area was identified by light microscopy using a low power dry objective lens. A small drop of oil was placed on the coverslip for oil immersion lens high magnification and high resolution ($\times 1,000$) images of the area. The percentage of the positive cells were counted and the results were averaged from at least five different viewing areas.

Generation of Prostatic Epithelium Specific AR Knockout (Pes-ARKO) Mouse

To generate pes-ARKO mice, ARRPB2-Cre transgenic mice (C57BL/6) were mated with mice containing the conditional AR allele (floxed AR, C57BL/6). Probasin Cre (Pb-Cre) (C57BL/6) mice were obtained from NCI. The genotype of ARKO mice was confirmed by PCR screening using mouse tail snip DNA. The deletion of AR exon2 was further confirmed by RT-PCR amplifying AR mRNA from mouse prostate using exon1 and exon3 primers.

RNA Extraction, RT-PCR, and Real-Time RT-PCR

Tissues or cultured cells were harvested in TRIzol (Invitrogen, Grand Island, N.Y.) and total RNA was extracted following the manufacturer's instructions. 5 µg total RNA was reverse transcribed (RT) into 20 n1 cDNA by the SuperScript III kit (Invitrogen, Grand Island, N.Y.) with oligo(dT) primer. The 20 µl cDNA was then diluted by water to 200 µl. Two µl reverse transcribed cDNA were used for PCR and real-time quantitative PCR with the MyCycler thermal cycler (Bio-RAD) by Taq polymerase and on the iCycler IQ multicolor real-time PCR detection system with ⅕µl cDNA amplified by SYBR Green PCR Master Mix. Primers were designed using Beacon Designer 2 software and the β-actin expression level was used as a control to calculate the relative gene expression among different samples. Threshold (CT) values were calculated by subtracting the control CT value from the corresponding β-actin CT at each time point. The absence of nonspecific amplification products was confirmed by agarose-gel electrophoresis.

Immunohistochemistry

Samples were fixed in 5% neutral buffered formalin and embedded in paraffin. Primary antibodies of the rabbit anti-Ki67 (Abcam, Cambridge, Mass.), the rabbit anti-Tag (Santa Cruz Biotechnology, Inc., Santa Cruz, Calif.), the rabbit anti-AR (C19) (Santa Cruz Biotechnology, Inc., Santa Cruz, Calif.), anti-CK5 (Covance, Princeton, N.J.), anti-CK8 (Abcam, Cambridge, Mass.), anti-CD44 (Cell Signaling Technology, Danvers, Mass.), anti-TGFβ1 (Santa Cruz Biotechnology, Inc., Santa Cruz, Calif.), and anti-pSmad2/3 (Santa Cruz Biotechnology, Inc., Santa Cruz, Calif.) were used. The primary antibody was recognized by the biotinylated secondary antibody (Vector Laboratories, Burlingame, Calif.), and visualized by VECTASTAIN ABC peroxidase system (Vector Laboratories, Burlingame, Calif.) and peroxidase substrate DAB kit (Vector Laboratories, Burlingame, Calif.). The positive stainings were semi-quantitated by Image J software.

Immunofluorescence Staining of CK5 and CK8 in Mouse Prostate Tumors

Tissue sections were incubated overnight at 4° C. with primary antibodies, mouse anti-CK5 (Covance, Princeton, N.J.), and chicken anti-CK8 antibody (Abcam, Cambridge, Mass.). After a 60-min rinse (3×20 min, PBS 1% Triton-X 100), slides were incubated with secondary antibodies (donkey anti-chicken 596 Alexa Fluor dye and horse anti-mouse 488 Alexa Fluor dye) for 1 h at RT. Slides were then rinsed for 60 min (3×20 min), mounted with Vectashield Mounting Medium H1000 (Vector Laboratories, Burlingame, Calif.), and examined them on a fluorescence microscope (Leica Microsystems Inc., Buffalo Grove, Ill.).

BrdU Incorporation Assay

5'-Bromo-2'-deoxyuridine (BrdU) was purchased from Sigma (St. Louis, Mo.) and dissolved in double distilled water at 10 mg/ml. Starting at 24 hrs before sacrifice, mice were injected intraperitoneally every 6 hrs with 10 μg BrdU per gram body weight. Following harvest, tissues were embedded in paraffin and labeled following the BrdU Staining Kit (Zymed Laboratories Inc., Carlsbad, Calif.) manufacturer's instructions.

TUNEL Assay

Fluorescein-Frag EL™ DNA Fragmentation Detection Kit (CALBIOCHEM) was purchased. The paraffin-embedded tissue sections were labeled following the manufacturer's instructions, and the labeled nuclei were counted by using a standard fluorescein filter at 465-495 nm.

Statistics

The data were presented as the mean±standard deviation (SD). Comparisons were made between groups using a two-sided Student's t test. Differences with P values *P<0.05, P<0.01, *P<0.001 were considered significant.

The Prostate Decreased its Luminal Epithelial Cells and Secretion Function in Mice Lacking Epithelial AR Using flox-cre strategy, epithelial AR knockout mouse (pes-ARKO) were generated (see Wu et al., *Proc Natl Acad Sci USA*. 104:12679-84, 2007). These mice had a high efficiency of knockout AR (FIG. 1a). It was found that a pes-ARKO mouse lost its normal function of expressing and secreting probasin (FIG. 1b), an androgen-regulated protein specifically expressed in the differentiated prostate epithelial cells. Knockout of epithelial AR also led to increased apoptosis in the CK8+ luminal cells (FIG. 1c, 1d), as well as decreased proliferation in the CK8+ luminal cells (FIG. 1e). The expression of homeobox protein NKX3.1, which plays important roles in the maintenance of normal prostate morphogenesis, was also found to be decreased in the epithelium of pes-ARKO prostate (FIG. 1f).

Figure 2:
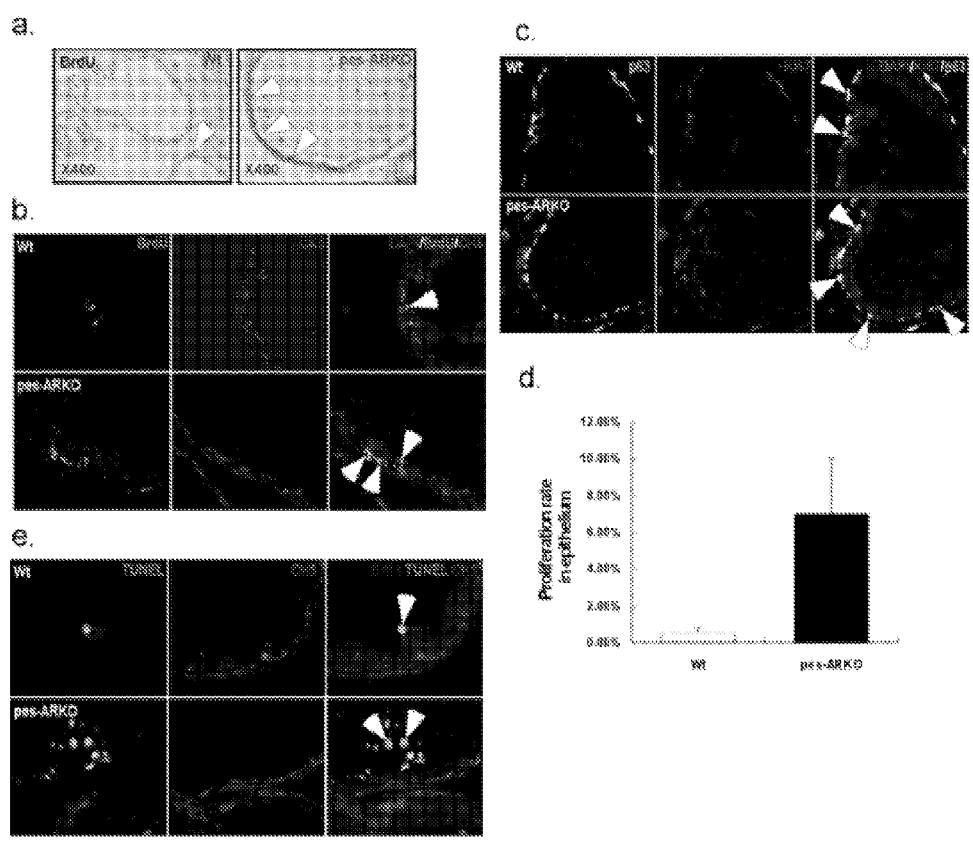
FIG. 2 shows that knockout of AR in the epithelium of mouse prostate induced the proliferation of basal progenitor cells.

Increased Proliferation in CK5+Basal Epithelial Cells in Mice Lacking Epithelial AR As shown in FIG. 1a, AR was also knocked out in the CK5+ basal epithelial cells, which include stem cells, progenitor cells and intermediate cells, even though only half of these basal cells in the wild type (Wt) prostate were AR+ stained. Interestingly, knockout of AR from these parts of the basal cells was sufficient to promote the proliferation of these cells (FIG. 2a, 2b, 2c, 2d). It was also found that higher proliferation signals were coincident with the higher expression of progenitor markers, p63 (FIG. 2c) and CD44, suggesting these increased proliferating cells may come from those stem/progenitor cells within CK5+ basal cells (FIG. 2b). Meanwhile, little apoptotic signal was found in the CK5+ basal cells of both Wt and pes-ARKO prostate (FIG. 2e).

Epithelial Cell Population Changes in Mice Lacking Epithelial AR

The increased apoptotic CK8+ luminal cells (FIG. 1) and increased proliferative CK5+ basal cells (FIG. 2) led to the expansion of CK5+/CK8+ intermediate cells in the epithelium. Interestingly, because these expanded cells are also both p63+ and CK5+, they may also be defined as expanded stem/progenitor cells in the epithelium.

Figure 3:
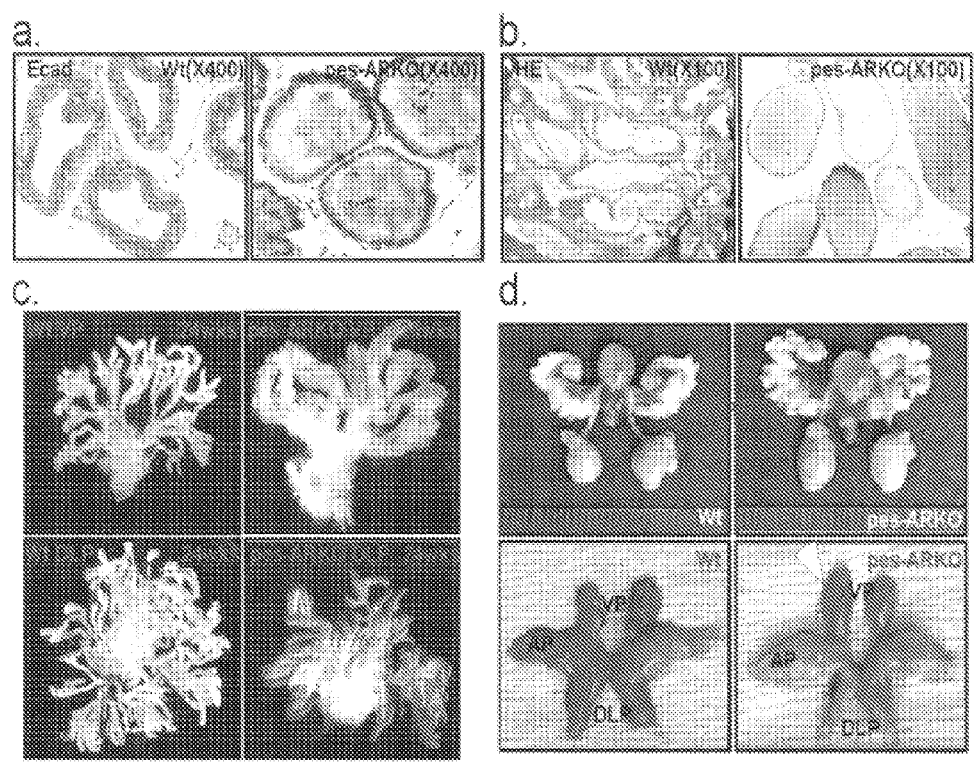
FIG. 3 shows that the immature epithelial cells of the pes-ARKO prostate are unable to form a normal ductal system.

Altered Ductal Morphogenesis with Decreased Ductal Branches in Mice Lacking Epithelial AR In addition to changes of cell population within epithelium, loss of epithelial AR resulted in decreased E-cadherin expression (FIG. 3a), which can lead to the damaged tight junction and barrier in the epithelium surface, leading to loose epithelium. Using H&E staining (FIG. 3b) and prostate micro-dissection for ductal morphogenesis (FIG. 3c), it was found that the prostate lumen of the pes-ARKO mice became round and dilated, with folding dismissed and less branch-points. Notably, at 24 weeks, the pes-ARKO ventral prostates (VPs) showed significantly decreased ductal branches and dilated lumen in VPs and dorsal-lateral prostates DLPs (FIG. 3c), and the size of VPs becomes larger as compared to those from Wt mice (FIG. 3d).

Figure 4:
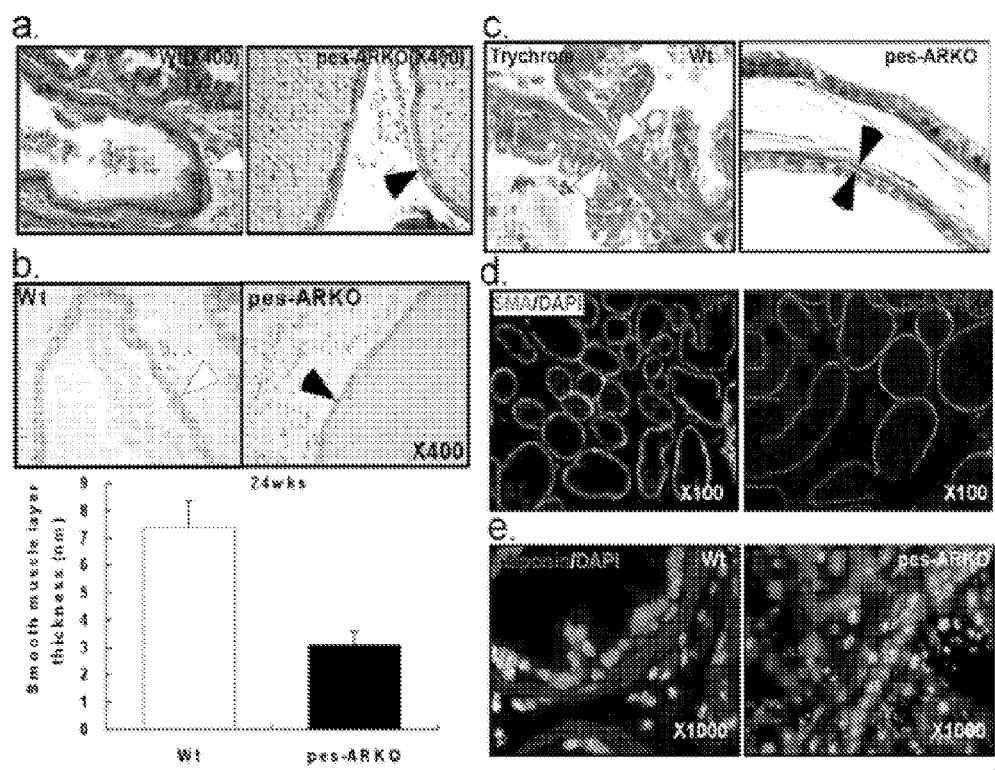
FIG. 4 shows that the thickness of the smooth muscle layer, which surrounds the lumen, is significantly thinner in the pes-ARKO prostate than that in the wild type prostate.

Thinner Wall of the Lumens with Impaired Stromal Smooth Muscle Differentiation in Mice Lacking Epithelial AR In addition to the dilated lumen, thinner stromal smooth muscle layer of VPs was also found in 24 week old pes-ARKO mice (FIGS. 4a and 4b). Using Trichrome staining, it was found that the lumen-surrounding stromal smooth muscle (FIG. 4c, between arrows) but not the collagen, was absent in the VPs of pes-ARKO mice. As expected, the mature stromal smooth muscle markers, smooth muscle α-actin (SMA) (FIG. 4d) and calponin (FIG. 4e) were significantly decreased in the VPs of 24 weeks pes-ARKO mice compared to wild type mice.

Decreased TGF-$β_1$ Signals in Mice Lacking Epithelial AR

Figure 5:
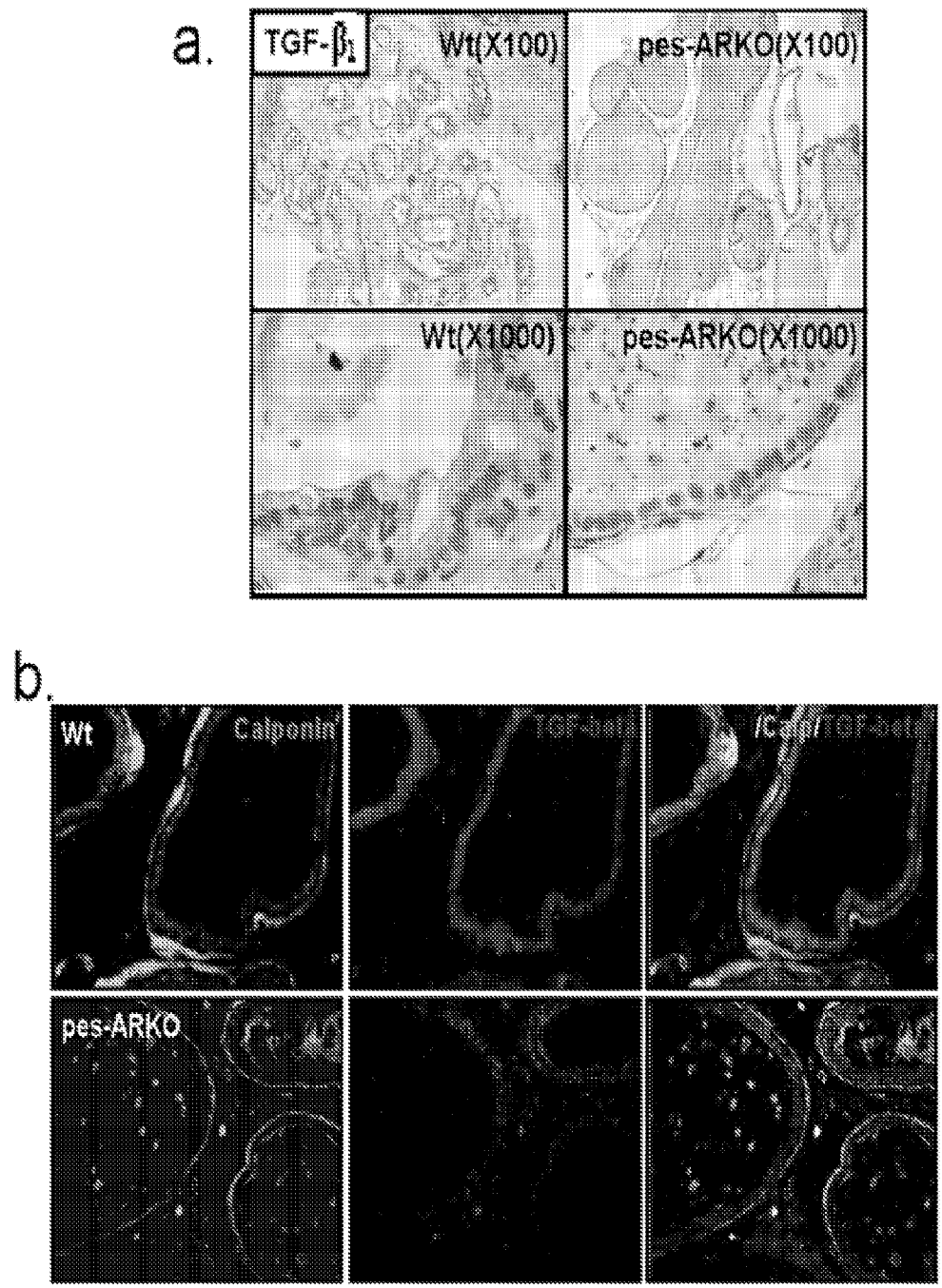
FIG. 5 shows that the reduction of the expression of TGF-β1 in the pes-ARKO prostate epithelium may cause the thin smooth muscle layer.
Figure 5:
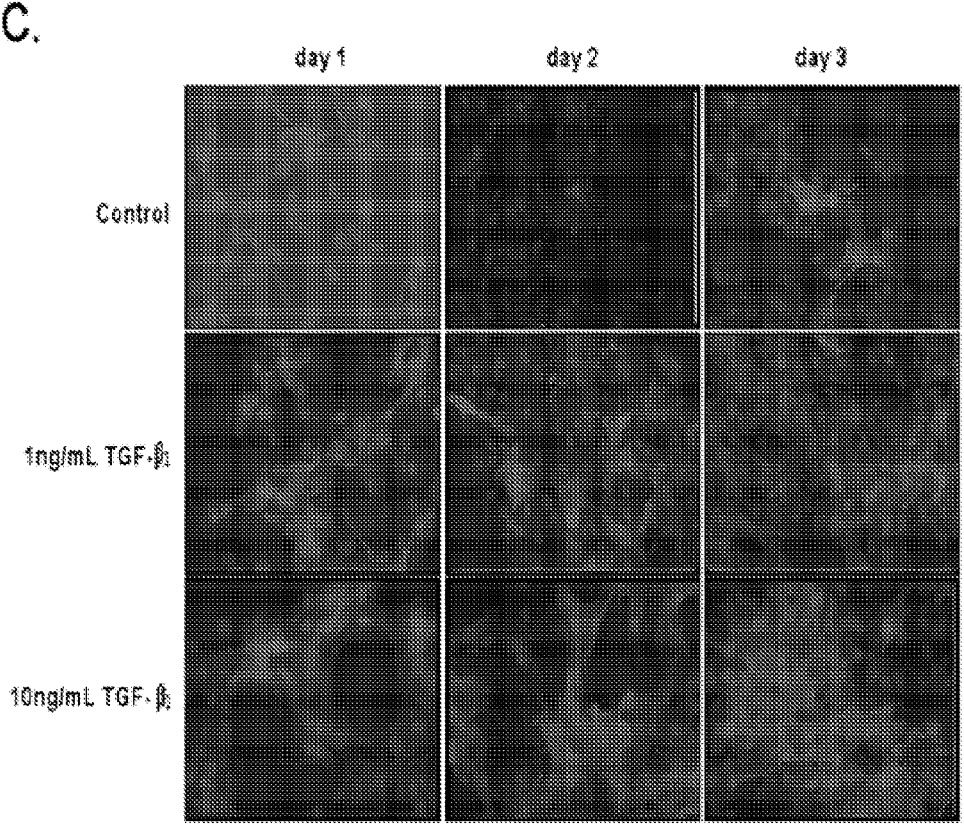
Figure 5:
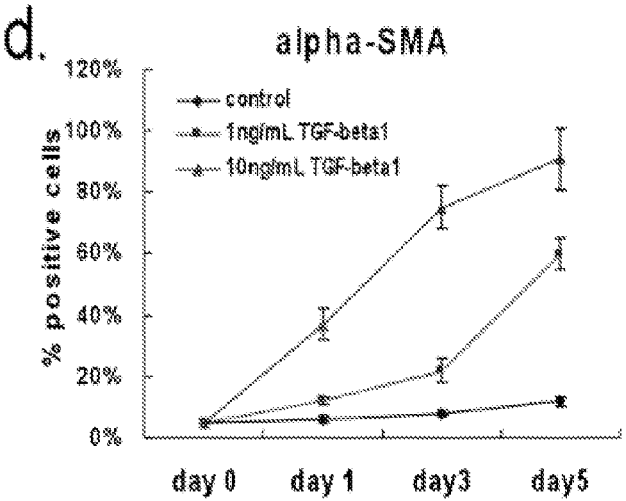
Figure 5:
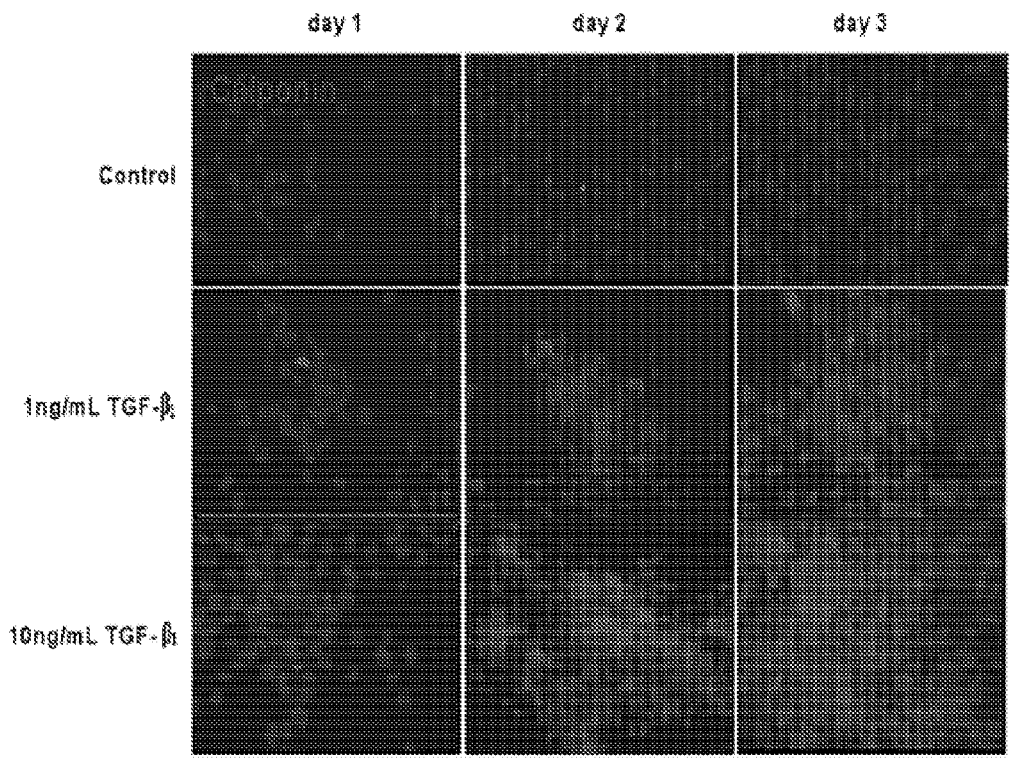
Figure 5:
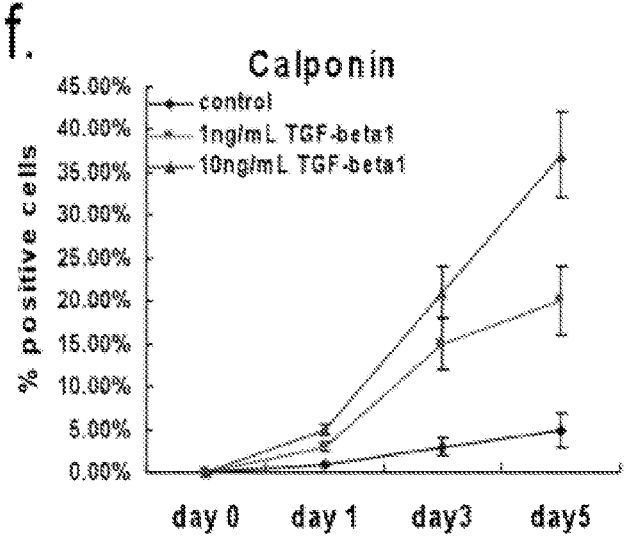
Figure 5:
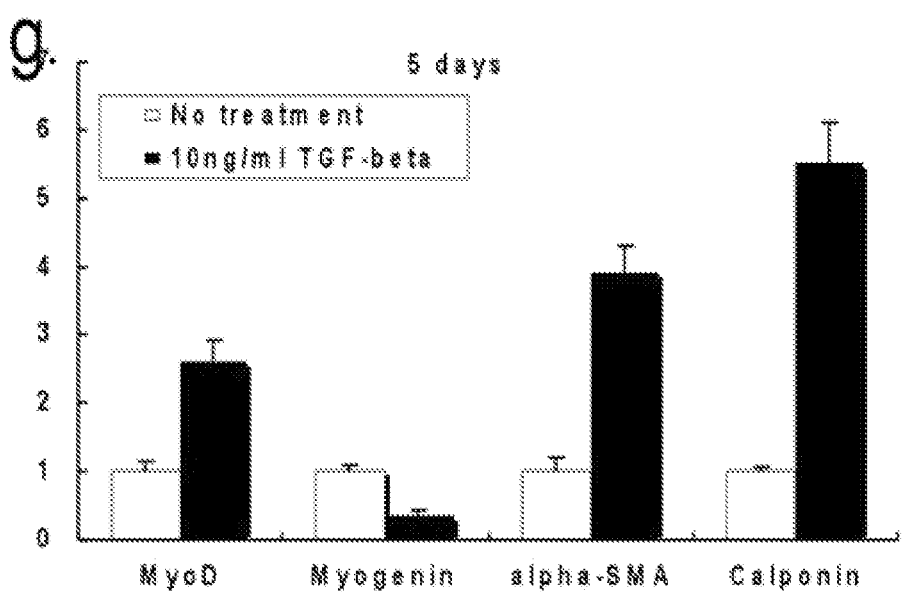

The expression of TGF-$β_1$ (FIG. 5a) and TGF-$β_1$ downstream signals was detected by immunohistochemistry (IHC) staining in 24 week old wild type and pes-ARKO prostate epithelium. The TGF-$β_1$ expression and its downstream signals were lower in the epithelium of pes-ARKO mice than those from wild type mice. By double staining TGF-$β_1$ and calponin, it was demonstrated that the loss of TGF-$β_1$ expression (FIG. 5b) in the epithelium of pes-ARKO mice could be coincident with the thinner layer of the surrounding stromal smooth muscle (FIG. 5b). Treating the primary cultured human stromal cells (ps-1) with different concentrations of TGF-$β_1$ for 1 to 5 days, both α-SMA and calponin staining showed that the number of mature stromal smooth muscle cells was significantly dependent on the higher concentration and longer duration of TGF-$β_1$ treatment (FIGS. 5c, 5d, 5e, and 5f). MyoD and Myogenin expression, which are deeply involved in the stromal smooth muscle maturation and differentiation, was also modulated by TGF-$β_1$ stimulation (FIG. 5g).

Altogether, impaired epithelial differentiation by knockout of epithelial AR could lead to poor stromal differentiation that could involve the modulation of TGF-$β_1$ signals.

Figure 6:
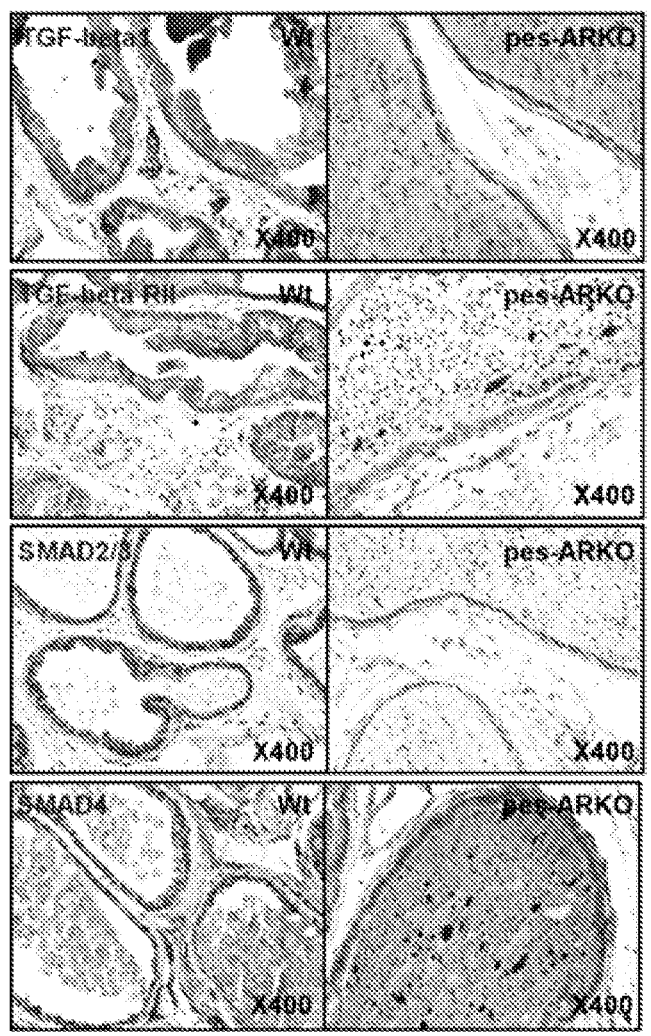
FIG. 6 shows that TGF-β1 signaling was decreased in the epithelium of pes-ARKO prostate.
Figure 6:
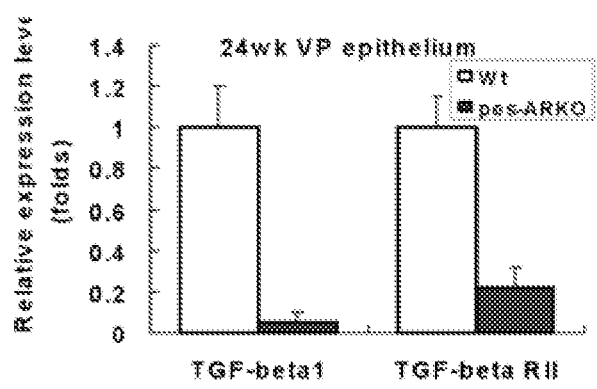

These data demonstrated that loss of epithelial AR led to altered epithelial cell proliferation, which in turn could also result in the poor differentiation of stromal smooth muscle cells. Furthermore, these data showed that the loss of TGF-$β_1$ expression (after knockout of epithelial AR) was coincident with the thinner layer of the surrounding smooth muscle, and the number of mature smooth muscle cells was dependent on the higher concentration and longer duration of TGF-$β_1$ treatment. FIG. 6 shows that TGF-β1 signaling was decreased in the epithelium of pes-ARKO prostate.

The increased apoptosis in epithelial CK8+ luminal cells and increased proliferation in epithelial CK5+ basal cells leads to the expansion of p63+/CK5+ progenitor populations and CK5+/CK8+ intermediate cells. These cell population changes confirm the existence of intermediate cells that are phenotypically intermediate between basal and luminal cells, and more importantly, as these intermediate cells are also p63+(a progenitor cell marker), it could also indicate that basal cells and luminal cells are hierarchically related. Basal cells may represent the progenitors of luminal cells. Since loss of epithelial AR resulted in impaired ductal morphogenesis and enlargement of the VP gland, this could also suggest that progenitor cells (and their original stem cells) could be responsible for tissue homeostasis of epithelial tissues with diverse architectural design and physiology. This further confirms that epithelial AR could not only be required for epithelial cell differentiation, but also function as a proliferation suppressor for epithelial CK5/CK8+ intermediate cells and a survival factor for epithelial CK8+ luminal cells. These two opposite roles of the AR in different epithelial cells could contribute significantly to cellular homeostasis in the prostate.

Figure 7:
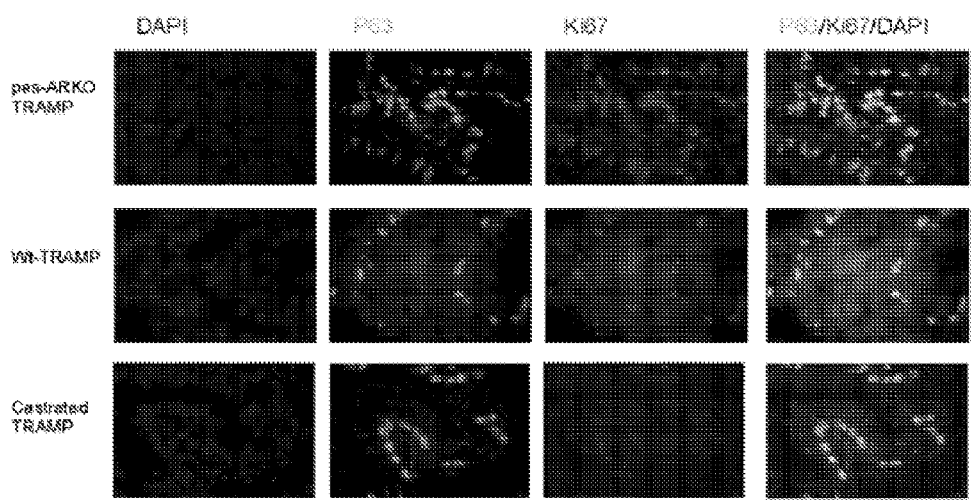
FIG. 7 shows increased proliferating cancer stem/progenitor cells, and expanded cancer stem/progenitor populations in pes-ARKO TRAMP.
Figure 7:
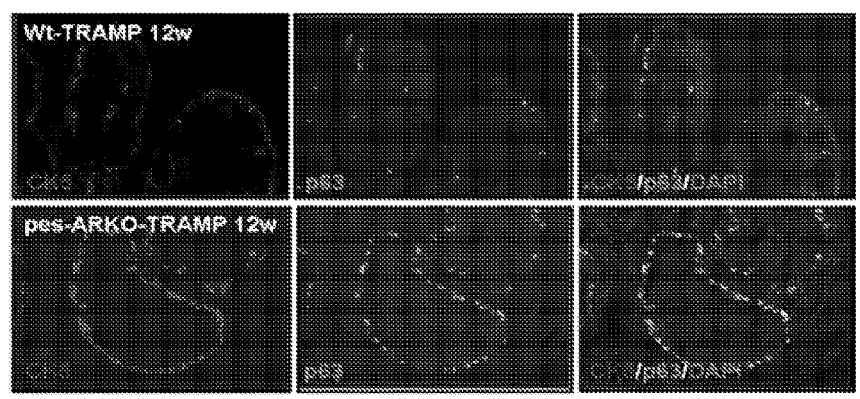
Figure 7:
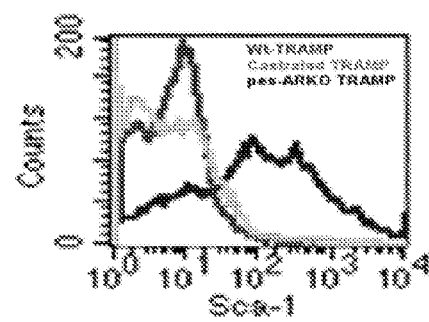
Figure 7:
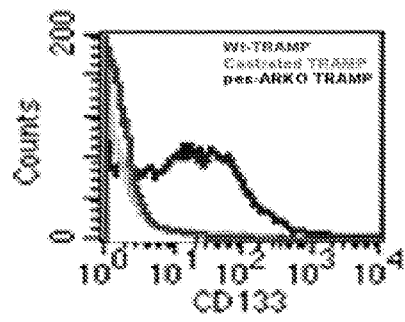

It was also observed that increased proliferating cancer stem/progenitor cells (FIG. 7a), and expanded cancer stem/progenitor populations, defined as p63+/CK5+ double positive (FIGS. 7a and 7b), Sca-1+(FIG. 7c), or CD133+(FIG. 7d), were significantly different in pes-ARKO TRAMP as compared with the wild type TRAMP. These studies also show the existence of stem/progenitor cell populations in prostate cancer, and establish that differentiation of the cancer stem/progenitor cells could also be modulated by androgen/AR signal. Therefore, AR could function differently in cancer stem/progenitor cells and differentiated luminal-like cancer cells. The opposite functions of the epithelial AR in different epithelial cells could then affect prostate cancer progression in TRAMP mice by favoring survival of differentiated tumor epithelium while suppressing proliferation of epithelial-basal intermediate cells.

Taken together, using this pes-ARKO mouse model, it is clear that epithelial AR plays essential yet diverse roles in development and adult homeostasis of the prostate gland, and epithelial AR plays important roles in the prostate stromal development via the regulation of a TGF-$\beta_1$ signal.

Example 2

Using various human and mouse stem/progenitor cell lines as well as a newly created mouse model with androgen receptor (AR) knockout only in basal epithelial cells, little AR expression was found in cytokeratin 5+(CK5$^+$/CK8$^{-/low}$) basal/stem/progenitor cells. AR started to express weakly in basal intermediate (CK5$^+$/CK8$^+$) cells, and was strongly expressed in terminally differentiated luminal epithelial (CK5$^-$/CK8$^+$) cells. These data show that AR plays a negative role to suppress CK5+ basal/stem/progenitor cell self-renewal, yet AR expression also plays an essential role to drive basal/stem/progenitor cells into a more differentiated state. These results suggest the differential AR expression in different cell developmental stages, from undetectable in earlier stem/progenitor stage and then gradually expressed during prostate cell lineage advance, could be essential in maintaining their characteristics and determining their differentiation into terminally differentiated luminal epithelial cells in the prostate.

Using multiple mouse and human basal/progenitor cells as well as different in vivo mouse models, the date provided herein show that AR could play a negative role to suppress self-renewal of stem/progenitor cells and proliferation of basal epithelial cells, yet AR expression also plays essential roles to drive stem/progenitor cells into a more differentiated state.

Cell Culture

Cultures of mouse progenitor cells (mPrE) were maintained in RPMI growth medium containing 10% FBS. Normal human basal cells from LifeLine (LifeLine-basal) were maintained in ProstaLife™ prostate epithelial cell culture medium (Lifeline, Germany) supplemented with LifeFactors (TGF-α, epinephrine, insulin, transferrin, hydrocortisone) provided with this medium.

MTT Cell Growth Assay

Cells were plated onto 24-well plates. At various time points indicated, MTT solution was added to cells for 30 minutes, then media were removed, isopropanol used to dissolve the MTT salt, and OD were measured at 570 nm.

Immunohistochemical Staining (IHC)/Immunofluorescence (IF) Staining of Cells/Tissues Cells were seeded on the 4-well chamber slides and fixed with methanol. After fixation, cells were washed with PBS 3 times for 5 min and then cells were blocked with 1% FBS for 1 hr. Cells were washed with PBS 3 times and then incubated with primary antibodies in 3% BSA in PBS overnight at 4° C. Antibodies used were: anti-Ki67 (NCL, 1:1000), anti-p63 (Santa Cruz 1:250), anti-AR (Santa Cruz, N20 1:250), anti-PSCA (Santa Cruz, 1:200), anti-CD44 (Santa Cruz, 1:250), anti-CK5 (Covance, 1:250), anti-CK8 (Abcam, 1:250), and anti-sca-1(1:250. eBioscience, San Diego, Calif.). Cells were then incubated with 1:200 diluted biotinylated secondary antibody (Vector Laboratories) and ABC solution (Vector Laboratories) for IHC, or with fluorescent secondary antibodies for IF (either Alexa 594 or Alexa488 tagged). For IHC, cells were stained by AEC (DAKO, Carpinteria, Calif.), followed by Mayor's hematoxylin counterstaining Formalin-fixed paraffin wax-embedded tissues were cut into 5 μm sections and placed on poly-L-lysine coated slides, deparaffinized, rehydrated, and then sections were subjected to antigen retrieval for 10 min. Then they were blocked with normal horse serum and incubated with appropriate primary monoclonal antibodies, appropriate fluorescein tagged secondary antibody (for IF), or visualized by VECTASTAIN ABC peroxidase system and DAB (diaminobenzidine) kit (Vector Laboratories) (for IHC).

Western Blot Analysis

Cell lysates were resolved with 10% sodium dodecyl sulfate-polyacylamide gel electrophoresis (SDS-PAGE), blotted with AR antibody (N20, Santa Cruz Biotechnology Inc.), and incubated with secondary antibodies conjugated with horseradish peroxidase. Proteins were visualized by using the Pierce ECL Western Blotting Substrate (Thermo Scientific) according to the manual's instructions. GAPDH served as loading controls.

RNA Extraction and Real Time Quantitative PCR (qRT-PCR)

Total RNAs were extracted with Trizol (Invitrogen, Carlsbad, FA) according to the manufacturer's instructions. Two μg mRNAs were used for reverse transcription to cDNAs using Superscript III (Invitrogen). Quantitative qRT-PCR was performed using cDNA, specific gene primers, and SYBR green master mix (Bio-Rad Laboratories, Hercules, Calif.) on an iCycler iQ Multi-color real-time PCR machine (Bio-Rad Laboratories, Hercules, Calif.).

Flow Cytometry Analysis of Cell Markers

Cells were detached with 5 mM EDTA and then washed with 1% FBS in PBS (flow washing buffer). After washing, cells were stained with sca-1, CD49f, and CD44 (eBioscience), washed again with 1% FBS in PBS, and resuspended in PBS, and then analyzed by flow cytometry according to the previous publication.

Lentivirus Infection 293T cells were transfected with a mixture of DNAs (Lentiviral vectors pWPI) (Addgene, Cambridge, Mass.)

containing AR (vectors were used as control), pMD2.G packaging plasmid, and psPAX2 envelope plasmid, at a 4:1:1 ratio) using Lipofectamine (Invitrogen) according to the transfection protocol. Culture media containing virus was collected 32 hrs after transfection. Media was filtered through 0.45 µm filter to remove cell debris or cells. Purified media was added onto the cultured cells with 2 µg/ml polybrene. Cells were refreshed with culture media 24 hrs later and cultured for 3 days. After infection, media containing the virus were changed into normal culture medium. Since the pWPI vector contains GFP, transfection efficiency was monitored by detecting GFP fluorescence by fluorescence microscopy.

Isolation and Culture of Prostate Stem Cells

Cells from total prostate were isolated as described previously (see Tsujimura et al. "Proximal location of mouse prostate epithelial stem cells: a model of prostatic homeostasis," *J Cell Biol* 157:1257-1265 (2002)). Briefly, isolated prostates were collagenase (type I, Sigma) treated for 3 hrs, trypsin treated, harvested, and filtered using a strainer (40 µm), and seeded onto irradiated NIH3T3 feeder cells in PrEBM (Lonza) media in 48-well plates or onto NIH3T3 cells that were treated with 100 µM mitogen for 3 hrs at 37° C. When feeder cell layer was not used, PrEBM medium was supplemented with growth supplements (Lonza, Allendale, N.J.).

Sphere Formation Assay mPrE cells and PSCs (vector/AR infected; 2,500 cells) were suspended in 1:1 matrigel (BD Bioscience, Bedford, Mass.)/medium in a total volume of 100 µl. Samples were plated around the rims of wells on a 24-well plate and allowed to solidify at 37° C. for 10 min. The media (1 ml) were added after solidification and were replenished every 3 days. Ten days after plating, spheres with a diameter over 40 µm will be counted.

Development of Basal-ARKO Mice

Basal-ARKO mice were generated by mating female mice harbouring floxed AR alleles (floxAR/X) with male transgenic mice expressing Cre recombinase under the control of the CK5-promotor.

Genotyping

Detection of Cre and floxAR genes was performed by RT-PCR using primers of Cre and floxed AR. DNAs were isolated from tail snips and RT-PCR was performed. Evaluation of exon 2 deletion in AR was examined using primers that span exons 1-3 of the AR gene.

Histologic Examination of Mice

Tissue sections from ventral prostate at different ages were stained with hematoxylin and eosin and their morphology was examined under a dissecting microscope.

Statistical Analysis

Values were expressed as mean±standard deviation (S.D.). The Student's t test was used to calculate P values. P values were two-sided, and considered statistically significant when <0.05.

AR Suppresses Growth of Established Mouse Prostate Stem/ Progenitor mPrE Cells

FIG. 8A shows a photomicrograph of AR expression in PDE cells. To investigate the potential AR role in self-renewal of prostate stem/progenitor cells, the effect of AR expression on self-renewal/proliferation of mPrE cells was tested. As the name of this cell line indicates (mPrE: mouse prostate epithelial cells), this cell line was originally derived from normal mouse prostate tissues. The examination of characteristics of this cell line revealed that this cell line is a basal epithelial cell line and immunofluorescence (IF) staining results also indicate that this cell line is of basal epithelial cell origin (FIG. 8C). Interestingly, the flow cytometric analysis results (FIG. 8B) demonstrated that the mPrE cells are even closer to stem/progenitor cells since they exhibit 98% of cells stained positive for stem/progenitor cells markers, sca-1 and CD49. These cells were also positive for the progenitor cell marker, p63 (FIG. 8C), but not for the intermediate cell marker, prostate stem cell antigen (PSCA) indicating that these mPrE cells are closer to stem/progenitor cells than the more differentiated intermediate type cells. So, this mouse established cell line was used as a source to study AR role in basal/stem/progenitor cells. These mPrE stem/progenitor cells express little AR when judged by IF staining (FIG. 8C) and Western blot analysis (FIG. 8D) results. However, a lower level of AR mRNA was detected via qRT-PCR analysis (FIG. 8E). Interestingly, when AR was forcibly expressed via viral infection, self-renewal/proliferation of these mPrE cells was significantly suppressed when examined by MTT assay (FIG. 8F), sphere formation assay (FIG. 8G), and Ki67 IF staining (FIG. 8H) indicating that AR plays a negative role to suppress self-renewal/proliferation in these mPrE stem/ progenitor cells. The MTT assay was performed at castrated level (1 nM DHT) and intact level (10 nM DHT) of androgen and the suppressive effect of AR on proliferation was observed and not dependent on androgenic concentration (FIG. 8F).

AR Suppresses Self-Renewal of Primary Prostate Stem/ Progenitor Cells

Primary mouse prostate stem/progenitor cells (mPSCs) were isolated from 7-8 week old male mice by exploiting cell surface markers, sca-1 and CD44 that have been used to distinguish mPSCs from other cell populations. Between 1.8 to 2.8% of sca-1$^+$/CD44$^+$ population cells were obtained among the total prostate cell preparations (FIG. 9A). The isolated sca-1$^+$/CD44$^+$ mPSCs cells were grown on feeder layer cells (NIH3T3) that have been pretreated with mitomycin to avoid proliferation. When these cells began growing, the expression of stem cell markers was tested by IF staining. The sca-1$^+$/CD44$^+$ mPSCs were also shown to be positive for CK5 staining; indicating that these cells were basal cell originated stem cells (FIG. 9B). As expected, these sca-1$^+$/CD44$^+$ cells did not stain positive for AR and Western blot analysis also detected little AR protein (FIGS. 9C and 9G) although a very low level of AR mRNAs was detected via qRT-PCR analysis (FIG. 9F). This is consistent with the results of mPrE stem/progenitor cell line shown in FIGS. 8D and 8E.

These primary sca-1$^+$/CD44$^+$ mPSCs were grown as a colony on the feeder cell layer (FIG. 9D). Positive IF staining for CK5, CD44, and sca-1 confirmed these colony forming cells were mPSCs (FIG. 9E). These mPSCs were then infected with lentivirus carrying either vector or AR and the colony forming ability was examined to compare self-renewal ability of the vector or AR expressing mPSCs. FIG. 9H demonstrates that the colony size and number of the AR carrying virus infected mPSCs were smaller than those of vector carrying virus infected mPSCs, and FIG. 9I also shows that the sphere forming ability was lower when AR was expressed in cells. These results suggest that AR in these primary sca-1$^+$/CD44$^+$ mPSCs also plays a negative role to suppress their self-renewal.

Figure 10:
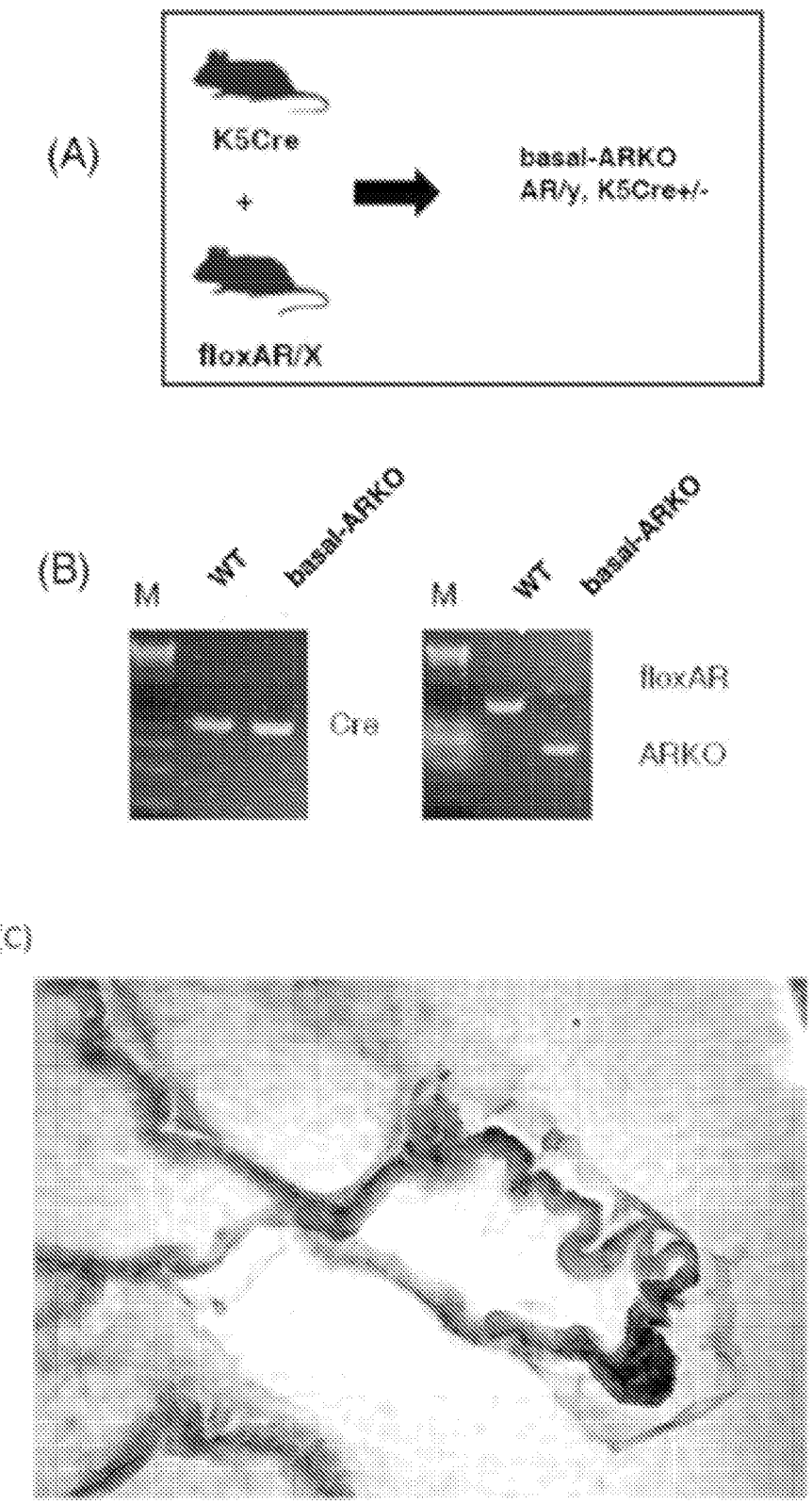
FIG. 10 shows the development of basal-ARKO mice.
Figure 10:
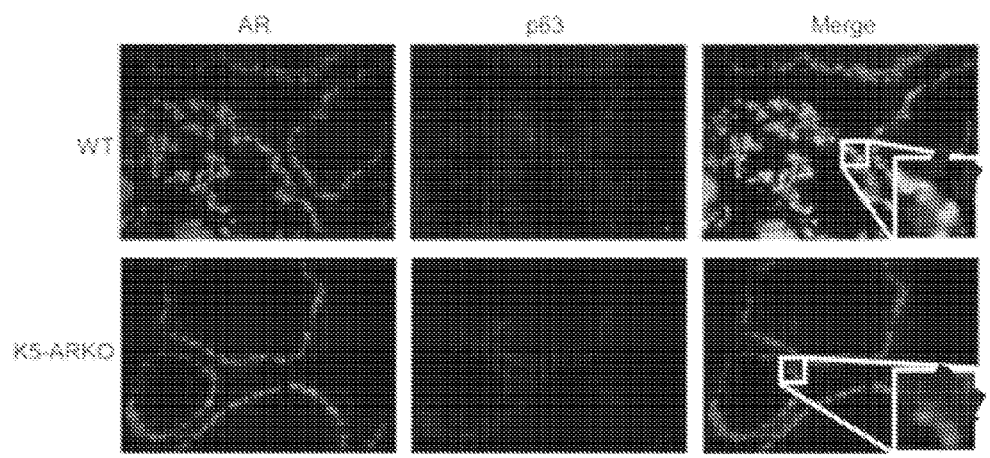
Figure 10:
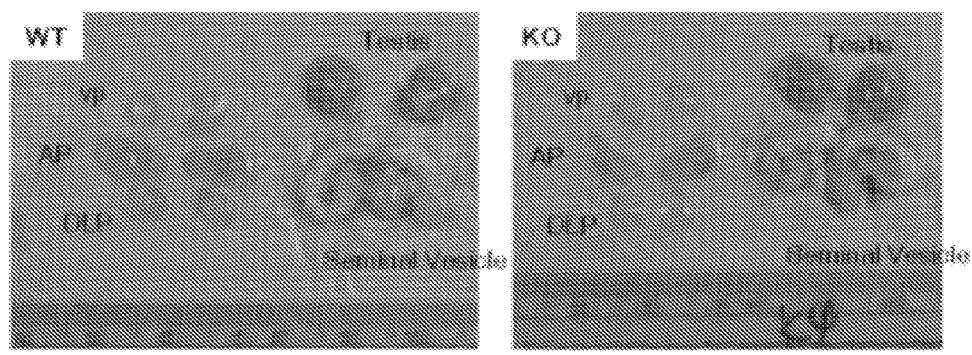
Figure 10:
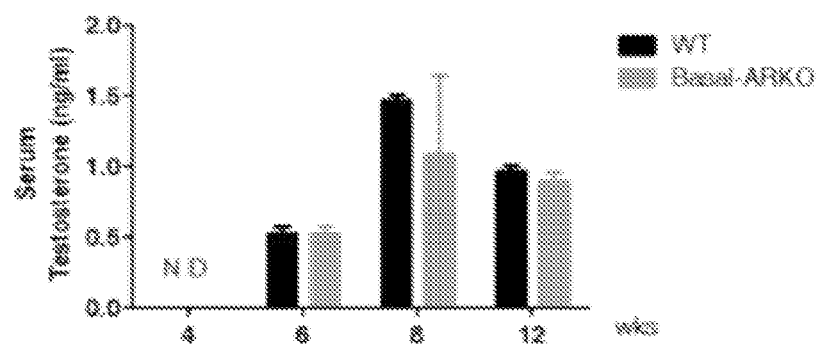
Figure 10:
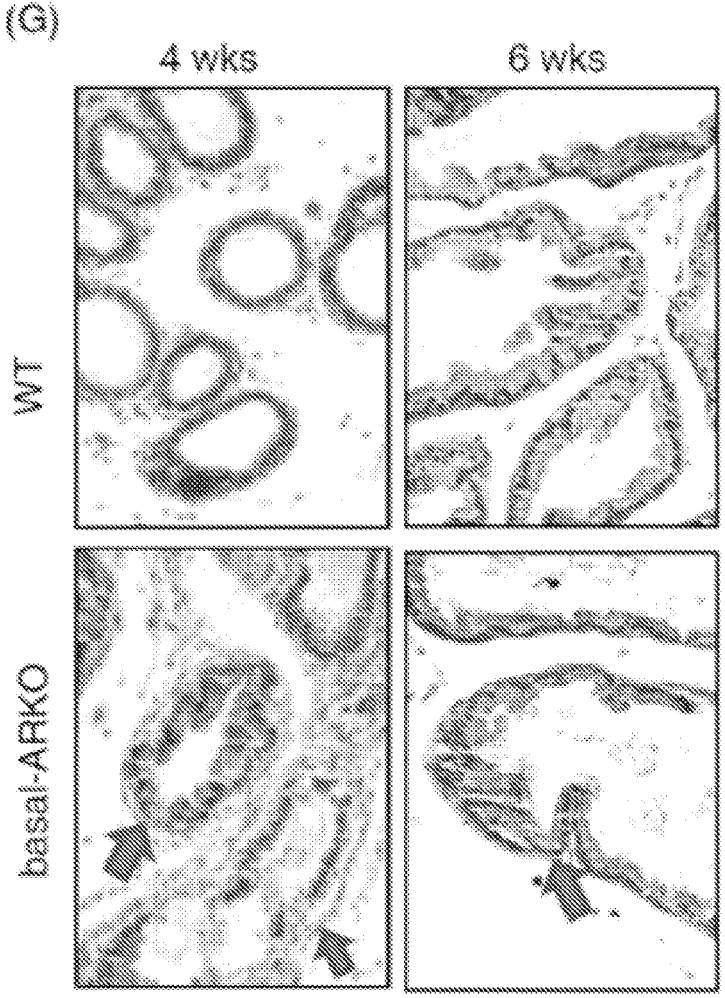

Mice Lacking AR in Basal Cells Lead to Increased Self-Renewal of Basal Epithelial Cells The in vivo role of AR in basal epithelial cells was also investigated. A mouse model with AR knockout only in basal epithelial cells (basal-ARKO) was developed by mating male CK5-Cre mice with female floxAR mice. FIG. 10A shows the strategy for developing the basal-ARKO mice and FIG. 10B is the result of genotyping showing cre and floxAR expressions in transgenic mice. Before the mating step, it was determined whether the CK5-Cre activity was expressed only in basal epithelium. Using reporter mice, a male CK5-Cre mouse was mated with a female ROSA26 reporter mouse. As shown in FIG. 10C, due to β-galactosidase (β-gal) gene activation, reflects cre expression in ventral prostate (VP), suggesting the β-gal activity was detected in almost all basal epithelium areas, not in luminal epithelium and the expression was more obvious in the VP and dorsolateral prostate (DLP) lobes than anterior prostate (AP) lobe.

Figure 8:
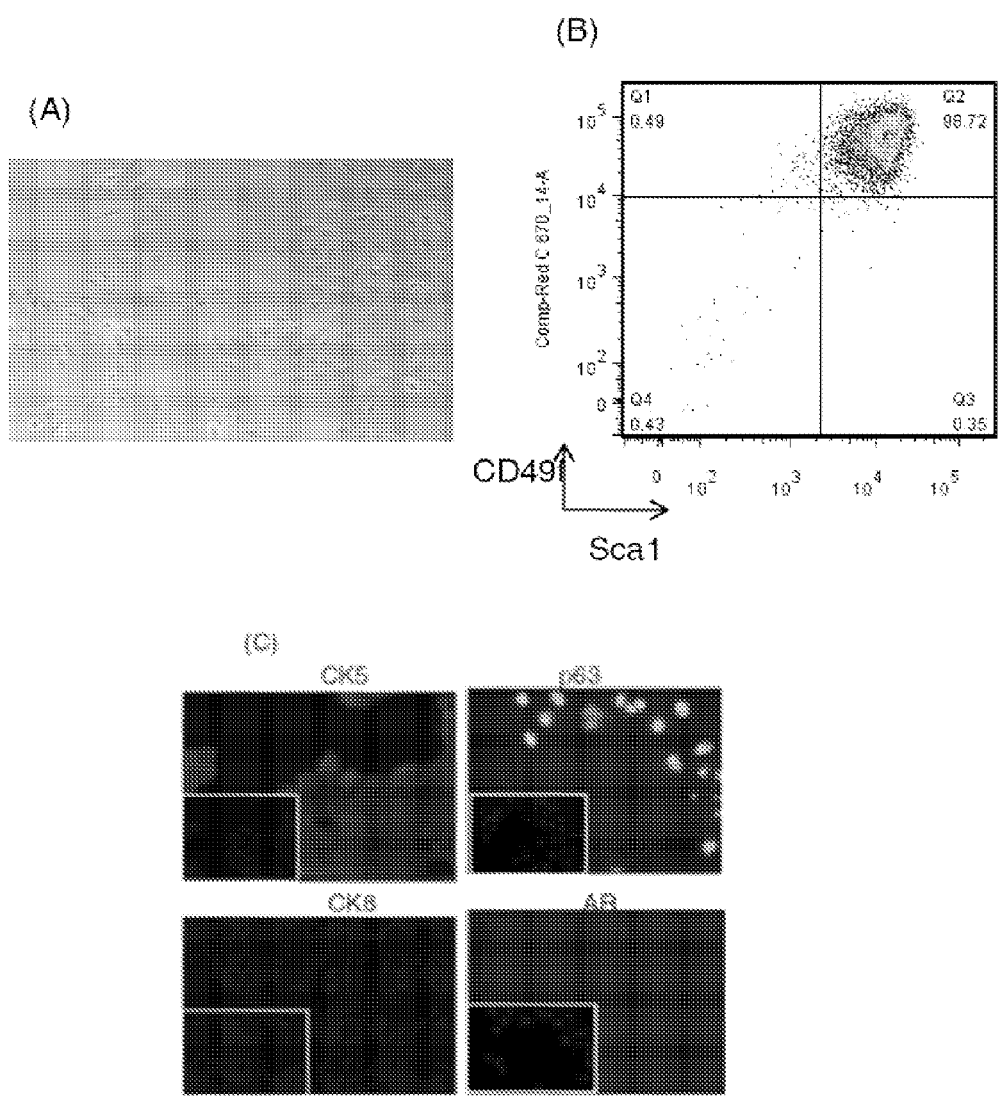
FIG. 8 shows that AR expression suppresses self-renewal/proliferation of mPrE cells.
Figure 8:
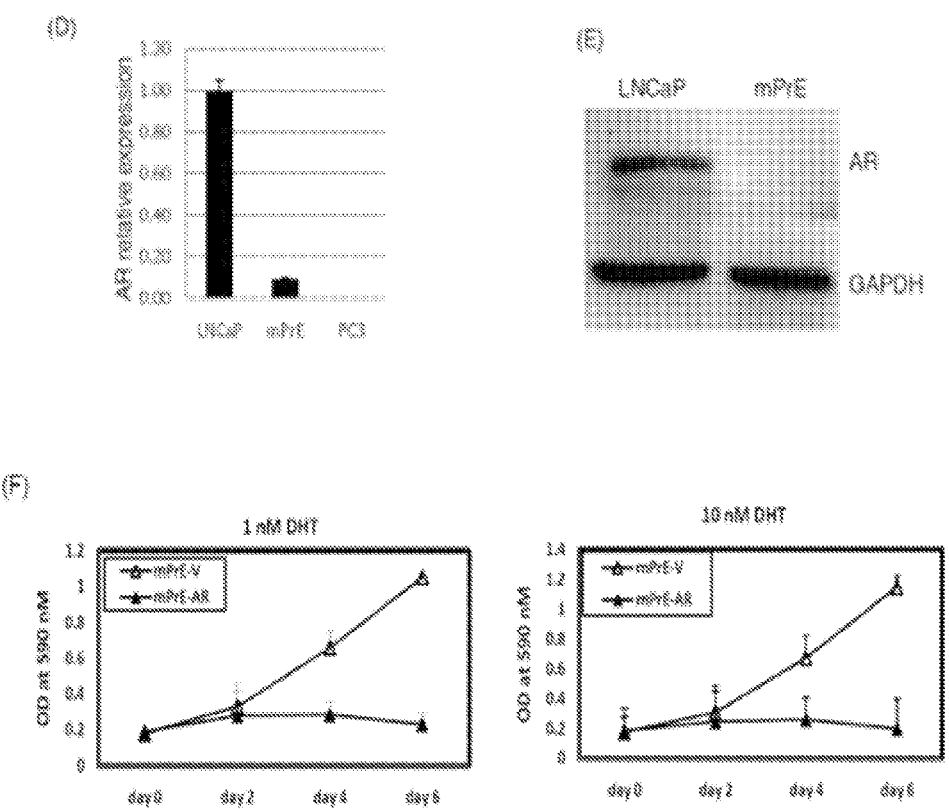
Figure 8:
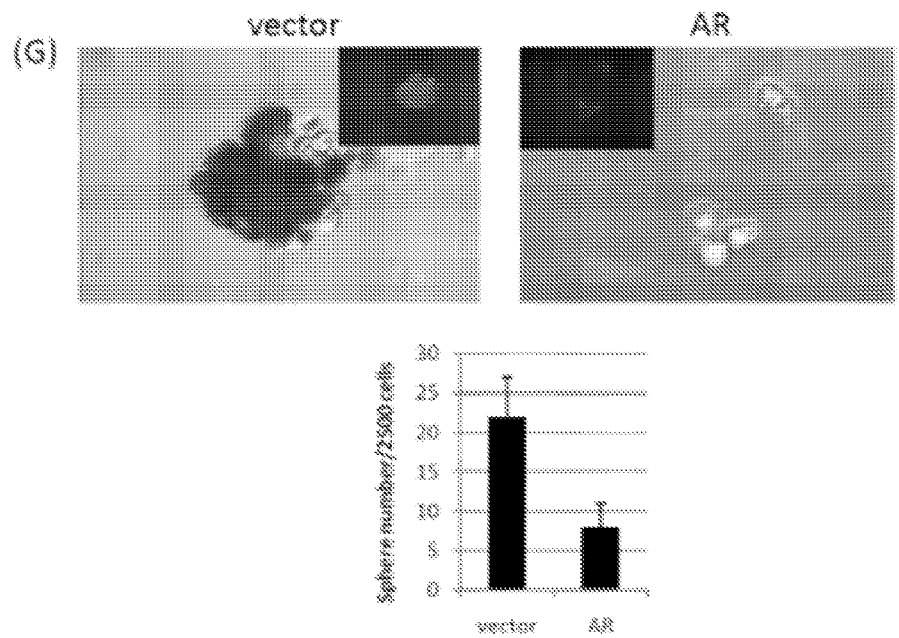
Figure 8:
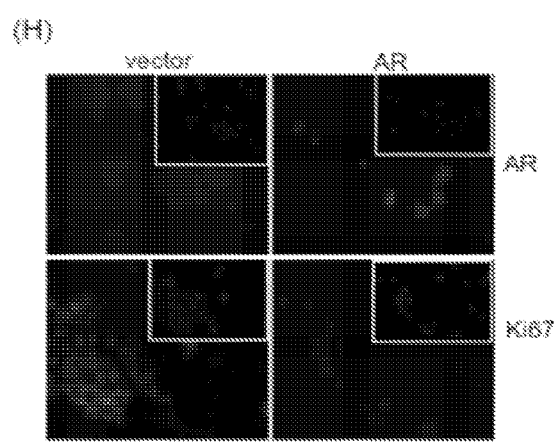
Figure 9:
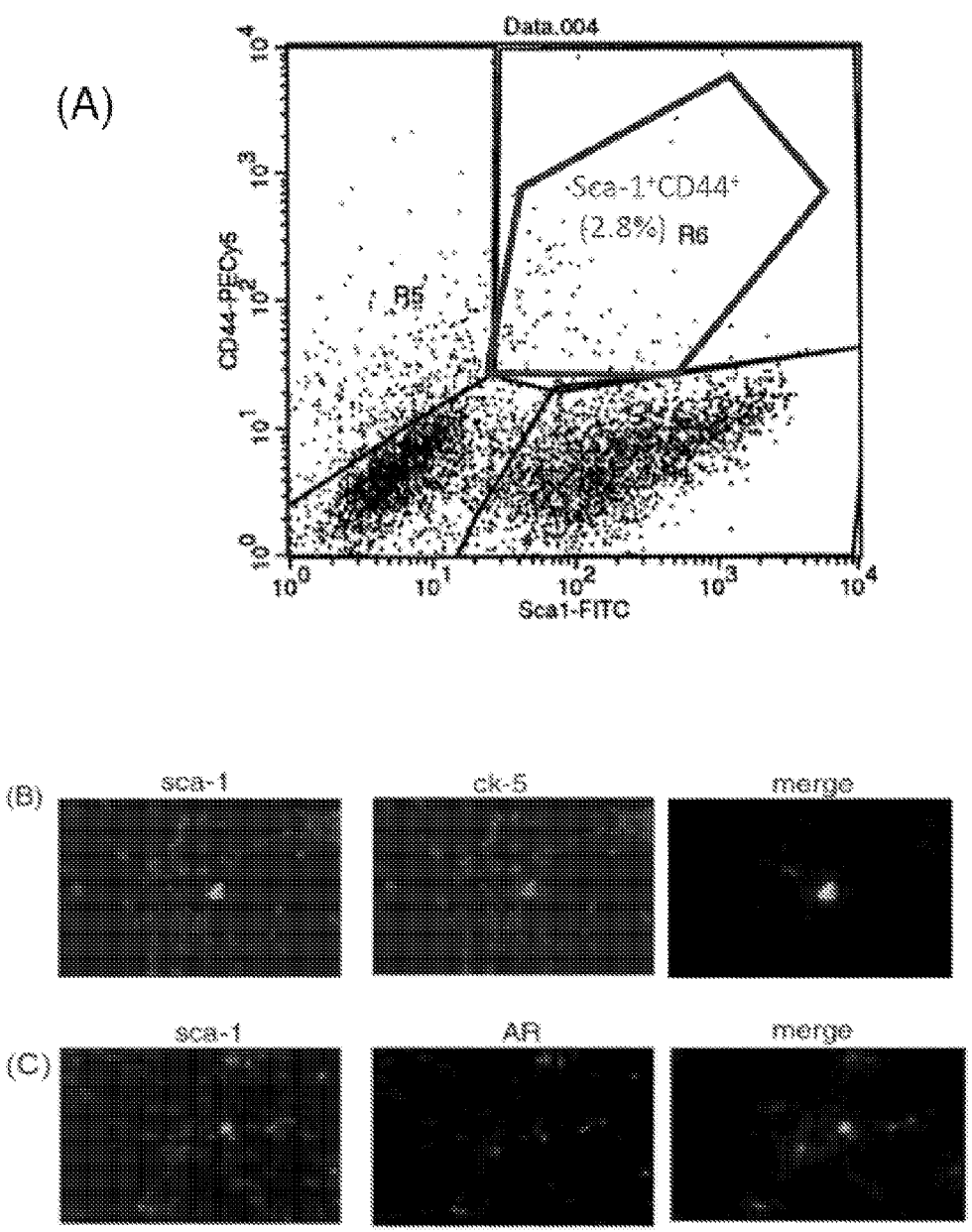
FIG. 9 shows that AR expression inhibits self-renewing of PSCs. Total epithelial cells were isolated from prostate lobes, minced, collagenase treated, and trypsinized After filtering cells using a cell strainer (40 nm), total cells were seeded onto NIH3T3 feeder cells that had been treated with mitomycin (100 μM).
Figure 9:
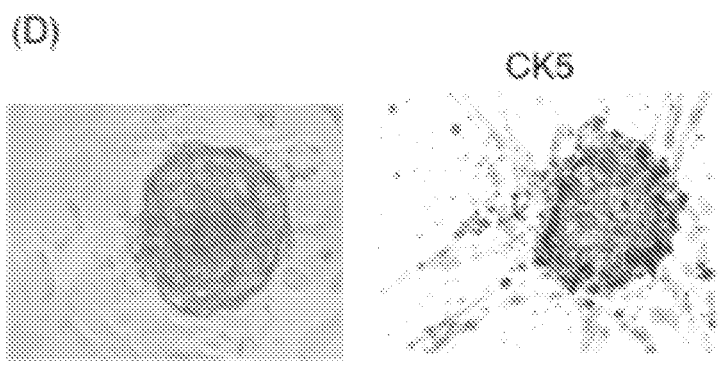
Figure 9:
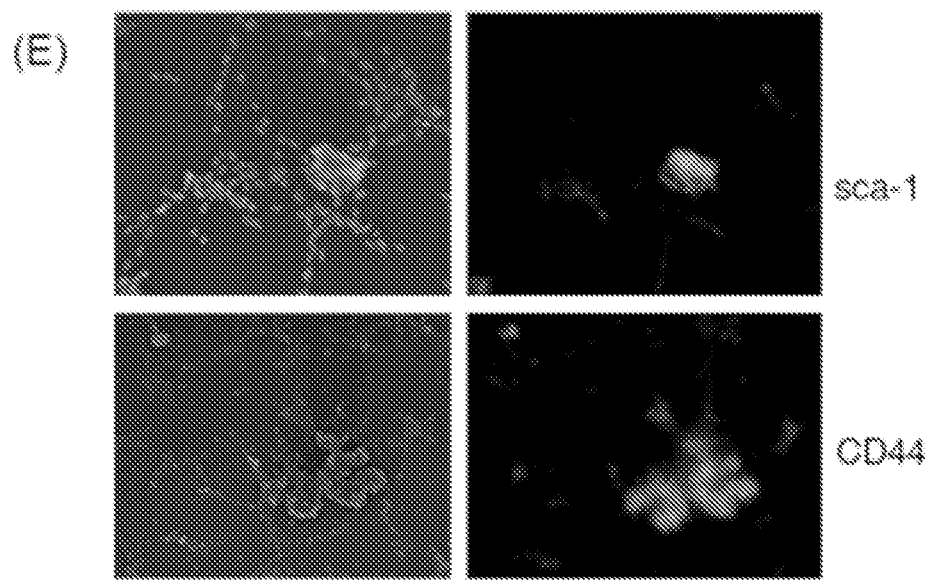
Figure 9:
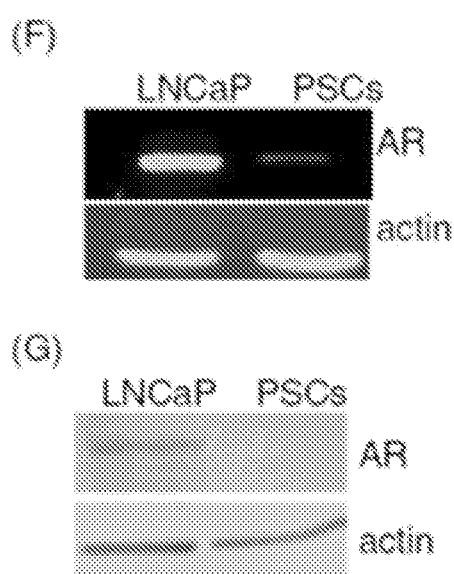
Figure 9:
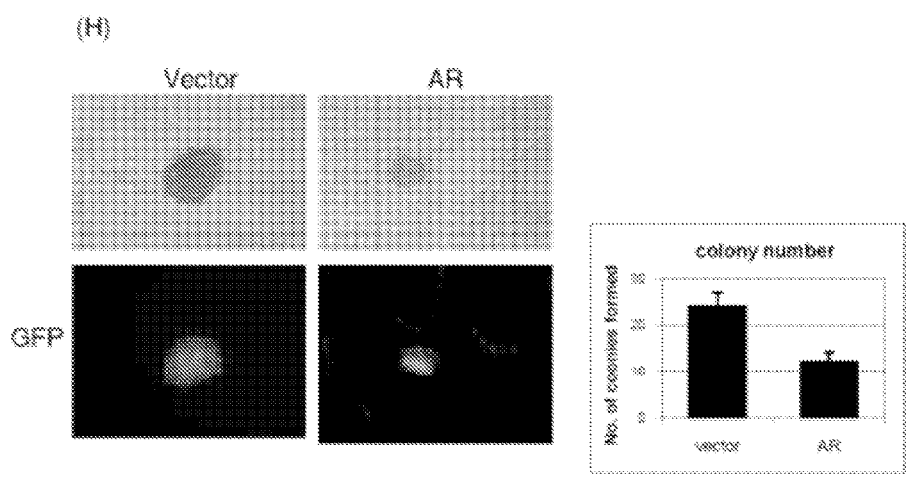
Figure 9:
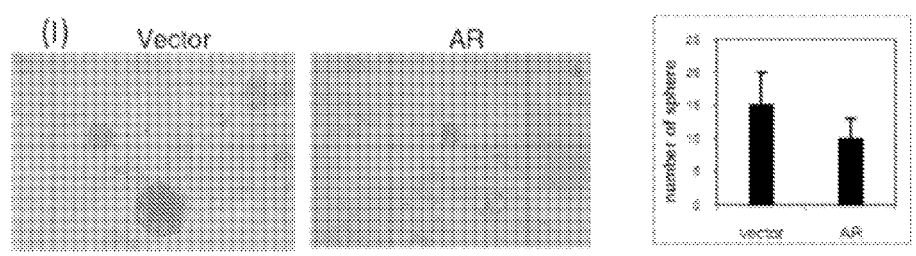

To verify that AR was knocked out in basal epithelium of basal-ARKO mice, IF double staining was performed of VPs from 4 week old WT and basal-ARKO mice using antibodies of AR and p63 (basal cell marker). The results showed that basal AR staining and p63 staining overlapped in the WT mice, but not in the basal-ARKO mice. However, strong AR staining was detected in the luminal epithelium of both WT and basal-ARKO mice (FIG. 10D). This result indicates that AR was specifically knocked out in basal epithelium in basal-ARKO mice. Most of the phenotypes including total body weight, testosterone level, and lobes sizes were similar between WT and basal-ARKO mice (FIGS. 10E, 10F, and 10G). However, histological examination of prostates revealed some abnormalities in basement membrane organization, with disorganization of membranes between epithelium and stromal compartment found in prostate glands of 4 and 6 week old basal-ARKO mice (FIG. 10G arrows). The distribution of CK5 and CK8 positive cells was analyzed by IF staining of VP tissues of basal-ARKO and control WT littermate mice at 4 weeks old and it was found that the CK5 positive cells (basal epithelial including stem/progenitor), stained in FIG. 11A, were significantly increased in 4 week old basal-ARKO mice compared to the WT control mice. The increased CK5 positive cell numbers could be due to higher proliferation and/or lower apoptotic death. Indeed, higher proliferation of basal and intermediate cells was detected in 4 and 6 week old basal-ARKO mice. It was found that Ki67 positive cells were much higher in 4 and 6 week old basal-ARKO mice compared to WT mice (FIG. 11B). In contrast, there were no significant differences in apoptotic death rate in 4 and 6 week old basal-ARKO mice vs WT mice. These results indicate that AR plays a negative role to suppress cell proliferation of basal cells including stem/progenitor, which is in agreement with the above results obtained from in vitro stem/progenitor cells (FIG. 8 and FIG. 9).

AR Suppresses Growth of the Established Human Prostate Basal Cell Line

Figure 12:
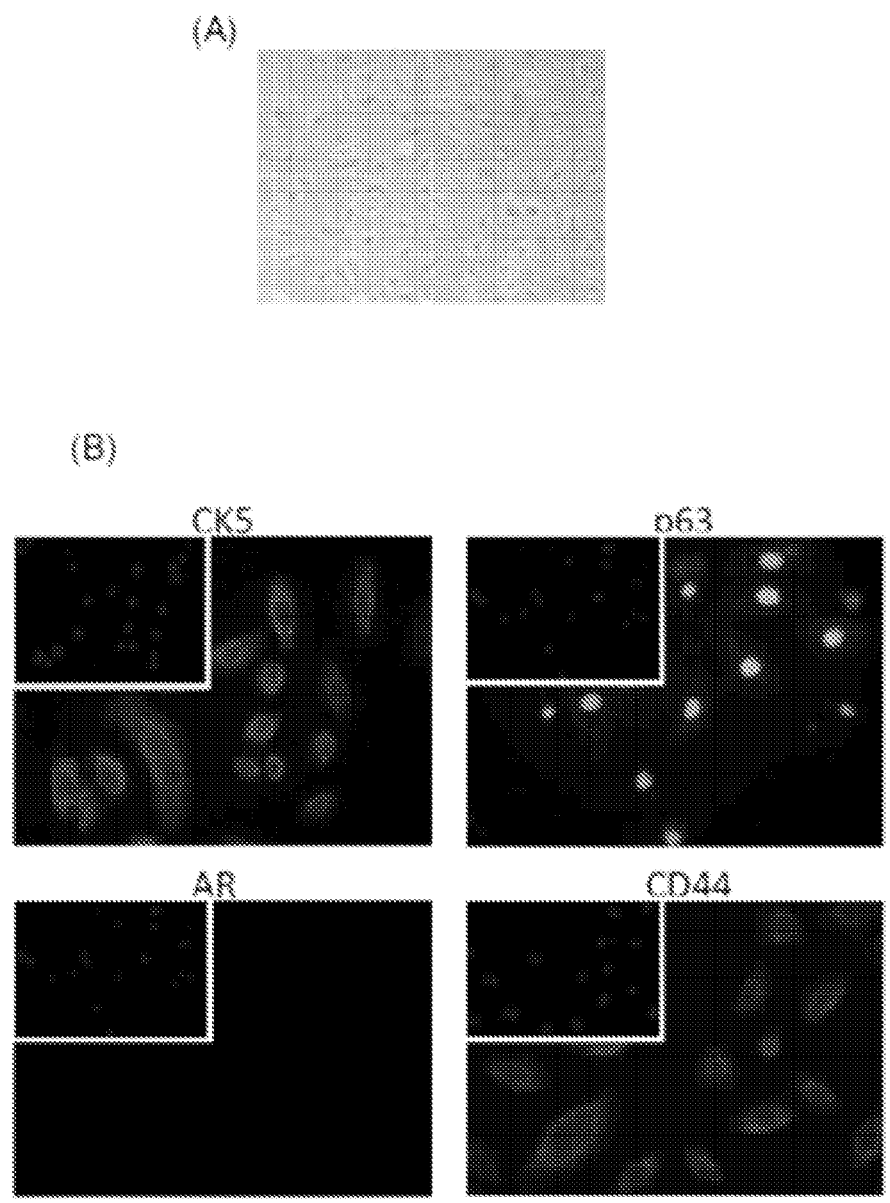
FIG. 12 shows that AR suppresses growth of normal human basal cells.
Figure 12:
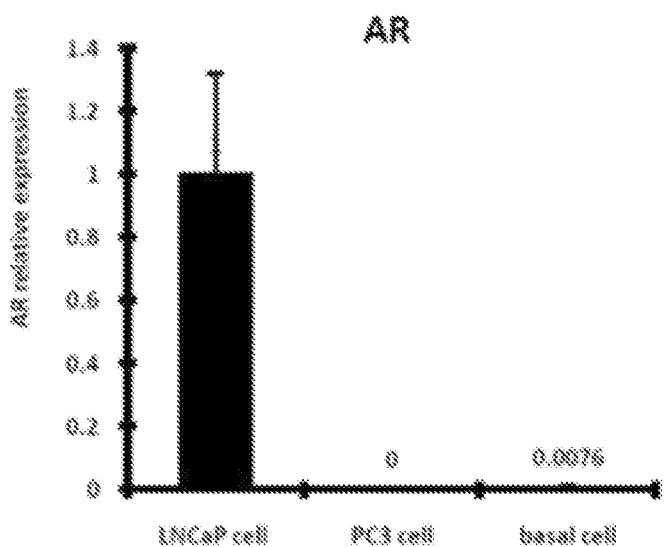
Figure 12:
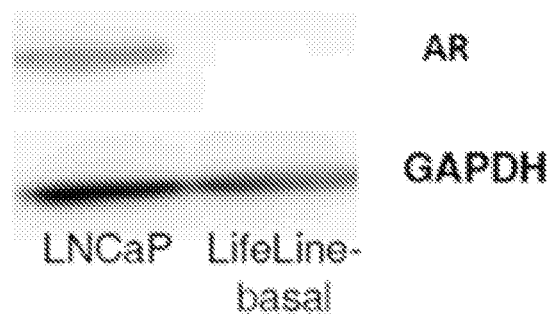
Figure 12:
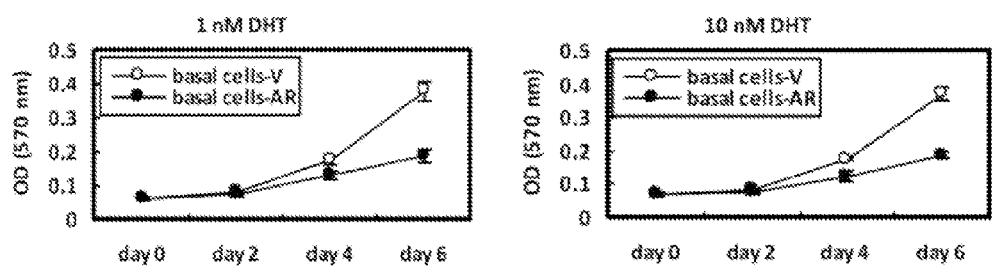
Figure 12:
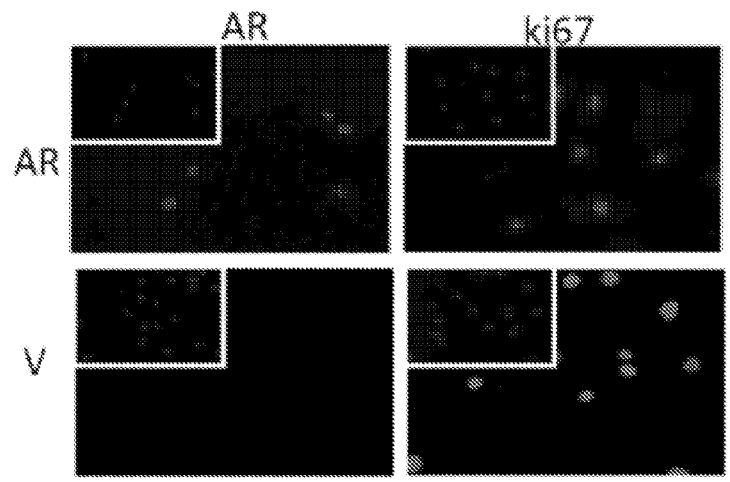

The effect of AR knockout in proliferation of basal cells using a normal human donor basal cell line obtained from Lifeline (Germany) (LifeLine-basal) was investigated. The characteristics of this basal cell line (LifeLine-basal) are shown in FIG. 12. These human prostate cells showed positive staining with CK5 and p63 (FIG. 12B) but failed to express CK8 and AR. Whether the proliferation of these cells was also inhibited upon AR expression was also tested. As shown in FIG. 12E, AR expression significantly suppressed the growth of these cells at castration level (1 nM DHT) and intact level (10 nM DHT) of androgen. IF staining analysis with Ki67 showed that the AR expressing cells exhibited a significantly lower level of Ki67 positive cells compared to the vector control cells (FIG. 12F), confirming the suppressive role of AR in proliferation of basal epithelial cells, which is consistent with the data obtained from mice.

Collectively, all data generated from either human or mouse prostate support the role of AR as a suppressor of the self-renewal or proliferation of prostate basal stem/progenitor cells.

AR Roles in Prostate Differentiation

The role of AR in the prostate cell differentiation process was also investigated. When mice containing CK5-cre/WT AR were crossed with ROSA26 mice (CK5-cre/WTAR:ROSA), β-gal activity was expressed in all prostate tissues including luminal epithelium, but the reporter mice derived from crossing of CK5-cre/floxed AR and ROSA26 (CK5-cre/floxAR:ROSA) mice showed β-gal activity only in basal epithelium (FIG. 13A). It is likely that the fluorescence is observed in the entire luminal epithelium in the CK5-cre/WTAR:ROSA mice since the luminal epithelium in these mice is originated from the basal epithelium containing AR. However, the fluorescence is observed only in the basal epithelium in the CK5-cre/floxAR:ROSA mice, suggesting that the basal epithelium lacking AR cannot differentiate into luminal epithelium. Therefore luminal epithelium in these mice did not show the fluorescence. The luminal epithelium in these mice (CK5-cre/floxAR:ROSA) must originate from the basal epithelium containing AR, which may be due to incomplete knockout of AR in basal epithelium and consequently did not show fluorescence. This result indicates that AR in basal epithelium is important in mediating differentiation of basal cells into luminal epithelial cells.

The AR role in differentiation process has also been examined using a LifeLine-basal cell line. When cells were infected with a lentivirus carrying AR, expression of the differentiation markers Nkx3.1 and CK8 was increased, which also suggests that AR expression can drive basal cells towards the differentiated state (FIG. 13B).

Figure 11:
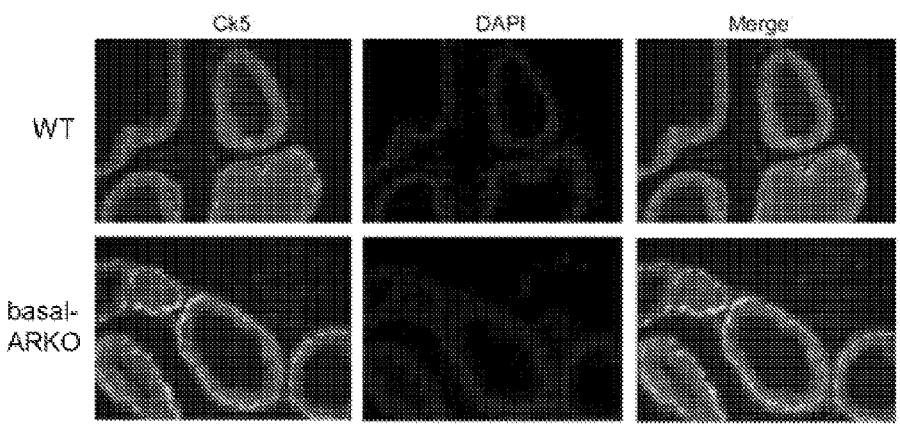
FIG. 11 shows that CK5 positive cells are increased in basal-ARKO mice compared to wild type control mice.
Figure 11:
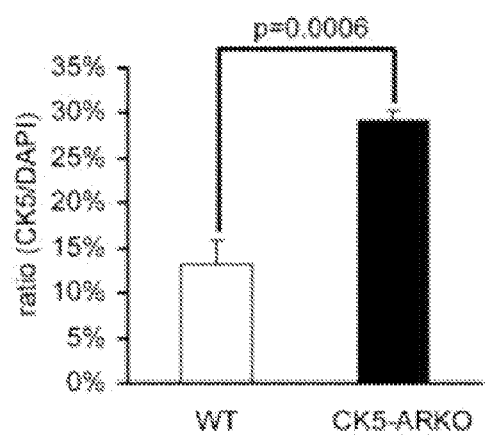
Figure 11:
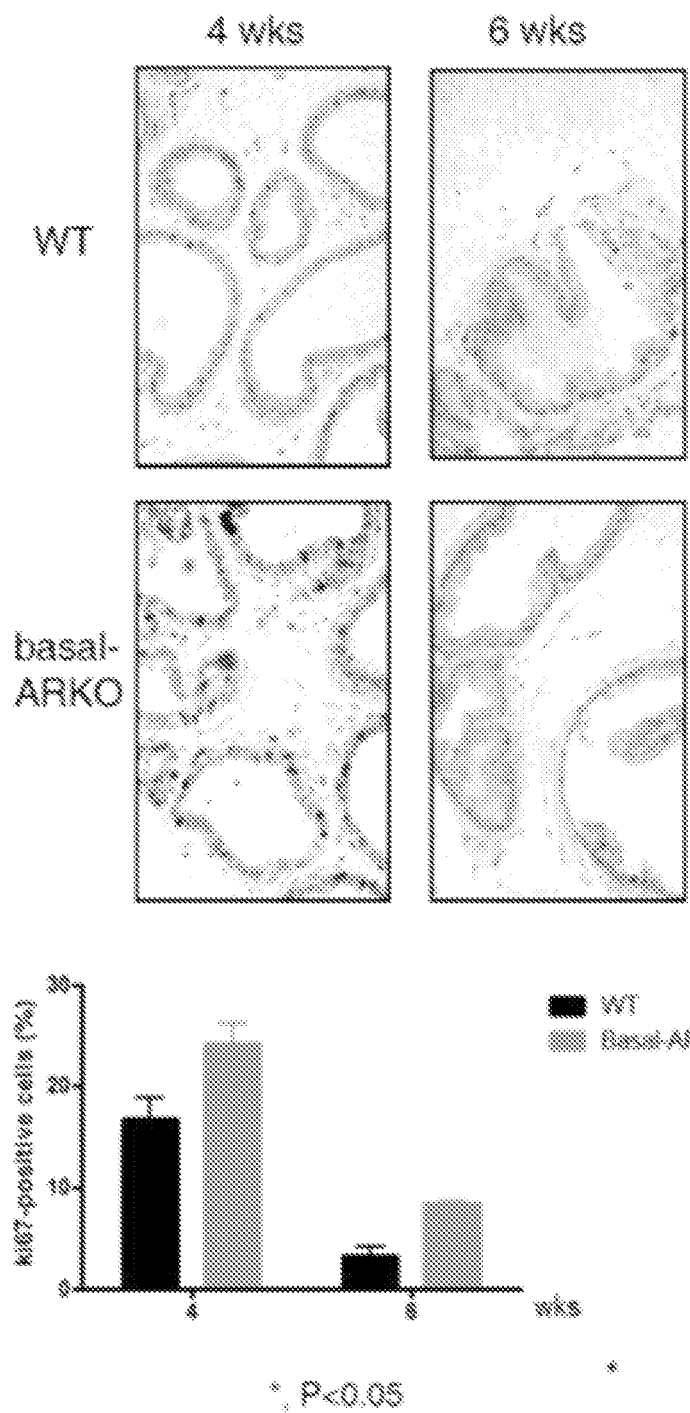

Prostate stem/progenitor cells are a subset of basal epithelial cells, so the role of AR in proliferation of basal cells was investigated using basal-ARKO mice. When the basal-ARKO mouse model was developed, the AR knockout efficiency was shown to be more than 80% when judged by AR/p63 IF double staining. The AR knockout effect in basal epithelium was more noticeable in mice of earlier ages (4 and 6 weeks) compared to older mice. No significant difference in the phenotypes of basal-ARKO mice compared to their control WT littermate mice were observed. However, a significant membrane disorganization in basal-ARKO mice (FIG. 10) was observed. Other than the difference in this phenotype, the AR knockout in basal epithelium increased proliferation of CK5 positive and CK5/CK8 double positive cells significantly. This result shows the suppressive role of AR in CK5 positive and CK5/CK8 double positive progenitor/intermediate cells (FIG. 11).

The suppressive role of AR in proliferation of normal basal cells of human origin (FIG. 13) was also revealed. The results of these studies show that the status of AR expression appears critical in maintaining the stemness of stem cells and promoting self renewal of stem/progenitor cells in the prostate basal cells. It is possible that the low level of AR in the basal compartment is important in the environment of the stem/progenitor cells. However, AR expression may be necessary to induce cells into more differentiated states.

Figure 13:
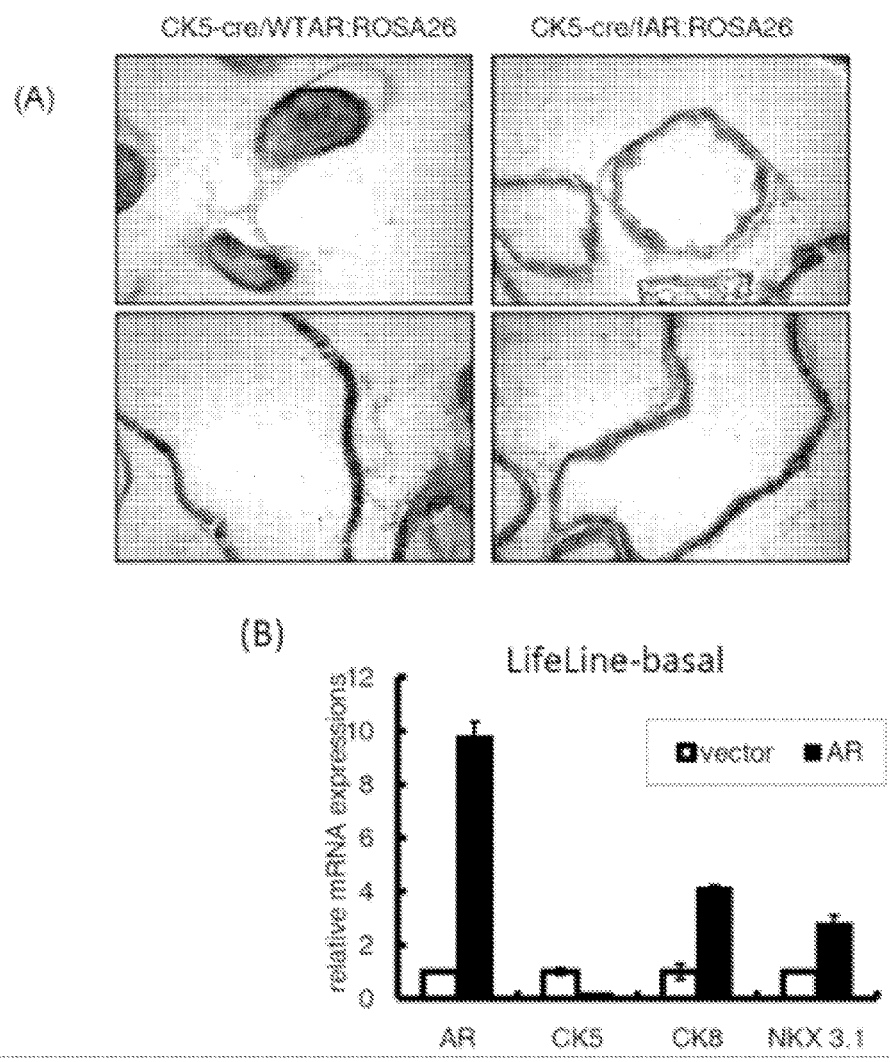
FIG. 13 shows that AR expression induces differentiation of basal cells.

Taken together, the status of AR expression determines which axis these cells are destined for: when AR is depleted, the direction is toward self-renewal of stem/progenitor cells; whereas when AR expression starts, the direction is toward the differentiation axis as shown in FIG. 13.

Example 3

It was found that AR plays a stimulatory role in proliferation of non-stem/progenitor (S/P) cells, but a suppressive role in S/P cells. A significant increase in the numbers of cancer S/P cells was detected in human/mouse tumor tissues after castration/ADT and the tumorigenicity of the S/P cells was significantly decreased when AR was expressed. This explains why targeting androgen/AR signaling cannot block expansion of both population cells. In order to develop a better strategy to block occurrence of castration resistant tumors completely, S/P and non-S/P cells were targeted simultaneously. It was possible by co-administration of the combined use of inhibitors to target S/P cells and the use of ASC-J9®, which is known to have AR degrading activity without toxicity to target non-S/P cells. To target cancer S/P cells, combined use of γ-tocotrienol (γ-TT), 5-aza-2'-deoxycytidine (5-AZA) and an inhibitor of selected signaling molecules activated in AR depleted S/P cells was applied.

The androgen deprivation therapy (ADT) has been a standard treatment for prostate cancer and effective for luminal epithelial tumors, but eventually patients show signs of androgen-independent progression and progress into hormone-refractory stage, for which no optimal therapeutic options are currently available.

As set forth above, AR plays a suppressive role in self-renewal/proliferation of normal S/P and basal epithelial cells. These results were obtained from studies using primary mouse prostate stem cells, the established normal mouse and human progenitor cell lines, and basal epithelium specific AR knockout mice. It was also found that the proliferation of the CK5 positive S/P/intermediate cells increased in prostate epithelial specific ARKO derivative of TRAMP mice (pes-ARKO/TRAMP) compared to the WT/TRAMP control littermates also suggesting the suppressive role of AR in the proliferation of these populations of cells.

The differential role of AR in prostate cancer S/P and non-S/P cells prompted investigation into whether targeting AR is the best way to treat prostate cancer in patients since targeting AR can block expansion of non S/P cells, but can expand the number of S/P cells. This explains why current ADT methods targeting universal androgen-AR signaling without considering cell type fails. In this study, the role of AR in non S/P and S/P cells was examined thoroughly using various sources of S/P cells from human prostate cancer cell lines and mice tumor tissues. Consistent results confirming the contrasting roles of AR in PCa S/P and non-S/P cells were obtained. Accordingly, a new strategy to block expansion of two population cells simultaneously was developed. The in vitro and in vivo tests to target two populations of cells were performed.

Infection of Cells

For the infection of lentivirus carrying vector or AR, 293T cells were transfected with a mixture of DNAs (Lentiviral vectors pWPI) (Addgene, MA) containing AR (vectors will be used as control), psPAX2 packaging plasmid, and pMD2G envelope plasmid, at a 4:3:2 ratio) using Lipofectamine (Invitrogen, CA). After infection, media containing the virus was changed into normal culture medium. Since the pWPI vector contains GFP, transfection efficiency was monitored by detecting GFP fluorescence.

Flow Cytometric Separation and Magnetic Bead Isolation of S/P Cells

For flow cytometric separation of S/P cells, cells ($2\times10^7$) were detached with 5 mM EDTA, and stained with antibodies of integrin and CD133 (for human prostate cancer cells) and integrin and sca-1 (for mouse tissues). The double positive population cells as well as double negative cells were collected by sorting using a BD FACS Diva cell sorter (Becton Dickinson Immunocytometry Systems, CA). For the separation by magnetic beads, cells were incubated with magnetic beads (Invitrogen) that have been conjugated with biotinylated antibodies. The positively stained cells were separated by placing tubes in magnetic field. The unbound cells were used as non-S/P cells after washing and the bound population cells were used as S/P cells.

Growth Assay

For an MTT assay, cells were incubated in 12- or 24-well culture plates ($10^5$-$10^3$ cells/well) and cultured. At 2, 4, and 6 days, 3-(4,5-dimethylthiazol-2-yl)-2,5-diphenyltetrazolium bromide (MTT; 0.5 mg/mL; Sigma) was added. After 2 hours of reaction, absorbances at 570 nm were measured. For soft agar colony formation assay, cell suspension ($1\times10^4$ cells/well in 6 well culture plates) of mixture of 1.5% agarose (Cambrex Bio Science Rockland, Ill.) and 2× medium (2 ml) was overlaid onto the solidified mixture of agarose base (final agarose concentration will be 0.75%). Two mL of normal medium containing various concentrations of DHT was added on top of the solidified agarose cell layer. All conditions were performed in triplicate. The plates were incubated at 37° C. in a humidified incubator for 21 days. The colonies developed were visualized by staining with 1% crystal violet. The colonies larger than 1 mm in diameter were counted. For sphere formation assay, a single cell suspension ($1\times10^3$, in 50 μl medium) was mixed with cold Matrigel 50 μl (kept on ice) and the mixture was placed along the rim of the 24 well with minimum triplicate experiments. The culture plates were placed in a 37° C. incubator for 10 min to let the mixture solidify and 500 μl medium was then added into the well. Cells were grown in 5% RPMI (for human PCa S/P cells) and epithelial basal medium (PrEBM) (Lonza) supplemented with growth supplement (Lonza) (for mouse cells) with addition of various concentrations of DHT (1 or 10 nM). Spheres numbers were counted after 7 to 14 days under Olympus light microscope and size differences were also examined.

Migration and Invasion Assay

Cells ($1\times10^5$) were added in the upper Transwell compartment. The medium (600 μl of 20% CS-FBS) containing 1 or 10 nM of DHT was added in the lower compartment to act as an attractant. After 24 hours of incubation, the filters were fixed in methanol for 10 min at 4° C., stained with 1% toluidine blue (BIO-RAD, CA) for 5 min at room temperature, and then washed carefully in $dH_2O$. Cells that were not migrated were removed from the upper face of the membranes with cotton swabs. After air drying, the membranes were observed under light microscope. The average number of cells per field of view (five random fields per membrane) was counted at 20× magnification. For an invasion assay, before the cells were planted into the upper Transwell, 50 μl Matrigel was added on the membrane. The incubation time was prolonged to 48 hrs.

Development of Xenograft Mouse Model

For generation of a xenograft mouse model, LNCaP or C4-2 cells ($1\times10^5$ cells per site, in 20 μl of medium mixed with Matrigel, 1:1 (v:v)) were injected orthotopically into anterior prostates and subcutaneously into 2 flanks of 8 wks old male athymic nude mice. Surgical castration was performed when tumors of subcutaneous injections reached 100 $mm^3$. Tumors of non-castrated mice were used as a control. Mice were sacrificed at 10, 20, and 30 days and the tumor tissues were stained using antibodies of CD133, integrin, CK8 and CK5. TRAMP mice (B6 background) were bred under a protocol approved by the Institutional Animal Care and Use Committee (IACUC) of the University of Rochester Medical Center. For injection of inhibitor molecules, two combinations or three combinations were i.p. injected into 5 groups of mice every other day and continued for 6 weeks. Group 1: castration only; Group 2: castration+ASC-J9; Group 3: castration+ASC-J9+γ-TT and 5-AZA, and Group 4: castration+ASC-J9+γ-TT and 5-AZA+LY294002.

AR Plays Opposite Roles in S/P and Non S/P Cells of PCa Cell Lines

Figure 14:
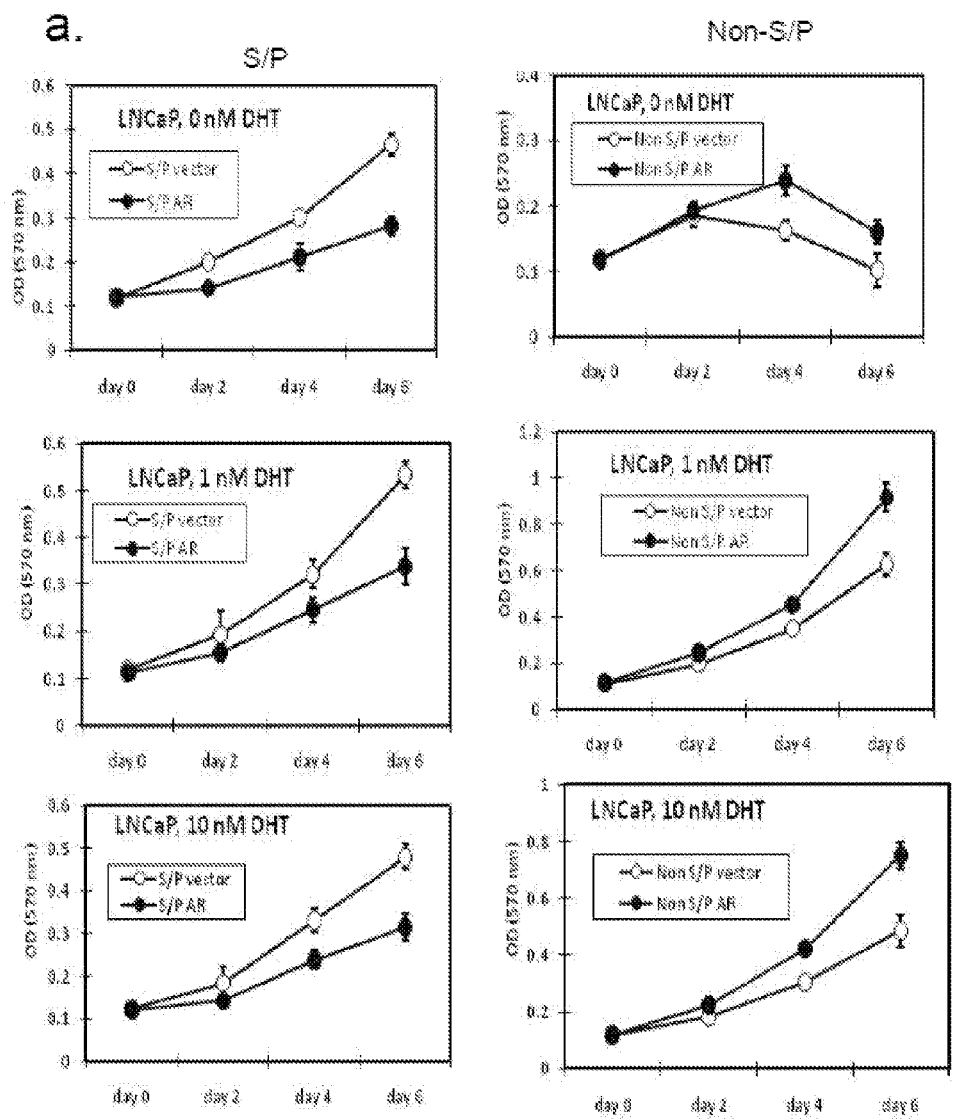
FIG. 14 shows the results of (a) MTT growth assay, (b) sphere formation assay, (c) soft agar colony formation assay, (d) Ki67 IHC staining, (e) BrdU labeling experiment, (f) migration assay, and (g) invasion assay of LNCaP-S/P cells and non-S/P cells after infection of lentivirus carrying vector or AR. Various concentrations of DHT (0, 1, and 10 nM) were added to the incubation mixture. AR expression played opposite roles in proliferation of S/P and non S/P cells.
Figure 14:
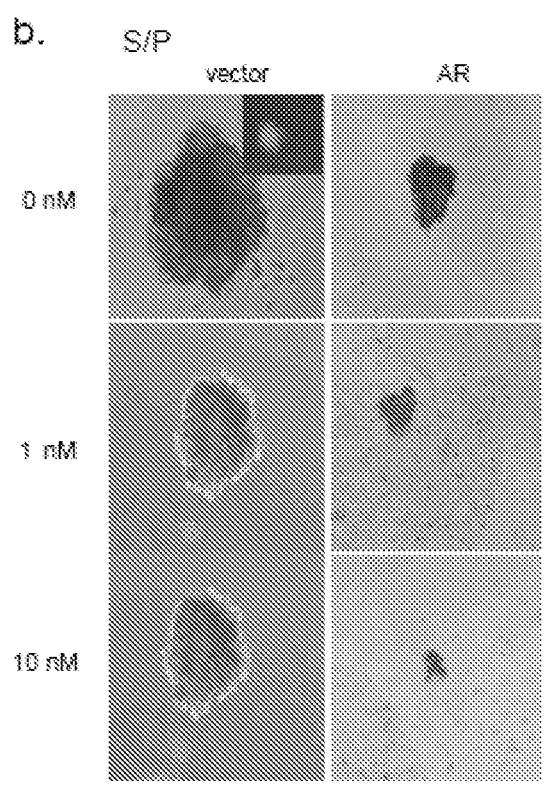
Figure 14:
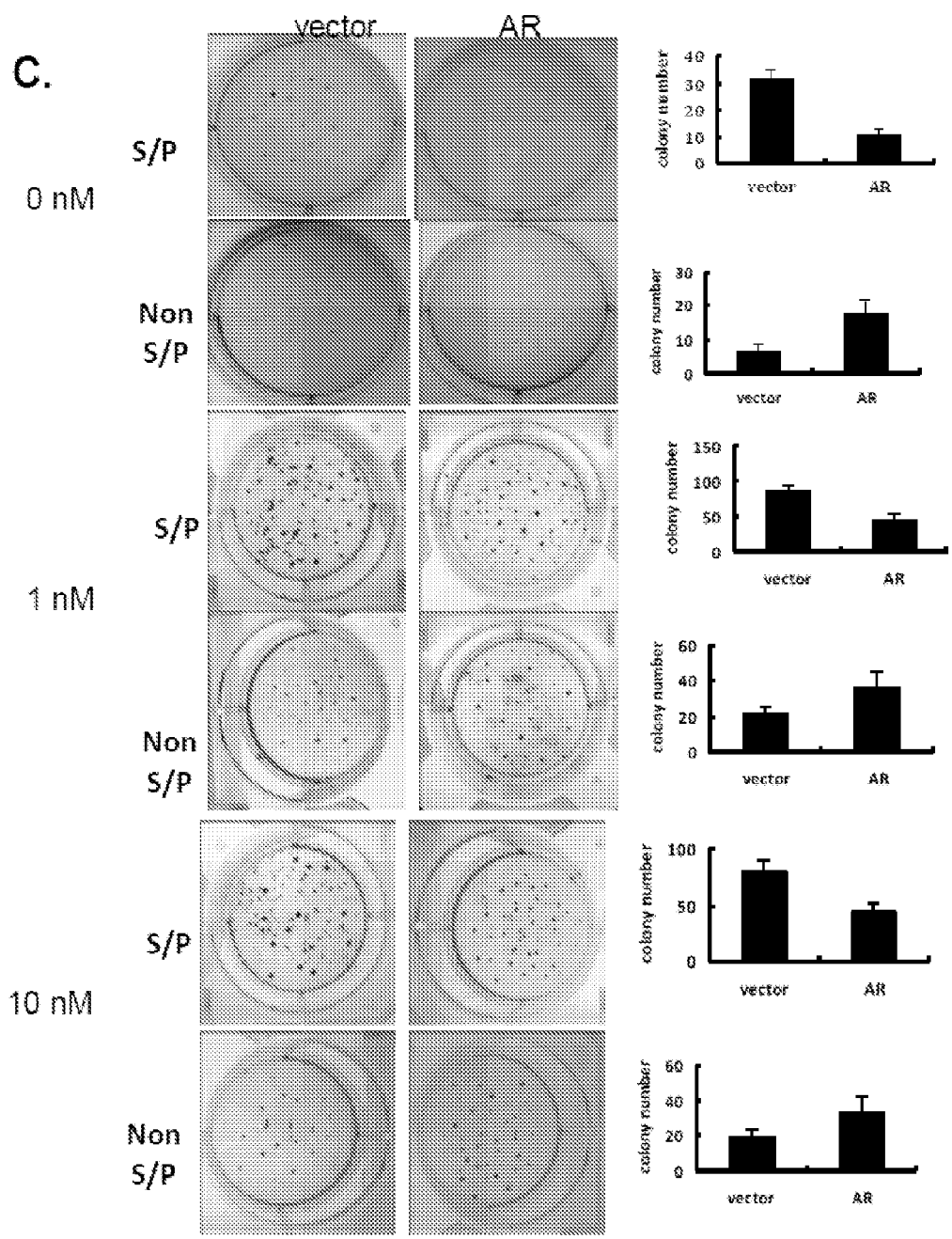
Figure 14:
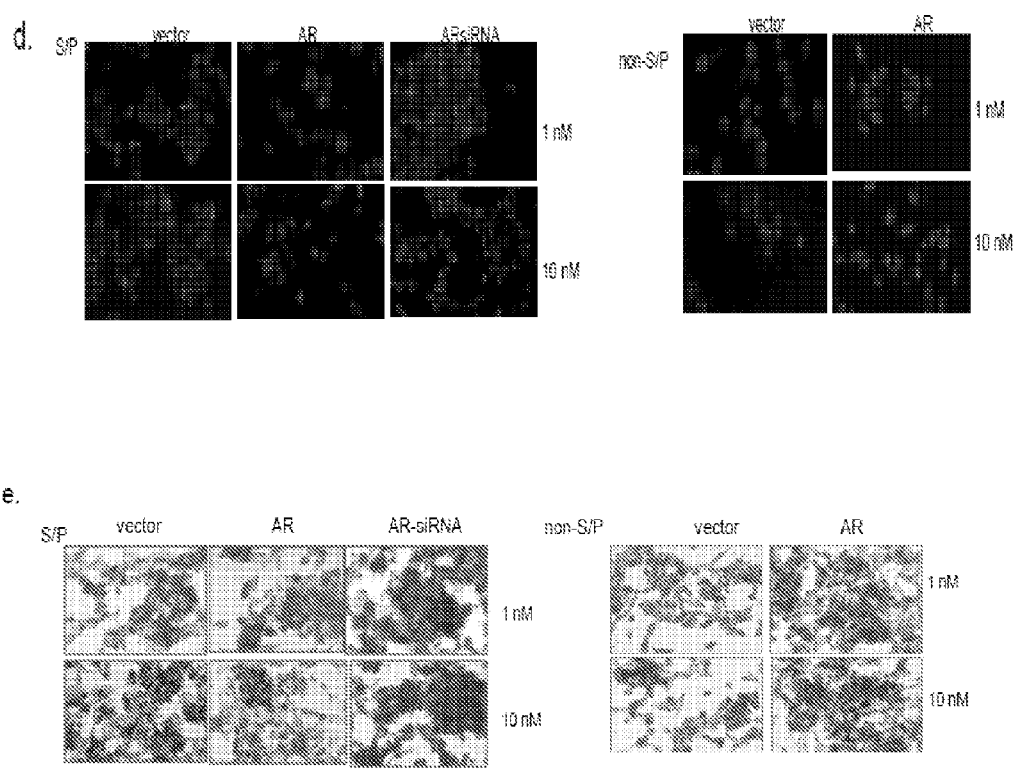
Figure 14:
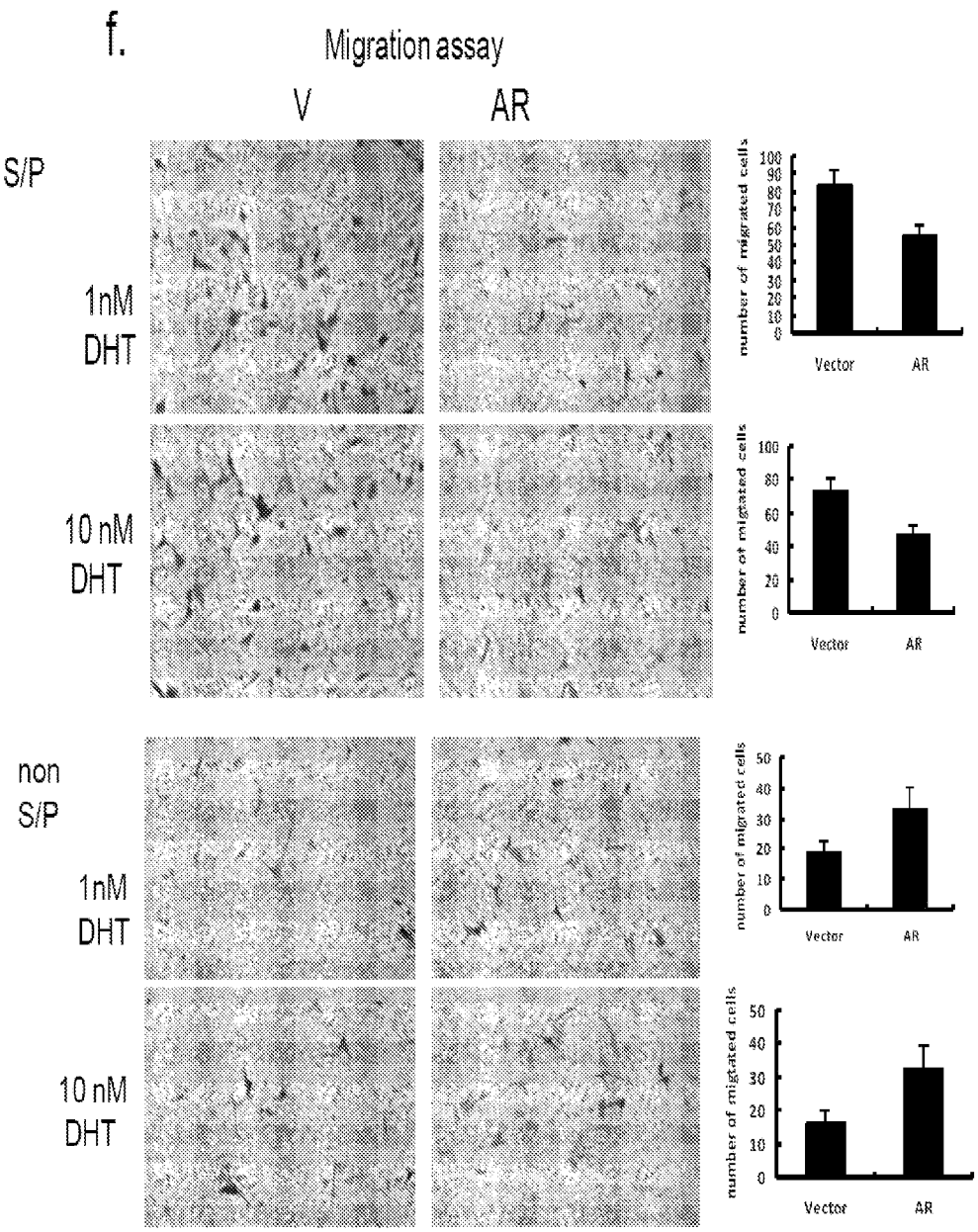
Figure 14:
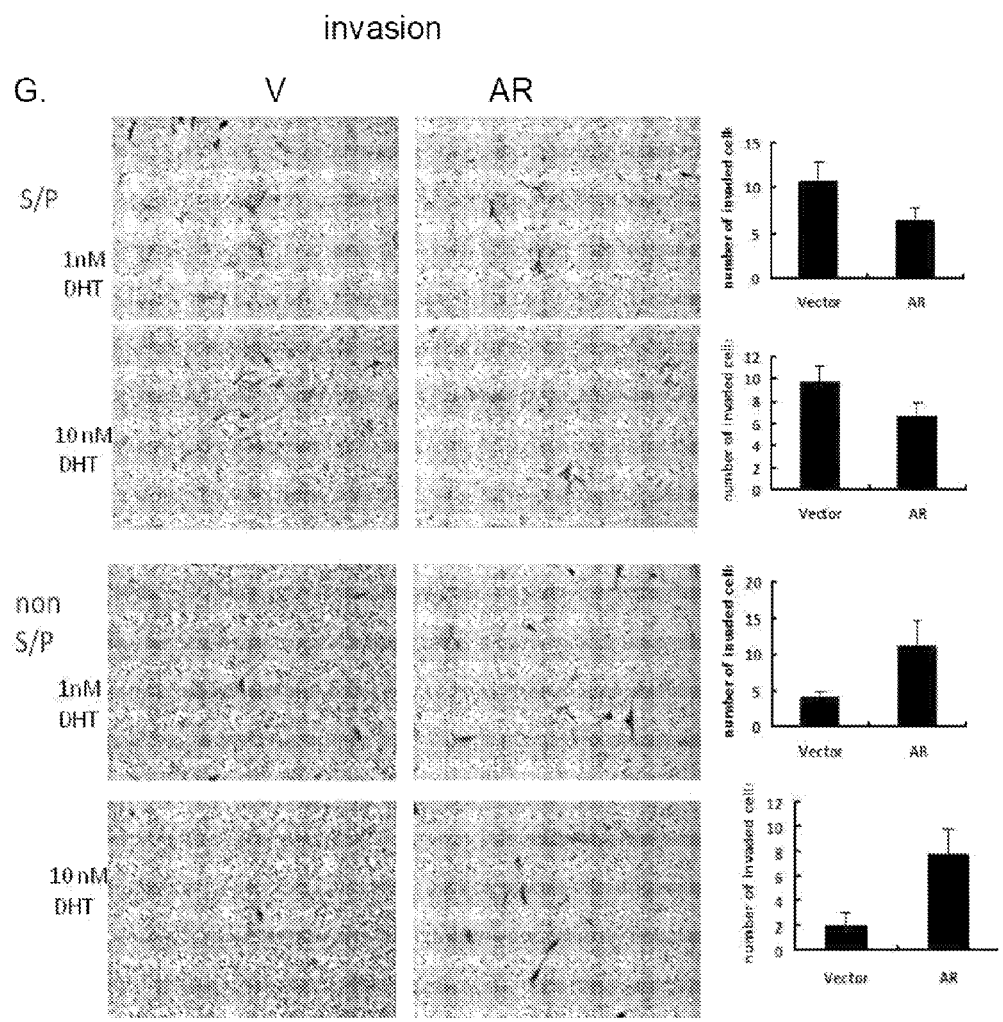

In order to investigate the role of AR in self-renewal/proliferation of prostate cancer S/P and non-S/P cells, these two populations of cells were isolated from an androgen dependent prostate cancer cell line, LNCaP using antibodies of CD133 and integrin The examination of stem cell and immunotype marker expressions (supplementary FIGS. 1E, 1F, and 1G) identified that the isolated cells are basal epithelial originated stem cells according to the cell immunotype markers. Initially two markers were used, but the CD133$^+$ cells were always positive for integrin and CD133$^+$ cells have tumor initiating capacity. CD133 antibody was used solely when the magnetic sorting method was applied. In fact, the isolated S/P cells exhibited higher tumorigenicity compared to the non-S/P cells when tested by soft agar colony formation assay. These S/P cells also demonstrated higher migration and invasion ability compared to the non-S/P cells. Very low expression levels (almost no expression) of AR mRNA and protein were detected in the isolated S/P cells. Whether the low level of AR is necessary in self-renewal/proliferation of S/P cells was investigated. AR was expressed into the S/P and non-S/P cells using lentivirus and the role of AR in self-renewal/proliferation of these two populations of cells were examined Three different androgenic concentrations (0, 1, and 10 nM DHT) were used in the initial MTT assay experiment, however, 1 and 10 nM DHT concentrations were used for other assays, considering the human prostate tissue androgenic level, before (7-8 nM) and after (1-3 nM) the ADT therapy. Similar opposite roles of AR in proliferation of the two populations of cells were observed no matter which concentration of DHT was used in the assay. Actually, growth of the prostate cancer S/P cells were shown to be androgen independent. When the proliferation of S/P and non-S/P cells, either vector or AR expressed, was analyzed by MTT assay (FIG. 14A), it was shown that the S/P cells proliferate at a higher rate when AR level was depleted, but their proliferation was inhibited when AR was introduced. On the contrary, the non-S/P cells proliferate at a higher rate when AR was overexpressed. The ability of sphere formation on Matrigel, which is one of characteristics of stem cells, was also tested. It was shown that AR played a suppressive role in the prostatosphere forming ability of the CD133$^+$ S/P cells (FIG. 14B). Similarly, the BrdU labeling assay result (FIG. 14D) and Ki67 staining assay result (FIG. 14E) shows that the vector expressed S/P cells survive better than the AR expressed cells in the absence of androgen. However, on the contrary, the non-S/P cells proliferate at a higher rate when AR is overexpressed. The colony forming ability test on agarose (FIG. 14C) also demonstrated that the S/P cells grow better when AR level is low. However, the non-S/P cells exhibited higher colony forming ability with AR expression. The opposite roles of AR were also observed in their abilities of adhesion and migration (FIGS. 14F and 14G). All of these results indicate that AR played a stimulatory role in proliferation, migration, and invasion of the non-S/P cells, but a suppressive role in the S/P cells. It is interesting to note that the AR roles are opposite in proliferation of two populations of cells from one cell line.

Similar results were obtained with two other PCa cell lines, the LNCaP derived castration resistant C4-2 and another androgen dependent LAPC-4. S/P and non-S/P cells were isolated from these cell lines, marker expressions were examined and the effect of AR expression on their self-renewal/proliferation after infection of lentivirus carrying either AR or vector was investigated similarly as in the LNCaP cell line study. The results of the similar approaches including proliferation assays of MTT, sphere formation, Ki67 staining, BrdU labeling, and invasion and migration assays revealed similar opposite roles of AR in the two populations of cells in those two cell lines. A prostate cancer stem cell line from Celprogen (San Pedro, Calif.) was also used. These cells did not express AR at the protein level and showed S/P marker expression. When AR was expressed transiently and stably into the cells, their self-renewal/proliferating capacity was significantly inhibited.

AR Plays Opposite Roles in S/P and Non S/P Cells of Mouse Tumor Tissues.

Figure 15:
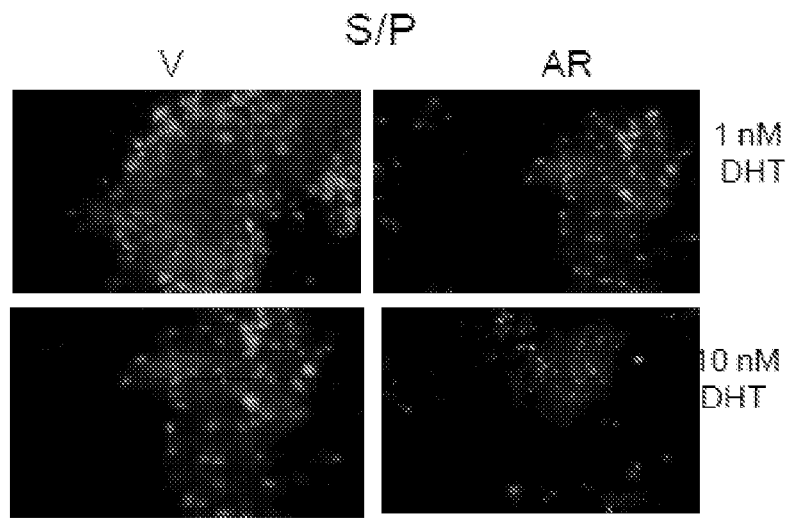
FIG. 15 shows the results of (a) (e) Ki67 IF staining, (b) BrdU labeling experiment, (c), (d) sphere formation assay of S/P and non-S/P cells that were isolated from the mice tumor tissues infected with lentivirus carrying either vector or AR.
Figure 15:
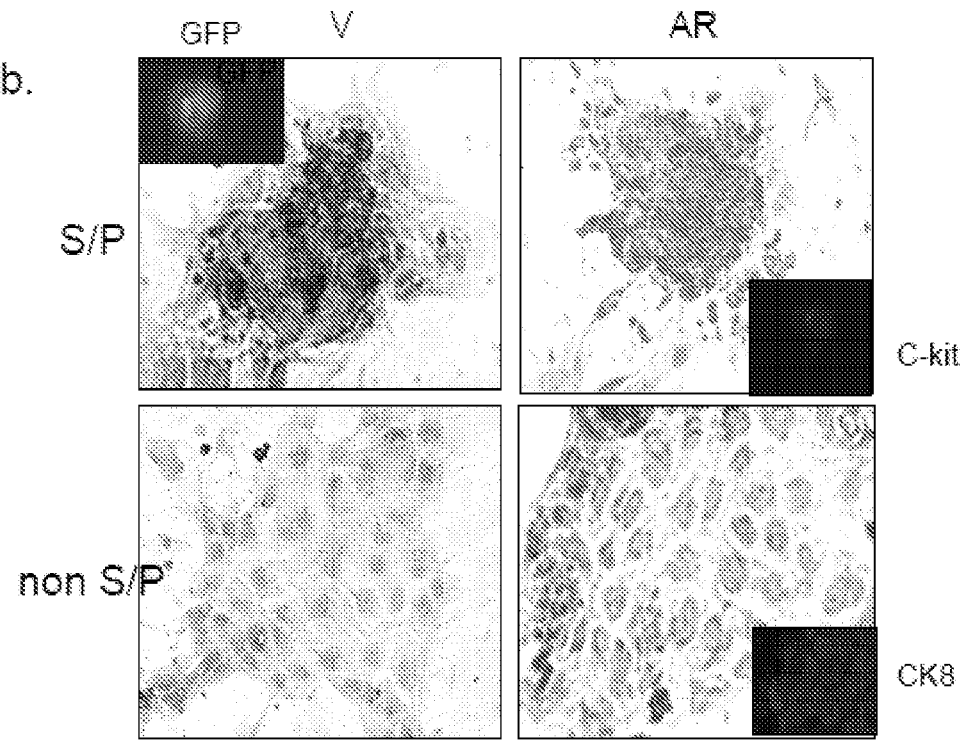
Figure 15:
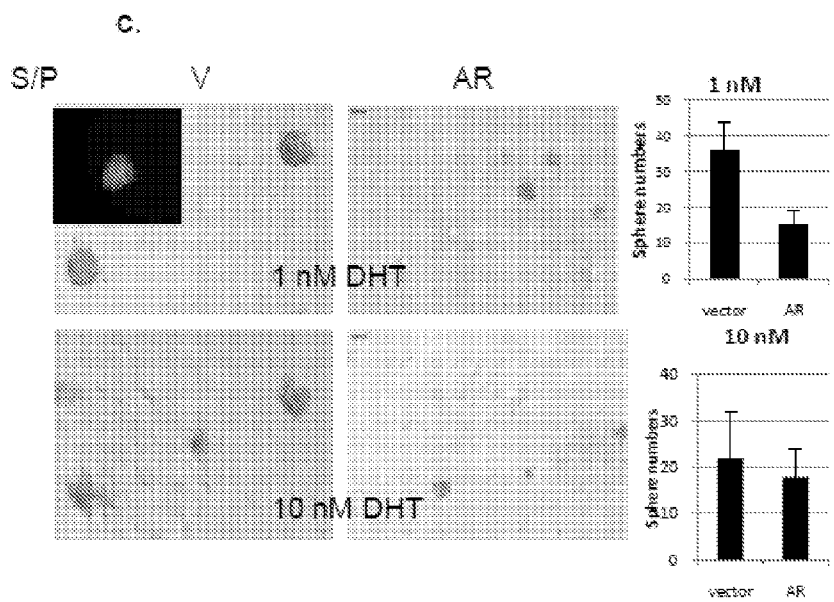
Figure 15:
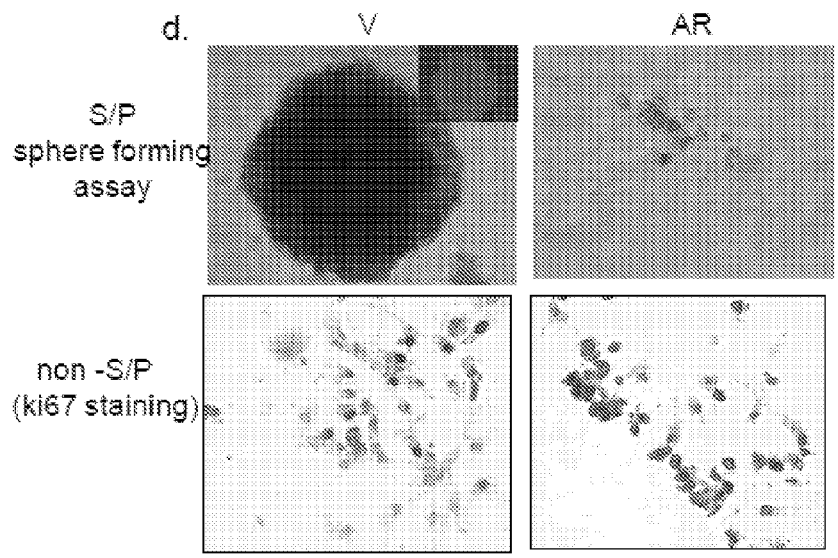

Tumor tissues were obtained from TRAMP mice (B6 background, 26 wks), S/P and non-S/P cells were isolated using antibodies of sca-1 and integrin, and similar growth analyses were performed as in the cell line studies. The flow cytometric separation of two populations of cells and stem cell marker expressions were shown. The Ki67 labeling tests (FIG. 15A) and the BrdU labeling experiment result (FIG. 15B) showed that AR plays a stimulatory role in the non-S/P cells, but suppressive role in the S/P cells. Sphere formation assay using S/P cells also demonstrated the suppressive role of AR in their self-renewal (FIG. 15C). These results are consistent with the cell line data shown in FIG. 14. The C4-2 xenografted tissues were also obtained from mice after injection of C4-2 cells orthotopically into anterior prostate lobes of 8 wks old NOD/SCID mice. S/P and non-S/P cells were isolated, transfected with lentivirus carrying either vector or AR, and similar growth assays were performed. It was demonstrated that the ability of sphere formation in S/P cells was significantly decreased when AR was expressed, but proliferation of non-S/P cells were increased when AR was introduced (FIG. 15D).

S/P Cells have Higher Potential of In Vivo Tumorigenicity and AR Played a Suppressive Role.

Figure 16:
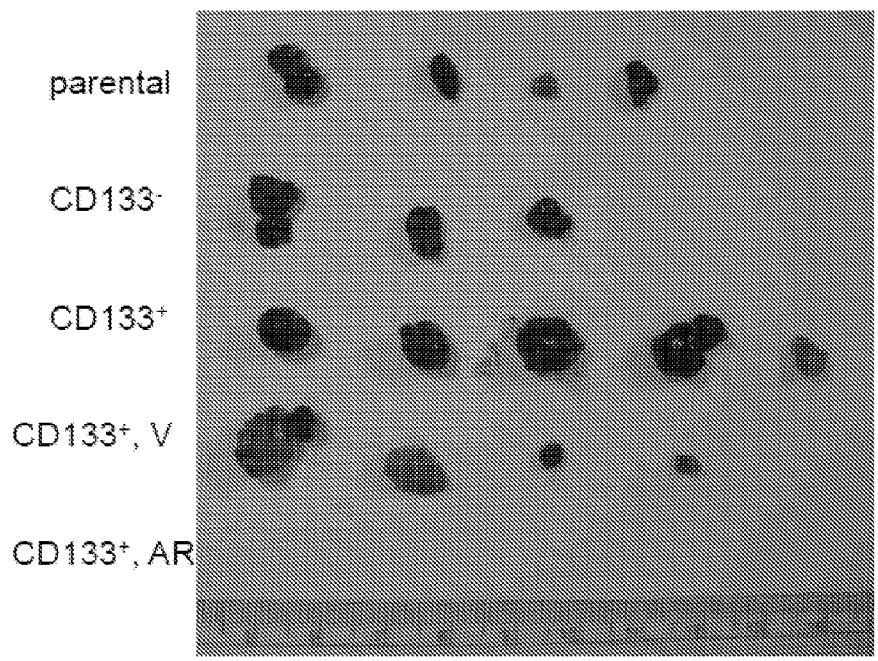
FIG. 16 shows development of subpopulations of LNCaP cells. Five groups of cells, parental, CD133−, CD133+, vector expressing CD133+, AR expressing CD133+, were injected orthotopically into the anterior prostates of nude mice ($1 \times 10^5$ cells/site). At 25 days, all mice were sacrificed and tumor incidence and size of tumors were examined as shown in FIGS. 16a-c. The tumorigenic capacity of S/P cells was decreased upon AR expression.
Figure 16:
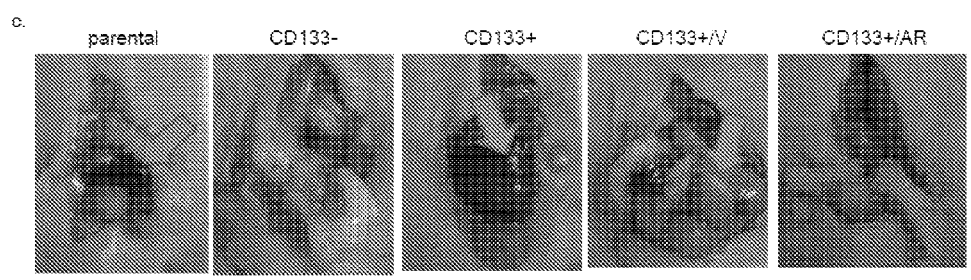

Higher in vitro tumorigenicity of S/P cells compared to the non-S/P and parental cells was shown in soft agar assay using PCa cell lines and the effect of AR expression in their tumorigenicity (of both S/P and non-S/P) was also shown (FIG. 14C). In vivo tumorigenicity of these two populations of cells was then tested as well as the AR expression effect on their tumorigenicity using xenografted mice model. 5 types of LNCaP subpopulations of cells, parental, S/P (CD133$^+$), non-S/P (CD133$^-$), the vector expressing S/P (CD133$^+$/V), and the AR expressing S/P (CD133$^+$/AR) cells were used. Five populations of cells (1×10$^5$) were injected orthotopically into nude mice and their tumor developments were monitored. At around day 20, tumor development was observed in mice injected with the CD133$^+$ and CD133$^+$/V cells. However, retarded tumor development was observed with a CD133$^-$ cells injection and surprisingly none with CD133$^+$/AR cells injection. FIG. 16A shows incidence of tumor development and FIG. 16B represents the size of tumors from the injections of 5 types of cells. These results show that S/P cells have higher tumorigenic potential and the expression of AR suppresses their tumorigenicity. FIG. 16C shows tissue staining results.

Proportion of S/P Cells Increases after ADT/Castration.

Figure 17:
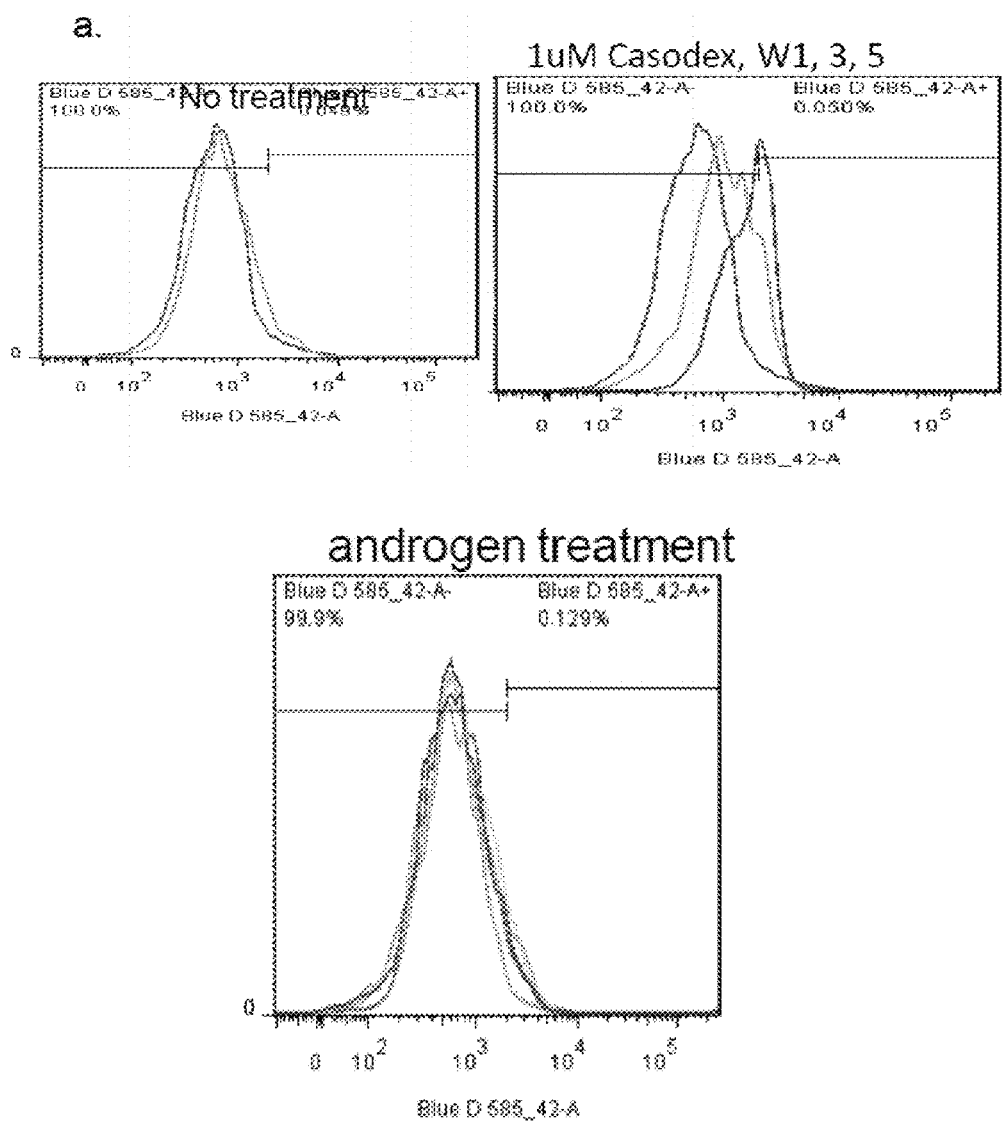
FIG. 17 shows that S/P cells increase after castration/ADT.
Figure 17:
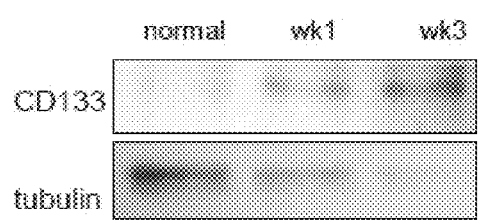
Figure 17:
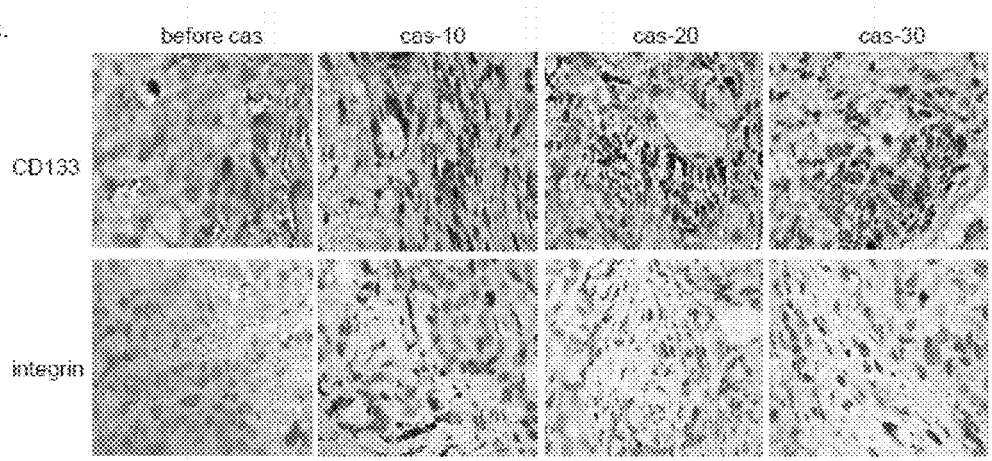
Figure 17:
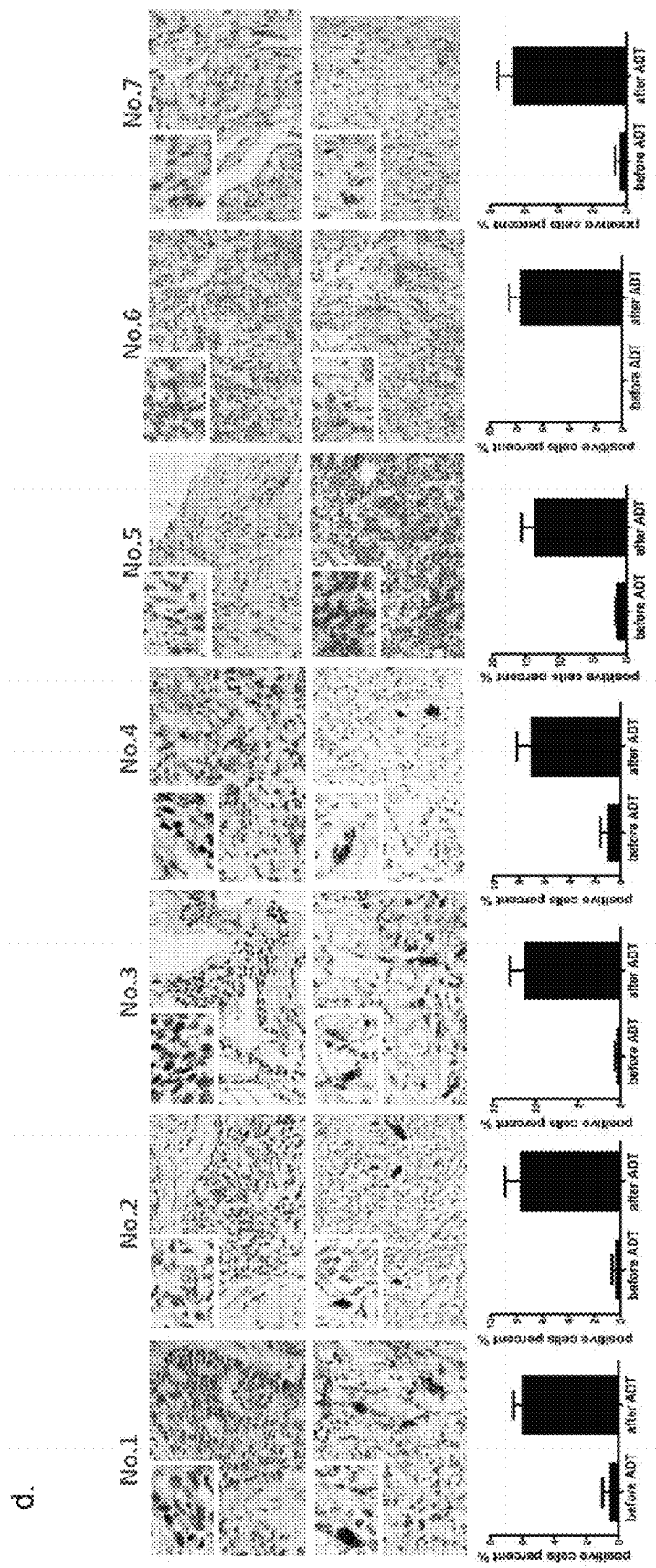

In order to investigate whether S/P cell numbers increase after ADT/castration, LNCaP cells were treated with anti-androgen, Casodex, to mimic castration conditions in vitro. When the LNCaP cells were treated with Casodex for 5 wks continuously, it was found that the CD133$^+$ population cells were significantly increased (FIG. 17A). However, no increase was observed with androgen treatment (FIG. 17B). Similar experiments were performed with C4-2 and LAPC-4 cell lines. Similar effects were observed with LAPC-4 cells yet the effect in C4-2 cells was not as significant as in LNCaP cells.

Whether S/P cells increase after castration/ADT treatment in tumor tissues was examined. Tumor tissues of prostate cancer patients were examined. The tissues were obtained from the same individual, before the therapy and after tumor relapse. A total of seven pair tissue samples were stained with antibodies of the S/P marker proteins, CD133, CD44, and integrin and the immunotype markers, CK5 and CK8. Staining of CD133 is shown in FIG. 17D. The increase in CD133$^+$ cells after ADT was detected in all 7 patients examined. The increases in CD44$^+$ and integrin$^+$ cells were also detected. The cells of CK5 positively stained cells were also increased, but CK8 stained cells were remained similar or even slightly decreased.

The increase in S/P cells were similarly observed in mice tissues. Mice were orthotopically injected with LNCaP and C4-2 cells, castrated and tumor tissues were obtained at days of 10, 20, and 30 days after castration. The numbers of CD133$^+$ cells in tumor tissues were examined in comparison to the tissues before castration. FIG. 17B and FIG. 17C show the staining results of LNCaP and C4-2 cell line, respectively, demonstrating significant increase in CD133$^+$ cells and integrin$^+$ cells in tissues of castration resistant tumors. Collectively, tumor tissue staining data of mice and human indicate S/P cells increase after castration/ADT.

AR Expression is Critical in Determining Stemness of S/P Cells Vs Driving into Differentiation Axis.

Figure 18:
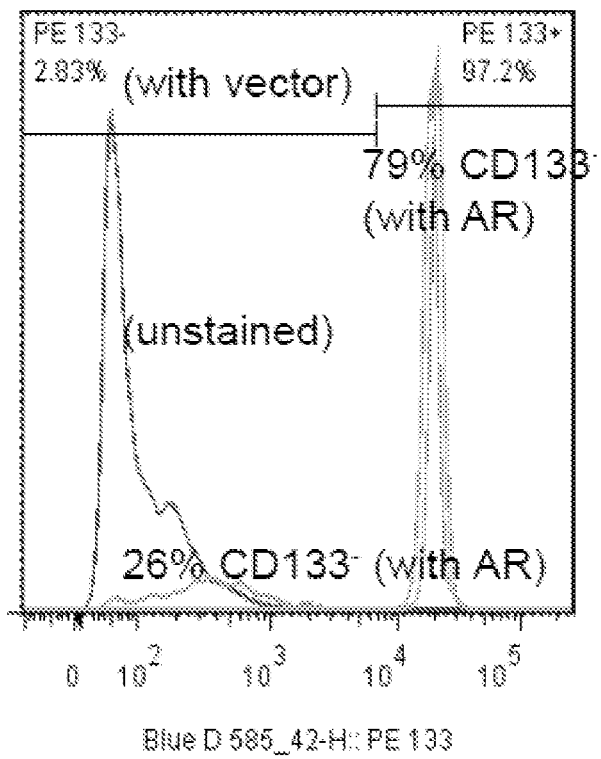
FIG. 18 shows that AR expression drives S/P cells into more differentiated cells.
Figure 18:
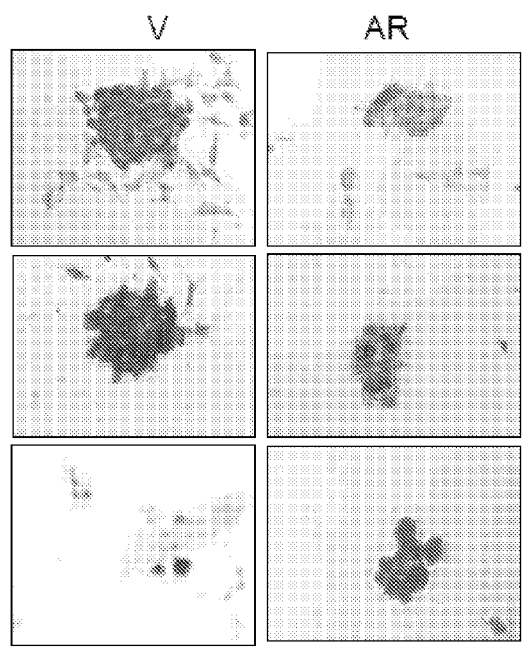
Figure 18:
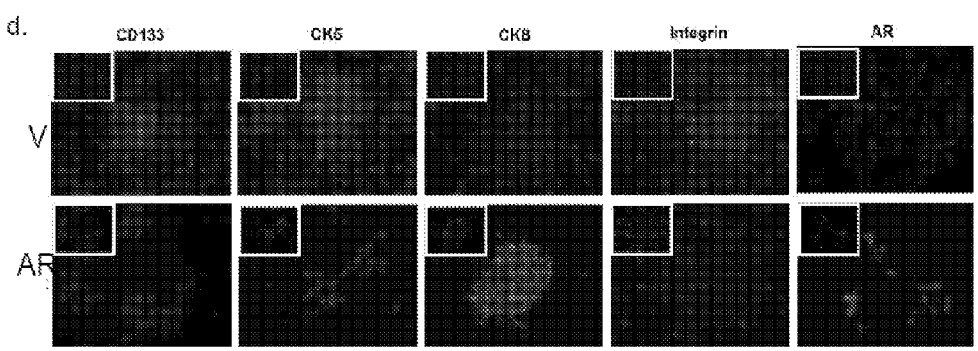
Figure 18:
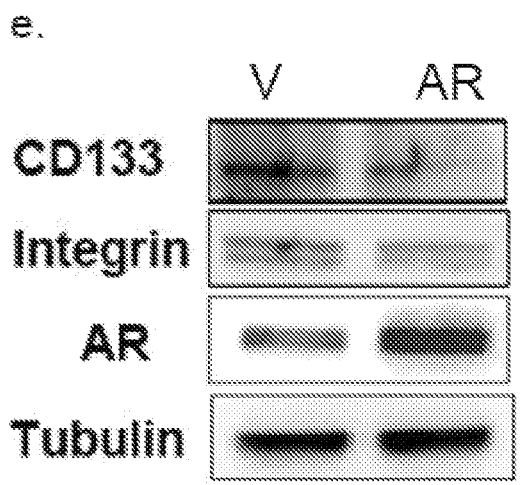
Figure 18:
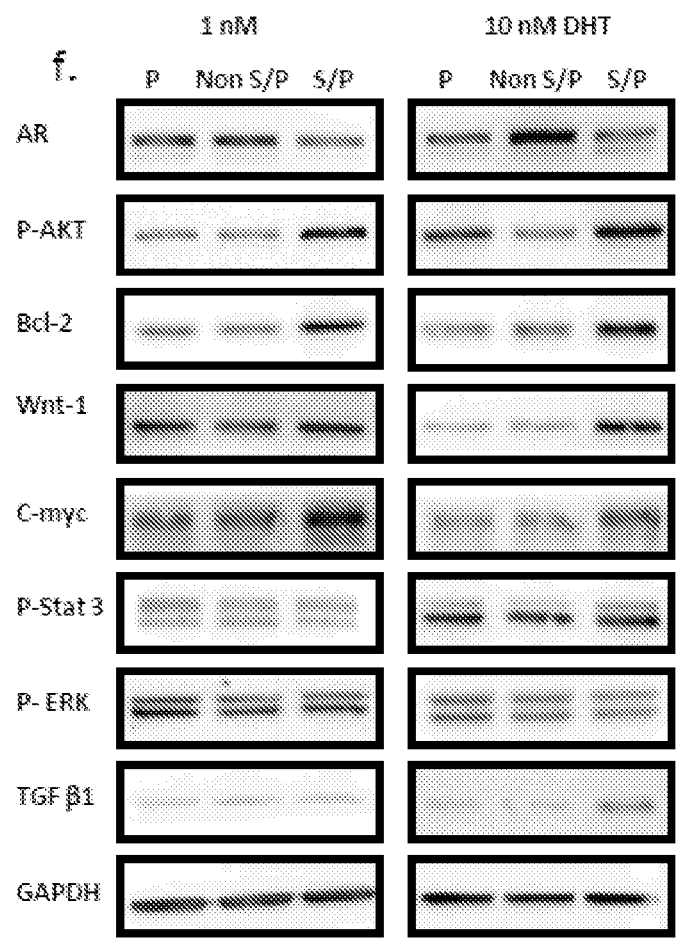
Figure 18:
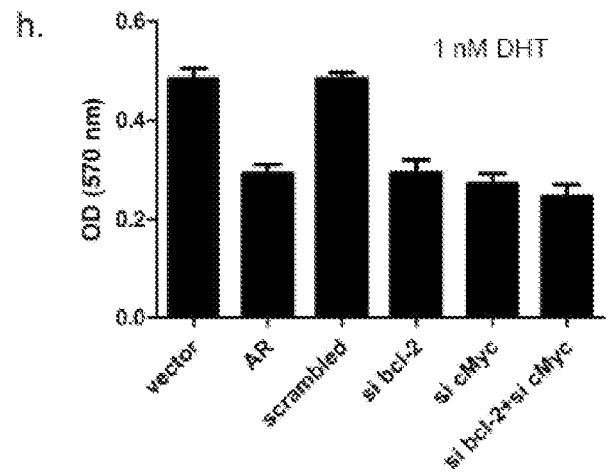
Figure 18:
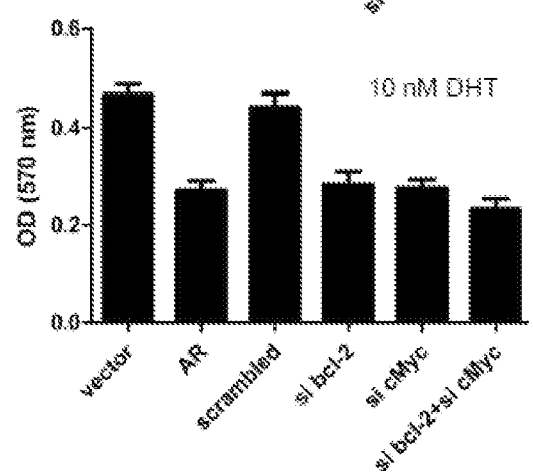
Figure 18:
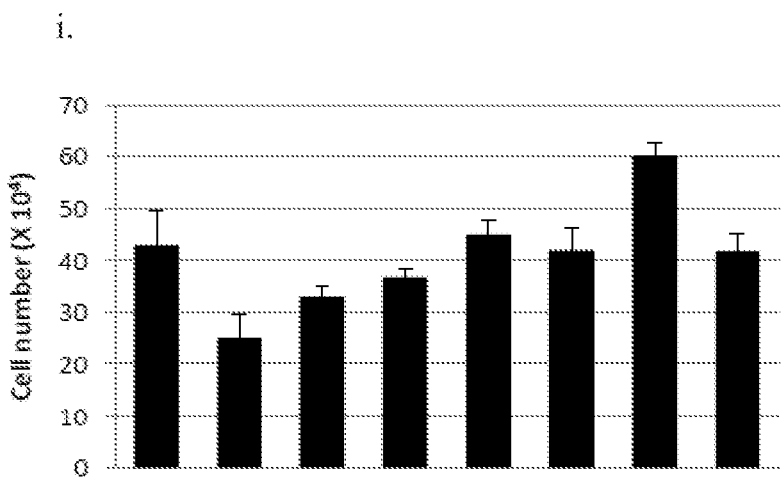

The significance of AR depletion in prostate cancer S/P cells was examined. Forced expression of AR resulted in conversion of CD133$^+$ cells into CD133$^-$ cells. The flow cytometric analysis showed that the number of CD133$^-$ cells was increased from 2.1 to 21% upon AR expression (FIG. 18A). However, androgen treatment did not result in such an increase (FIG. 18B). The expression of the stem cell markers was also shown decreased upon forced expression of AR, but the expression of the differentiation markers was increased (FIG. 18C-E). This result indicates that the depletion of AR is critical in maintaining stemness of S/P cells while AR expression led cells to differentiate into terminally differentiated luminal epithelial cells.

Activation of Downstream Signaling in AR Depleted S/P Cells.

The activation of known AR mediated downstream signaling pathways was investigated. As shown in FIGS. 18F and G, several signaling pathways including Akt, Erk, Wnt, and Stat3 were shown activated and higher expressions of bcl-2, c-myc, and p21 molecules were detected in LNCaP-S/P cells. Interestingly, this activation/higher expression was reversed when AR expression was forced back in the cells indicating that these molecules are mediated by the depletion of AR expression (FIG. 18E). In order to test whether the activation of these signaling pathways and higher expression of the molecules are critical in their self-renewal/proliferation, S/P cells were transfected with their inhibitor/siRNAs. As shown in FIG. 18H, the proliferation was significantly inhibited upon transfection of siRNAs against bcl-2 and c-myc and the treatment with an inhibitor of the Akt pathway indicating that the activation/high expression of these molecules are important in their self-renewal. When constitutively active forms of Akt and bcl-2 are introduced back to the AR expressed cells, the inhibitory effect of cell growth was reversed, showing that the activation of Akt and high expression of bcl-2 are critical in their self-renewal/proliferation (FIG. 18I). The similar profiles of activation of signaling pathways in S/P cells were also observed in C4-2 and Celprogen PCSC cell line.

In Vitro Combinatory Use of Inhibitors of Signaling Molecules with γ-TT and/or 5-AZA Showed Synergistic Effect of Killing PCa S/P Cells.

Figure 19:
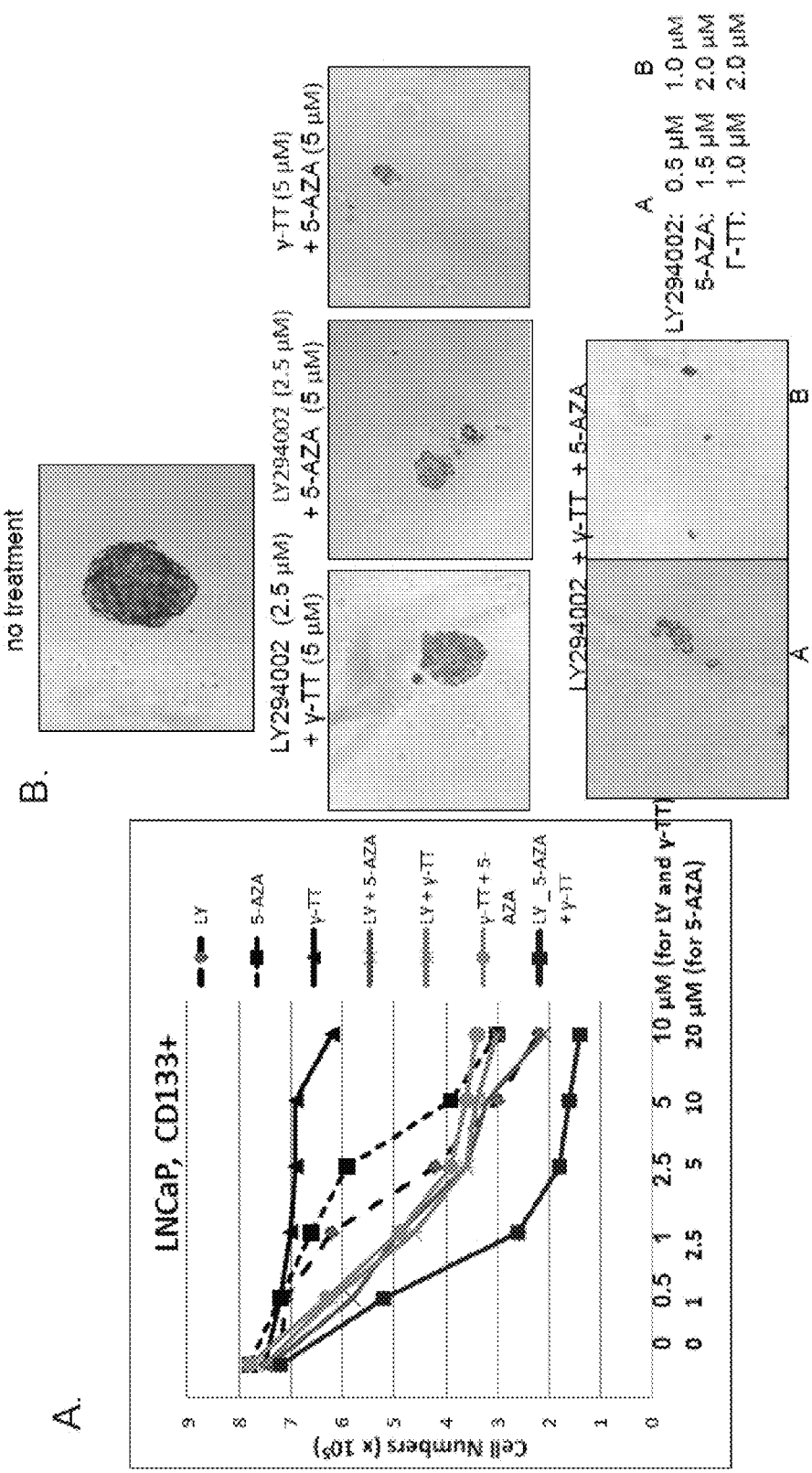
FIG. 19 shows the results of a mechanism study.
Figure 19:
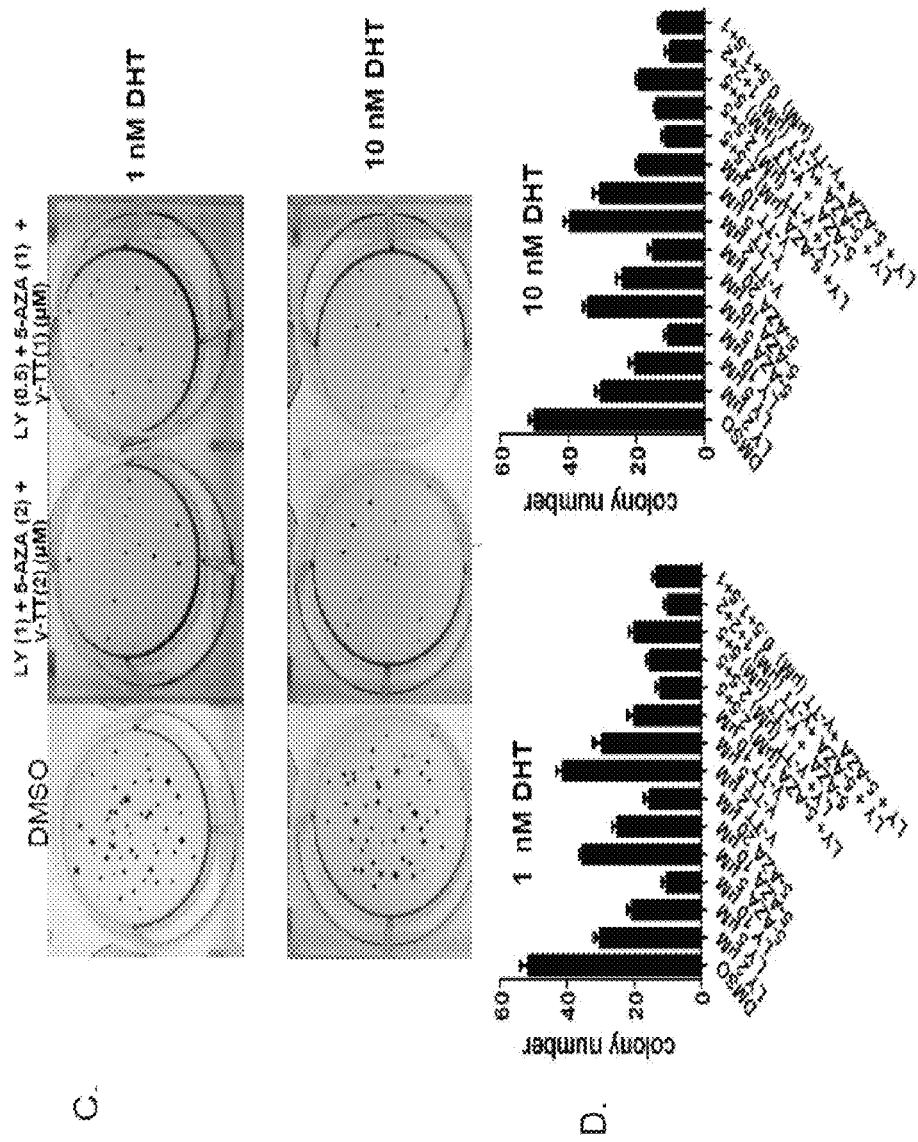

The inhibitory effect of γ-TT on proliferation of the S/P cells was observed. It was found that treatment with 5-AZA also inhibits proliferation of S/P cells. Induction of AR expression by 5-AZA in LNCaP CD133$^+$ cells was shown. The inhibitory effect of these three molecules on proliferation of the S/P cells when used individually is represented in FIG. 19A. The effect of combined use of these molecules to block self-renewal/proliferation of the S/P cells was tested. As an inhibitor of signaling molecules, an inhibitor of Akt signaling was selected since it showed most significant inhibitory effect on self-renewal/proliferation of the S/P cells when tested alone. The effect of a combinations of two drugs selected among three drugs, LY294002 (inhibitor of Akt pathway), γ-TT, and 5-AZA was tested. As shown in FIG. 19B, when two compounds were used together, the IC$_{50}$ values were significantly lowered and when three compounds were used together, the inhibitory effect was more severe, which lowered the IC$_{50}$ of the individual compound to lower than 1 μM from the range between 2.5 and 5 μM. The test results of the combination therapies using soft agar (FIG. 19C) and sphere formation assays (FIG. 19D) confirmed the MTT results. One method of two drug combination therapy was selected based on these three growth assays. This combination is the use of γ-TT and 5-AZA. From all the in vitro tests including an LD test, a minimum dose of these drugs that kills S/P cells was determined. This strategy was used for an in vivo study. When tumors developed the mice were castrated and ASC-J9 was injected, Two or three combinations of the drugs that target S/P population cells were administered. A tumor development curve indicated the recurrence of castration resistant tumors.

The prostate cancer therapies up to date have focused on targeting androgen/AR signaling without considering cell type specific AR roles. However, AR roles are different in cell types and tumor stages and could be why ADT of prostate cancer fails. All results obtained from the isolated S/P and non-S/P cells of prostate cancer cell lines and tumor tissues indicate that the role of AR in self renewal/proliferation of these two population cells were opposite, a suppressor in S/P cells and a stimulator in non-S/P cells. Considering these two population cells co-exist in tumor tissues, the current ADT method may not be the right choice for prostate cancer treatment.

These studies clearly demonstrated that AR indeed plays a negative role in tumorigenicity of the S/P cells (FIG. 15) and this result led us to conclude that the current ADT may aggravate prostate cancer by stimulating S/P originated tumorigenicity. It is possible that tumors develop from two population cells and AR signaling in luminal cells becomes more activated in the presence of low levels of androgen by several known mechanisms and the PSA level increase observed clinically is from this luminal part of the cells. Therefore, it evident that two populations of cells, S/P and non S/P can be targeted and combination therapy can be used to do so. The in vitro experiments set forth herein indicate that the use of two or three compounds together exerted a better effect. The toxicity associated with using many drug compounds may cause problems, however, the IC$_{50}$ value was greatly reduced by combining these drugs. Furthermore, the mouse experiment on testing the LD value did not show toxicity problems. The results of the in vivo studies clearly showed that the occurrence and growth of the castration resistant tumors were significantly reduced by this combination therapy. In conclusion, a new therapy targeting S/P and non-S/P cells simultaneously, which comprise castration resistant tumor tissues has been established.

What is claimed is:

1. A method of delaying the recurrence of prostate cancer in a subject, comprising administering to the subject an effective amount of one or more agents that inhibit proliferation of CK5+ prostate cancer basal epithelial cells selected from the group consisting of: LY-294002, 5-azacytidine, and gamma-tocotrienol, wherein the subject has been treated for prostate cancer with an anti-androgen or an anti-androgen receptor agent and wherein the subject is at risk for recurrence of prostate cancer.

2. The method of claim 1, wherein the anti-androgen or anti-androgen receptor agent inhibits proliferation of prostate luminal epithelial cells, stromal cells or a combination of prostate luminal epithelial and stromal cells.

3. The method of claim 1, wherein treatment with the anti-androgen or anti-androgen receptor agent occurs prior to or concurrently with administration of the agent that inhibits proliferation of prostate basal epithelial cells.

4. The method of claim 1, wherein the anti-androgen or anti-androgen receptor agent is selected from the group consisting of: flutamide (Eulexin), bicalutamide (Casodex), andnilutamide (Nilandron) and ASC-J9.

5. The method of claim 4, wherein the agent is ASC-J9.

6. The method of claim 1, wherein the agent that inhibits proliferation of prostate basal epithelial cells is selected from the group consisting of: an estrogen receptor 0 agonist, a methylation agent and an AKT inhibitor.

7. The method of claim 2, wherein two or more anti-androgens or anti-androgen receptor agents are administered to the subject.

8. The method of claim 1, wherein two or more agents that inhibit proliferation of basal epithelial cells are administered to the subject.

9. The method of claim 1, further comprising administering to the subject an anti-inflammatory agent.

10. The method of claim 9, wherein the anti-inflammatory agent is selected from the group consisting of anti-monocyte chemotactic protein 1 (anti-CCL2) monoclonal antibody, anti-CCL3 monoclonal antibody and an anti-CCL4 monoclonal antibody.

11. A method of treating a recurrence of prostate cancer in a subject that has been treated for prostate cancer with an anti-androgen or an anti-androgen receptor agent, comprising
   a. selecting a subject with a recurrence of prostate cancer, wherein the prostate cancer comprises CK5+ basal epithelial cells and
   b. administering to the subject an effective amount of an agent that inhibits proliferation of CK5+ basal epithelial cells.

12. The method of claim 11, wherein the subject has been treated with an anti-androgen or an anti-androgen receptor agent that inhibits proliferation of prostate luminal epithelial cells, stromal cells or a combination of prostate luminal epithelial and stromal cells.

13. The method of claim 12, wherein treatment with the anti-androgen or anti-androgen receptor agent occurs prior to or concurrently with administration of the agent that inhibits proliferation of basal epithelial cells.

14. The method of claim 12, wherein the anti-androgen or anti-androgen receptor agent is selected from the group consisting of flutamide (Eulexin), bicalutamide (Casodex), andnilutamide (Nilandron) and ASC-J9.

15. The method of claim 14, wherein the agent is ASC-J9.

16. The method of claim 11, wherein the agent that inhibits proliferation of prostate basal epithelial cells is selected from the group consisting of an estrogen receptor β agonist, a methylation agent and an AKT inhibitor.

17. The method of claim 12, wherein two or more anti-androgens or anti-androgen receptor agents are administered to the subject.

18. The method of claim 11, wherein two or more agents that inhibit proliferation of basal epithelial cells are administered to the subject.

19. The method of claim 11, further comprising administering to the subject an anti-inflammatory agent.

20. The method of claim 19, wherein the anti-inflammatory agent is selected from the group consisting of anti-monocyte chemotactic protein 1 (anti-CCL2) monoclonal antibody, anti-CCL3 monoclonal antibody and anti-CCL4 monoclonal antibody.

* * * * *

UNITED STATES PATENT AND TRADEMARK OFFICE
CERTIFICATE OF CORRECTION

PATENT NO. : 9,463,242 B2  Page 1 of 1
APPLICATION NO. : 14/115217
DATED : October 11, 2016
INVENTOR(S) : Chawnshang Chang It is certified that error appears in the above-identified patent and that said Letters Patent is hereby corrected as shown below:

In the Claims

At Column 31, Line 34:
Please delete the text "an estrogen receptor 0 agonist" and replace with --an estrogen receptor β agonist--.

Signed and Sealed this
Eleventh Day of April, 2017

Michelle K. Lee
*Director of the United States Patent and Trademark Office*